US012735503B2

(12) United States Patent
Harris et al.

(10) Patent No.: US 12,735,503 B2
(45) Date of Patent: Sep. 15, 2026

(54) ANTI-MUC1-C ANTIBODIES AND CAR-T STRUCTURES

(71) Applicant: TeneoBio, Inc., Thousand Oaks, CA (US)

(72) Inventors: Katherine Harris, Thousand Oaks, CA (US); Brian Avanzino, Thousand Oaks, CA (US); Nathan Trinklein, Thousand Oaks, CA (US); Karen Chang, Thousand Oaks, CA (US); Nicole Allen, Thousand Oaks, CA (US)

(73) Assignee: TeneoBio, Inc., Thousand Oaks, CA (US)

( * ) Notice: Subject to any disclaimer, the term of this patent is extended or adjusted under 35 U.S.C. 154(b) by 458 days.

(21) Appl. No.: 18/547,663

(22) PCT Filed: Feb. 28, 2022

(86) PCT No.: PCT/US2022/018117

§ 371 (c)(1),
(2) Date: Aug. 23, 2023

(87) PCT Pub. No.: WO2022/183101

PCT Pub. Date: Sep. 1, 2022

(65) Prior Publication Data

US 2024/0182597 A1 Jun. 6, 2024

Related U.S. Application Data

(60) Provisional application No. 63/154,618, filed on Feb. 26, 2021.

(51) Int. Cl.

| | |
|---|---|
| ***C07K 16/30*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/705*** | (2006.01) |
| ***C12N 5/0783*** | (2010.01) |

(52) U.S. Cl.

CPC .......... *C07K 16/3092* (2013.01); *A61K 40/11* (2025.01); *A61K 40/31* (2025.01); *A61K 40/4257* (2025.01); *A61P 35/00* (2018.01); *C07K 14/7051* (2013.01); *C12N 5/0636* (2013.01); *A61K 2239/31* (2023.05); *A61K 2239/38* (2023.05); *A61K 2239/49* (2023.05); *A61K 2239/59* (2023.05); *C07K 2317/569* (2013.01); *C07K 2317/92* (2013.01); *C07K 2319/33* (2013.01); *C12N 2510/00* (2013.01)

(58) Field of Classification Search

CPC ................................................. C07K 16/3092

See application file for complete search history.

(56) References Cited

U.S. PATENT DOCUMENTS

| | | | |
|---|---|---|---|
| 4,275,149 | A | 6/1981 | Litman et al. |
| 4,816,567 | A | 3/1989 | Cabilly et al. |
| 5,225,539 | A | 7/1993 | Winter |
| 5,500,360 | A | 3/1996 | Ahlquist et al. |
| 5,500,362 | A | 3/1996 | Robinson et al. |
| 5,585,089 | A | 12/1996 | Queen et al. |
| 5,585,097 | A | 12/1996 | Bolt et al. |
| 5,595,097 | A | 1/1997 | Anderson |
| 5,693,761 | A | 12/1997 | Queen et al. |
| 5,821,337 | A | 10/1998 | Carter et al. |
| 5,877,299 | A | 3/1999 | Thomas et al. |
| 5,929,212 | A | 7/1999 | Jolliffe et al. |
| 5,968,509 | A | 10/1999 | Gorman et al. |
| 6,037,453 | A | 3/2000 | Jardieu et al. |
| 6,407,213 | B1 | 6/2002 | Carter et al. |
| 6,548,640 | B1 | 4/2003 | Winter |
| 6,706,265 | B1 | 3/2004 | Bolt et al. |
| 6,750,325 | B1 | 6/2004 | Jolliffe et al. |
| 6,982,321 | B2 | 1/2006 | Winter |
| 7,083,785 | B2 | 8/2006 | Browning et al. |
| 7,262,276 | B2 | 8/2007 | Huang et al. |
| 7,381,803 | B1 | 6/2008 | Weiner et al. |
| 7,541,513 | B2 | 6/2009 | Bruggeman et al. |
| 7,635,472 | B2 | 12/2009 | Kufer et al. |
| 7,691,804 | B2 | 4/2010 | Jeffrey et al. |
| 7,728,114 | B2 | 6/2010 | Mach et al. |
| 7,862,813 | B2 | 1/2011 | Bjork, Jr. |
| 8,236,308 | B2 | 8/2012 | Kischel et al. |
| 8,367,888 | B2 | 2/2013 | Brüggemann et al. |

(Continued)

FOREIGN PATENT DOCUMENTS

| | | | |
|---|---|---|---|
| CA | 2828347 | A1 | 9/2012 |
| CN | 1551886 | A | 12/2004 |

(Continued)

OTHER PUBLICATIONS

"A Global Search Engine for Antibodies (A Search for "#sc-57037" in the Antibody Directory, the Details for "#sc-57037" in the Antibody Directory, and A Search for "#sc-57037" in the Antibody Registry)," cited on Feb. 24, 2023, in the EP Opposition for EP2780375, 5 Pages.

(Continued)

*Primary Examiner* — Prema M Mertz

(74) *Attorney, Agent, or Firm* — Haynes and Boone LLP

(57) ABSTRACT

Anti-MUC1-C antibodies (e.g., UniAbs™) and CAR-T structures are disclosed, along with methods of making such antibodies and CAR-T structures, compositions, including pharmaceutical compositions, comprising such antibodies and CAR-T structures, and their use to treat disorders that are characterized by the expression of MUC1-C.

13 Claims, 9 Drawing Sheets

Specification includes a Sequence Listing.

(56) References Cited

U.S. PATENT DOCUMENTS 8,703,485 B2 4/2014 Buelow
8,883,150 B2 11/2014 Craig et al.
9,034,324 B2 5/2015 Kalled et al.
9,150,664 B2 10/2015 Kufer et al.
9,340,621 B2 5/2016 Kufer et al.
9,365,655 B2 6/2016 Craig et al.
9,598,500 B2 3/2017 Kufer et al.
9,650,430 B2 5/2017 Browning et al.
9,657,102 B2 5/2017 Smith et al.
10,494,416 B2 12/2019 Browning et al.
10,766,969 B2 9/2020 Kufer et al.
10,934,363 B2 3/2021 Fan et al.
11,072,656 B2 7/2021 Smith et al.
11,155,621 B2 10/2021 Smith et al.
11,186,639 B2 11/2021 Harris et al.
11,384,153 B2 7/2022 Smith et al.
11,390,681 B2 7/2022 Harris et al.
11,421,027 B2 8/2022 Trinklein et al.
11,427,642 B2 8/2022 Trinklein et al.
11,434,299 B2 9/2022 Force Aldred et al.
11,505,606 B2 11/2022 Trinklein et al.
11,613,572 B2 3/2023 Trinklein et al.
11,905,326 B2 2/2024 Trinklein et al.
2001/0024811 A1 9/2001 Khosla et al.
2001/0024812 A1 9/2001 Guegler et al.
2002/0066516 A1 6/2002 Cornell
2004/0110226 A1 6/2004 Lazar et al.
2004/0229310 A1 11/2004 Simmons
2005/0048572 A1 3/2005 Reilly et al.
2006/0008548 A1 1/2006 Tung
2007/0065437 A1 3/2007 Elson et al.
2007/0071675 A1 3/2007 Wu et al.
2007/0212733 A1 9/2007 Martin
2009/0098134 A1 4/2009 Buelow
2010/0122358 A1 5/2010 Brüggemann et al.
2010/0150918 A1 6/2010 Kufer et al.
2011/0129458 A1 6/2011 Dolk et al.
2013/0129729 A1 5/2013 Kischel et al.
2013/0156769 A1 6/2013 Kufer et al.
2013/0195888 A1 8/2013 Wang et al.
2013/0273055 A1 10/2013 Borges et al.
2013/0273066 A1 10/2013 Gokarn et al.
2013/0280280 A1 10/2013 Algate et al.
2014/0056897 A1 2/2014 Buelow et al.
2014/0088295 A1 3/2014 Smith et al.
2014/0220021 A1 8/2014 Shibayama et al.
2014/0308285 A1 10/2014 Yan et al.
2015/0095412 A1 4/2015 Xuan
2015/0118251 A1 4/2015 Deslandes et al.
2015/0266966 A1 9/2015 Smith et al.
2015/0337054 A1 11/2015 Gardner, II et al.
2015/0368351 A1 12/2015 Vu et al.
2015/0376287 A1 12/2015 Vu et al.
2016/0046724 A1 2/2016 Brogdon et al.
2016/0159894 A1 6/2016 Hartmann et al.
2016/0166689 A1 6/2016 Adler et al.
2016/0194399 A1 7/2016 Irving et al.
2016/0355591 A1 12/2016 Goldenberg et al.
2017/0051068 A1 2/2017 Pillarisetti et al.
2017/0174770 A1 6/2017 Bruggemann et al.
2017/0240612 A1 8/2017 Bachmann et al.
2017/0275363 A1 9/2017 Chang et al.
2018/0079822 A1 3/2018 Liu et al.
2019/0070290 A1 3/2019 Kischel et al.
2019/0106504 A1 4/2019 Wu et al.
2019/0151448 A1 5/2019 Abel et al.
2019/0225671 A1 7/2019 Van Schooten et al.
2019/0263904 A1 8/2019 Trinklein et al.
2019/0284294 A1 9/2019 Deslandes et al.
2019/0328784 A1 10/2019 Ostertag et al.
2019/0352412 A1 11/2019 Force Aldred et al.
2020/0048348 A1 2/2020 Trinklein et al.
2020/0078399 A1 3/2020 Fan et al.
2020/0085839 A1 3/2020 Sidransky et al.
2020/0095305 A1 3/2020 Browning et al.
2020/0095319 A1 3/2020 Kufer et al.
2020/0123269 A1 4/2020 Fan et al.
2020/0129617 A1 4/2020 Brownstein et al.
2020/0131262 A1 4/2020 Ehninger
2020/0138865 A1 5/2020 Kochenderfer et al.
2020/0157232 A1 5/2020 Trinklein et al.
2020/0181228 A1 6/2020 Bachmann et al.
2020/0190205 A1 6/2020 Adams et al.
2020/0332000 A1 10/2020 McAuley et al.
2020/0339685 A1 10/2020 Schellenberger et al.
2021/0047407 A1 2/2021 Christian et al.
2021/0095022 A1 4/2021 Force Aldred et al.
2021/0139577 A1 5/2021 Dillon et al.
2021/0139584 A1 5/2021 Minella et al.
2021/0147564 A1 5/2021 Trinklein et al.
2021/0163620 A1 6/2021 Granda et al.
2021/0284732 A1 9/2021 Zugmaier et al.
2021/0332133 A1 10/2021 Force Aldred et al.
2021/0340255 A1 11/2021 Harris et al.
2021/0341487 A1 11/2021 Partridge et al.
2021/0355215 A1 11/2021 Jorgensen et al.
2021/0388106 A1 12/2021 Van Schooten et al.
2021/0395298 A1 12/2021 Bondarenko et al.
2021/0403587 A1 12/2021 Buelow et al.
2022/0025047 A1 1/2022 Trinklein et al.
2022/0041742 A1 2/2022 Adams et al.
2022/0064336 A1 3/2022 Kufer et al.
2022/0089729 A1 3/2022 Harris et al.
2022/0098324 A1 3/2022 Weiner et al.
2022/0137010 A1 5/2022 Wen
2022/0144947 A1 5/2022 Smith et al.
2022/0195068 A1 6/2022 Van Schooten et al.
2022/0251243 A1 8/2022 Kufer et al.
2022/0259547 A1 8/2022 Khurshid
2022/0306741 A1 9/2022 Sharma et al.
2022/0306758 A1 9/2022 Smith et al.
2022/0332820 A1 10/2022 Harris et al.
2022/0356268 A1 11/2022 Kufer et al.
2022/0378908 A1 12/2022 Zhu et al.
2022/0389055 A1 12/2022 Davis et al.
2022/0396599 A1 12/2022 Wang et al.
2022/0403035 A1 12/2022 Anlahr et al.
2023/0045100 A1 2/2023 Force Aldred et al.
2023/0057602 A1 2/2023 Burgess et al.
2023/0060847 A1 3/2023 Trinklein et al.
2023/0082151 A1 3/2023 Trinklein et al.
2023/0242668 A1 8/2023 Van Schooten et al.
2023/0257473 A1 8/2023 Trinklein et al.
2023/0272075 A1 8/2023 Trinklein et al.

FOREIGN PATENT DOCUMENTS

CN 1889979 A 1/2007
CN 101627055 A 1/2010
CN 102119174 A 7/2011
CN 1889979 B 9/2012
CN 103619876 A 3/2014
CN 104877026 A 9/2015
CN 104968682 A 10/2015
CN 105143263 A 12/2015
CN 105384825 A 3/2016
CN 105777906 A 7/2016
CN 105968203 A 9/2016
CN 105968204 A 9/2016
CN 106029098 A 10/2016
CN 105384825 B 6/2018
CN 108473589 A 8/2018
CN 101874042 B 9/2018
CN 103703024 B 10/2018
CN 104114578 B 10/2018
CN 101874042 B9 1/2019
CN 104877026 B 10/2019
CN 111683966 A 9/2020
CN 112351997 A 2/2021
CN 112521513 A 3/2021
CN 104710528 B 12/2023
EP 2762496 A1 8/2014
EP 2762497 A1 8/2014
EP 1210425 B2 6/2015

(56) References Cited

FOREIGN PATENT DOCUMENTS

| | | | |
|---|---|---|---|
| EP | 2970472 | A1 | 1/2016 |
| EP | 2780374 | B1 | 8/2019 |
| EP | 2780375 | B1 | 9/2019 |
| EP | 3611193 | A1 | 2/2020 |
| EP | 3623385 | A1 | 3/2020 |
| EP | 3819007 | A1 | 5/2021 |
| EP | 3830122 | A1 | 6/2021 |
| EP | 3912997 | A2 | 11/2021 |
| EP | 3411402 | B1 | 12/2021 |
| EP | 3974453 | A2 | 3/2022 |
| EP | 4039709 | A1 | 8/2022 |
| EP | 4058148 | A1 | 9/2022 |
| EP | 4171750 | A1 | 5/2023 |
| JP | 2012504403 | A | 2/2012 |
| JP | 2012521211 | A5 | 5/2013 |
| JP | 2013528569 | A | 7/2013 |
| JP | 2014500879 | A | 1/2014 |
| JP | 2014515598 | A | 7/2014 |
| JP | 2014520088 | A | 8/2014 |
| JP | 2015521032 | A | 7/2015 |
| JP | 5836927 | B2 | 12/2015 |
| JP | 2015535002 | A | 12/2015 |
| JP | 2016500256 | A | 1/2016 |
| JP | 2016538275 | A | 12/2016 |
| JP | 2019528044 | A | 10/2019 |
| JP | 6923292 | B2 | 8/2021 |
| JP | 7030109 | B2 | 3/2022 |
| RU | 2492186 | C2 | 9/2013 |
| RU | 2561457 | C2 | 8/2015 |
| RU | 2014147452 | A | 6/2016 |
| WO | WO-1996027011 | A1 | 9/1996 |
| WO | WO-1996032478 | A1 | 10/1996 |
| WO | WO-1997034631 | A1 | 9/1997 |
| WO | WO-1998050431 | A2 | 11/1998 |
| WO | WO-2000040716 | A2 | 7/2000 |
| WO | WO-2001012812 | A2 | 2/2001 |
| WO | WO-2001024811 | A1 | 4/2001 |
| WO | WO-2001024812 | A1 | 4/2001 |
| WO | WO-2001077342 | A1 | 10/2001 |
| WO | WO-2001087977 | A2 | 11/2001 |
| WO | WO-2002066516 | A2 | 8/2002 |
| WO | WO-2004106383 | A1 | 12/2004 |
| WO | WO-2005040220 | A1 | 5/2005 |
| WO | WO-2005058815 | A2 | 6/2005 |
| WO | WO-2005061547 | A2 | 7/2005 |
| WO | WO-2006008548 | A2 | 1/2006 |
| WO | WO-2006089232 | A2 | 8/2006 |
| WO | WO-2007042261 | A2 | 4/2007 |
| WO | WO-2007042289 | A2 | 4/2007 |
| WO | WO-2007055916 | A2 | 5/2007 |
| WO | WO-2007066109 | A1 | 6/2007 |
| WO | WO-2007117505 | A2 | 10/2007 |
| WO | WO-2007117600 | A2 | 10/2007 |
| WO | WO-2008119565 | A2 | 10/2008 |
| WO | WO-2008119566 | A2 | 10/2008 |
| WO | WO-2008119567 | A2 | 10/2008 |
| WO | WO-2008151081 | A1 | 12/2008 |
| WO | WO-2009041643 | A1 | 4/2009 |
| WO | WO-2009055669 | A2 | 4/2009 |
| WO | WO-2009132058 | A2 | 10/2009 |
| WO | WO-2010007082 | A1 | 1/2010 |
| WO | WO-2010032061 | A1 | 3/2010 |
| WO | WO-2010037835 | A2 | 4/2010 |
| WO | WO-2010037836 | A2 | 4/2010 |
| WO | WO-2010037837 | A2 | 4/2010 |
| WO | WO-2010037838 | A2 | 4/2010 |
| WO | WO-2010104949 | A2 | 9/2010 |
| WO | WO-2010109165 | A2 | 9/2010 |
| WO | WO-2011069104 | A2 | 6/2011 |
| WO | WO-2011097603 | A1 | 8/2011 |
| WO | WO-2011121110 | A1 | 10/2011 |
| WO | WO-2012066058 | A1 | 5/2012 |
| WO | WO-2012122512 | A1 | 9/2012 |
| WO | WO-2012122528 | A1 | 9/2012 |
| WO | WO-2012143498 | A1 | 10/2012 |
| WO | WO-2012145714 | A2 | 10/2012 |
| WO | WO-2012162067 | A2 | 11/2012 |
| WO | WO-2012163805 | A1 | 12/2012 |
| WO | WO-2013022091 | A1 | 2/2013 |
| WO | WO-2013072406 | A1 | 5/2013 |
| WO | WO-2013072415 | A1 | 5/2013 |
| WO | WO-2013154760 | A1 | 10/2013 |
| WO | WO-2013158856 | A2 | 10/2013 |
| WO | WO-2014022540 | A1 | 2/2014 |
| WO | WO-2014047231 | A1 | 3/2014 |
| WO | WO-2014068079 | A1 | 5/2014 |
| WO | WO-2014089335 | A2 | 6/2014 |
| WO | WO-2014093908 | A2 | 6/2014 |
| WO | WO-2014112144 | A1 | 7/2014 |
| WO | WO-2014122143 | A1 | 8/2014 |
| WO | WO-2014122144 | A1 | 8/2014 |
| WO | WO-2014140248 | A1 | 9/2014 |
| WO | WO-2014141192 | A1 | 9/2014 |
| WO | WO-2014144722 | A2 | 9/2014 |
| WO | WO-2015063339 | A1 | 5/2015 |
| WO | WO-2015095412 | A1 | 6/2015 |
| WO | WO-2015116753 | A1 | 8/2015 |
| WO | WO-2015121383 | A1 | 8/2015 |
| WO | WO-2015130416 | A1 | 9/2015 |
| WO | WO-2015149077 | A1 | 10/2015 |
| WO | WO-2016014789 | A2 | 1/2016 |
| WO | WO-2016014974 | A2 | 1/2016 |
| WO | WO-2016030414 | A1 | 3/2016 |
| WO | WO-2016062990 | A1 | 4/2016 |
| WO | WO-2016079050 | A1 | 5/2016 |
| WO | WO-2016079076 | A1 | 5/2016 |
| WO | WO-2016079081 | A1 | 5/2016 |
| WO | WO-2016079177 | A1 | 5/2016 |
| WO | WO-2016094304 | A2 | 6/2016 |
| WO | WO-2016113555 | A1 | 7/2016 |
| WO | WO-2016124670 | A1 | 8/2016 |
| WO | WO-2016128487 | A1 | 8/2016 |
| WO | WO-2016187546 | A1 | 11/2016 |
| WO | WO-2016187594 | A1 | 11/2016 |
| WO | WO-2017023761 | A1 | 2/2017 |
| WO | WO-2017025038 | A1 | 2/2017 |
| WO | WO-2017031104 | A1 | 2/2017 |
| WO | WO-2017053856 | A1 | 3/2017 |
| WO | WO-2017081211 | A2 | 5/2017 |
| WO | WO-2017122018 | A1 | 7/2017 |
| WO | WO-2017122019 | A1 | 7/2017 |
| WO | WO-2017134134 | A1 | 8/2017 |
| WO | WO-2017223111 | A1 | 12/2017 |
| WO | WO-2018039180 | A1 | 3/2018 |
| WO | WO-2018052503 | A1 | 3/2018 |
| WO | WO-2018083204 | A1 | 5/2018 |
| WO | WO-2018114795 | A1 | 6/2018 |
| WO | WO-2018119215 | A1 | 6/2018 |
| WO | WO-2018237006 | A1 | 12/2018 |
| WO | WO-2018237037 | A2 | 12/2018 |
| WO | WO-2019000223 | A1 | 1/2019 |
| WO | WO-2019006072 | A1 | 1/2019 |
| WO | WO-2019012260 | A1 | 1/2019 |
| WO | WO-2019055689 | A1 | 3/2019 |
| WO | WO-2019075413 | A1 | 4/2019 |
| WO | WO-2019126724 | A1 | 6/2019 |
| WO | WO-2019126756 | A1 | 6/2019 |
| WO | WO-2019133761 | A1 | 7/2019 |
| WO | WO-2019177854 | A1 | 9/2019 |
| WO | WO-2020018922 | A1 | 1/2020 |
| WO | WO-2020025596 | A1 | 2/2020 |
| WO | WO-2020061478 | A2 | 3/2020 |
| WO | WO-2020087065 | A1 | 4/2020 |
| WO | WO-2020206330 | A1 | 10/2020 |
| WO | WO-2020252366 | A1 | 12/2020 |
| WO | WO-2021094000 | A1 | 5/2021 |
| WO | WO-2021127489 | A1 | 6/2021 |
| WO | WO-2021127505 | A1 | 6/2021 |
| WO | WO-2021222578 | A1 | 11/2021 |
| WO | WO-2021222616 | A1 | 11/2021 |
| WO | WO-2021228783 | A1 | 11/2021 |
| WO | WO-2022006316 | A1 | 1/2022 |
| WO | WO-2022103781 | A1 | 5/2022 |
| WO | WO-2022109010 | A1 | 5/2022 |

(56) References Cited

FOREIGN PATENT DOCUMENTS

| | | |
|---|---|---|
| WO | WO-2022183074 A2 | 9/2022 |
| WO | WO-2022183101 A1 | 9/2022 |
| WO | WO-2022212848 A1 | 10/2022 |
| WO | WO-2022216864 A1 | 10/2022 |
| WO | WO-2022221698 A1 | 10/2022 |
| WO | WO-2022271987 A1 | 12/2022 |
| WO | WO-2023004197 A1 | 1/2023 |

OTHER PUBLICATIONS

A Report of an Epitope-exchange Study on the Binding of Vicky-1 to BCMA Epitope Cluster 3, Cited on Feb. 24, 2023, In the EP Opposition for EP2780375, 6 Pages.
Aalberse R.C., et al., "IgG4 Breaking the Rules," Immunology, 2002, vol. 105, pp. 9-19.
Abcam: "Product datasheet, Anti-BCMA antibody [Vicky-1] ab17323," cited on Sep. 9, 2022 in the EP Opposition for EP2780375, 3 Pages.
Adams G.P., et al., "Prolonged in Vivo Tumour Retention of a Human Diabody Targeting the Extracellular Domain of Human HER2/neu," British Journal of Cancer, 1998, vol. 77, No. 9, pp. 1405-1412.
Alanine-Scanning Report, In the EP Opposition for EP2780375, Cited on Feb. 23, 2023, 9 Pages.
Alderson R.F., et al., "CAT-8015: A Second-Generation Pseudomonas Exotoxin A-Based Immunotherapy Targeting CD22-Expressing Hematologic Malignancies," Clinical Cancer Research, Feb. 1, 2009, vol. 15, No. 3, pp. 832-839.
Aldred S.F., "Winning the Numbers Game: Novel Multi-specific Therapeutics from a Diverse Collection of Human Domain Antibodies," Teneobio, 2016, pp. 1-16, [Retrieved on Oct. 10, 2016] Retrieved from URL: https://2019.lakepharma.com/files/symposiums/Winning%20the%20Numbers%20Game%20-%20Novel%20Multi-specific%20Therapeutics%20from%20a%20Diverse%20Collection%20of%20Human%20Domain%20Antibodies%20-%20Shelley%20Force%20Aldred.pdf.
Alexaki V-I., et al., "Adipocytes as Immune Cells: Differential Expression of Tweak, BAFF, and April and their Receptors (Fn14, BAFF-R, TACI and BCMA) at Different Stages of Normal and Pathological Adipose Tissue Development," The Journal of Immunology, 2009, vol. 183, pp. 5948-5956.
Ali S.A., et al., "T Cells Expressing an Anti-B-Cell Maturation Antigen Chimeric Antigen Receptor cause Remissions of Multiple Myeloma," Blood, Sep. 29, 2016, vol. 128, No. 13, pp. 1688-1700.
Almagro J.C., et al., "Identification of Differences in the Specificity-determining Residues of Antibodies That Recognize Antigens of Different Size: Implications for the Rational Design of Antibody Repertoires," Journal of Molecular Recognition, 2004, vol. 17, No. 2, pp. 132-143.
Amiri S.A., et al., "A Novel Anti-CD22 scFV-apoptin Fusion Protein Induces Apoptosis in Malignant B-cells," AMB Express, Dec. 2017, vol. 7, No. 1: 112, 11 Pages, ISSN 0004931985.
Anonymous, "Antibody Therapeutics—Teneobio's Next Generation of Multispecific Antibody Therapeutics," Drug Development and Delivery, Jan. 1, Feb. 2018, pp. 1-9, [Retrieved on Apr. 29, 2020] Retrieved from URL: https://drug-dev.com/antibody-therapeutics-teneobios-next-generation-of-multispecific-antibody-therapeutics/.
Anonymous: "Dose Escalation Study of Teclistamab, a Humanized BCMA*CD3 Bispecific Antibody, in Participants with Relapsed or Refractory Multiple Myeloma (MajesTEC-1)," National Institutes of Health, U.S. National Library of Medicine, ClinicalTrials.gov Identifier: NCT01314518, 2017, pp. 1-11, Retrieved from URL: https://www.clinicaltrials.gov/ct2/show/NCT03145181.
Anonymous: "SinoBiological Inc—Antibody-Catalogue," 2016, 150 Pages, Retrieved from URL: https://cdnl.sinobiological.com/reagent/catalogue/antibody-catalogue-EN.pdf.
Anonymous (TeneoBio, Inc.): "A Study of TNB-383B in Subjects with Relapsed or Refractory Multiple Myeloma," U.S National Library of Medicine, May 1, 2019, 8 Pages, Retrieved from URL: https://clinicaltrials.gov/ct2/show/NCT03933735/.
"Anti-BCMA (Human) (Vicky-1) (OAED00318)," Vicky-1 Datasheet , Aviva Systems Biology, cited on Feb. 24, 2023, in the EP Opposition for EP2780375, 2 Pages.
Armitage J.O., "A Clinical Evaluation of the International Lymphoma Study Group Classification of Non-Hodgkin's Lymphoma," Blood, Jun. 1, 1997, vol. 89, No. 11, pp. 3909-3918.
Armour K.L., et al., "Recombinant Human IgG Molecules Lacking Fcγ Receptor I Binding and Monocyte Triggering Activities," European Journal of Immunology, 1999, vol. 29, No. 8, pp. 2613-2624.
Arnett K.L., et al., "Crystal Structure of a Human CD3-ε/δ Dimer in Complex with a UCHT1 Single-chain Antibody Fragment," Proceedings of the National Academy of Sciences, U.S.A., Nov. 16, 2004, vol. 101, No. 46, pp. 16268-16273.
Baas T., "Superhuman Mice," Science-Business Exchange, 2014, vol. 7, No. 17, pp. 1-2, Published Online May 1, 2014, DOI:10.1038/scibx.2014.479, ISSN 1945-3477, XP055476407.
Baeuerle P.A., et al., "Bispecific T-Cell Engaging Antibodies for Cancer Therapy," Cancer Research, Jun. 15, 2009, vol. 69, No. 12, pp. 4941-4944.
Baeuerle P.A., et al., "BiTE: A New Class of Antibodies that Recruit T-cells," Drugs of the Future, 2008, vol. 33, No. 2, pp. 137-147.
Baeuerle P.A., et al., "BiTE: Teaching Antibodies to Engage T-cells for Cancer Therapy," Current Opinion in Molecular Therapeutics, 2009, vol. 11, No. 1, pp. 22-30, 9 Pages.
Banihashemi S.R., et al., "Development of Specific Nanobodies (VHH) for CD19 Immuno-Targeting of Human B-lymphocytes," Iranian Journal of Basic Medical Sciences, 2018, vol. 21, No. 5, pp. 455-464, 10 Pages.
Bargou R., et al., "Tumor Regression in Cancer Patients by Very Low Doses of a T Cell-Engaging Antibody," Science, Aug. 15, 2008, vol. 321, pp. 974-977.
"BCMA Antibody [Vicky-1]," Vicky-1 Datasheet, GeneTex, Cat. No. GTX17323, cited on Feb. 24, 2023, in the EP Opposition for EP2780375, 1 Page.
"BCMA Monoclonal Antibody (Vicky-1)," Invitrogen, Datasheet, Lot No. VD2967484, cited on Feb. 24, 2023 in the EP Opposition for EP2780375, 1 Page.
"BCMA Monoclonal Antibody (Vicky-1)," Vicky-1 Datasheet, Invitrogen, cited on Feb. 24, 2023, in the EP Opposition for EP2780375, 1 Page.
"BCMA/TNFRSF17 Antibody (Vicky-1)—BSA Free," Vicky-1 Datasheet, Novus Biologicals, cited on Feb. 24, 2023 in the EP Opposition for EP2780375, 3 Pages.
Beckman, et al., "Antibody Constructs in Cancer Therapy: Protein Engineering Strategies to Improve Exposure in Solid Tumors," Cancer, 2007, vol. 109, No. 2, pp. 170-179.
Bellucci R., et al., "Complete Response to Donor Lymphocyte Infusion in Multiple Myeloma is Associated with Antibody Responses to Highly Expressed Antigens," Blood, Jan. 15, 2004, vol. 103, No. 2, pp. 656-663.
Bellucci R., et al., "Complete Response to Donor Lymphocyte Infusion in Patients with Multiple Myeloma is Associated with Antibody Response to BCMA, a Plasma Cell Membrane Receptor," Journal of the American Society of Hematology, Blood, Nov. 16, 2003, vol. 102, No. 11, pp. 192a-193a, 3 Pages.
Bellucci R., et al., "Graft-versus-tumor Response in Patients with Multiple Myeloma is Associated with Antibody Response to BCMA, a Plasma-Cell Membrane Receptor," Blood, May 15, 2005, vol. 105, No. 10, pp. 3945-3950.
Biotechne: "Human BCMA/TNFRSF17 Antibody," MAB193 Data Sheet, R&D Systems, Last Revised Feb. 7, 2018, 1 Page.
Bluemel C., et al., "Epitope Distance to the Target Cell Membrane and Antigen Size Determine the Potency of T Cell-mediated Lysis by BiTE Antibodies Specific for a Large Melanoma Surface Antigen," Cancer Immunology, Immunotherapy, 2010, vol. 59, pp. 1197-1209, Published Online on Mar. 23, 2010.
Bodmer J-L., et al., "Review—The Molecular Architecture of the TNF Superfamily," Trends in Biochemical Sciences, Jan. 2002, vol. 27, No. 1, pp. 19-26.
Boesch A.W., et al., "Highly Parallel Characterization of IgG Fc Binding Interactions," mAbs, Publication data: Landes Bioscience, US, Jul.-Aug. 2014, vol. 6, No. 4, pp. 915-927, 14 Pages.

(56) References Cited

OTHER PUBLICATIONS

Borchmann P., et al., "Phase 1 Trial of the Novel Bispecific Molecule H22xKi-4 in Patients with Refractory Hodgkin Lymphoma," Blood, Nov. 1, 2002, vol. 100, No. 9, pp. 3101-3107.
Bossen C., et al., "BAFF, April and their Receptors: Structure, Function and Signaling," Seminars in Immunology, 2006, vol. 18, No. 5, pp. 263-275.
Bostrom, et al., "Improving Antibody Binding Affinity and Specificity for Therapeutic Development," Methods in Molecular Biology, 2009, vol. 525, pp. 353-376.
Brudno J.N., et al., "T Cells Genetically Modified to Express an Anti-B-Cell Maturation Antigen Chimeric Antigen Receptor Cause Remissions of Poor-Prognosis Relapsed Multiple Myeloma," Journal of Clinical Oncology, Aug. 1, 2018, vol. 36, No. 22, pp. 2267-2280, 16 Pages.
Bruggemann M., et al., "Heavy-Chain-Only Antibody Expression and B-Cell Development in the Mouse," Critical Reviews in Immunology, 2006, vol. 26, No. 5, pp. 377-390.
Bruggemann M., et al., "Human Antibody Production in Transgenic Animals," Archivum Immunologiae et Therapiae Experimentalis, Birkahaeser Verlag AG, 2015, vol. 63, No. 2, pp. 101-108, Published online on Dec. 3, 2014.
Buelow B., et al., "Development of a Fully Human T Cell Engaging Bispecific Antibody for the Treatment of Multiple Myeloma," Tenebio, Jun. 1, 2017, vol. 35 Supplement, No. 15, 8017 (Poster), 1 Page, DOI: 10.1200/JCO.2017.35.15_suppl.8017, ISSN 0732-183X, XP055476418, Retrieved from URL https://www.teneobio.com/wp-content/uploads/2017/06/poster.pdf.
Buelow B., et al., "Development of a Fully Human T-cell Engaging Bispecific Antibody for the Treatment of Multiple Myeloma," Journal of Clinical Oncology, Meeting Info: 2018 ASCO-SITC Clinical Immuno-Oncology Symposium, Feb. 10, 2018, vol. 36, No. 5_Supplement, Abstract No. 60, 3 Pages, Published Online on Feb. 26, 2018.
Buelow B., et al., "Effect of Modulation of Cd3 Binding in a Psmaxcd3 T-cell Engaging Bispecific Antibody on Maintenance of Efficient Tumor Cell Kill Cytokine Release," Journal of Clinical Oncology, 2020, vol. 38, No. 15, 4 Pages, Suppl. e17583, DOI: 10.1200/JC0.2020.38.15_suppl.e17583.
Buelow B., et al., "Evaluation of Monovalent Versus Biparatopic CD3xPSMA Bispecific Antibodies for Tcell Mediated Killing of Prostate Tumor Cells with Minimal Cytokine Release," Journal of Clinical Oncology, Meeting Info: Annual meeting of the American Society of Clinical Oncology, May 2019, vol. 37, No. 15_Supplement, Abstract No. e16519, 1 Page.
Buelow B., et al., "Pre-Clinical Development of TNB-383B, a Fully Human T-cell Engaging Bispecific Antibody Targeting BCMA for the Treatment of Multiple Myeloma," Journal of Clinical Oncology, May 20, 2018, vol. 36, No. 15_Supplement, Abstract No. 8034, pp. 1-4, Published Online on Jun. 1, 2018.
Buelow B., et al., "TNB383B.0001: A Multicenter, Phase 1, Open-Label, Dose-Escalation Andexpansion Study of TNB-383B, a Bispecific Antibodytargeting BCMA in Subjects with Relapsed or Refractorymultiple Myeloma," Blood, American Society of Hematology, US, Nov. 13, 2019, vol. 134, Supplement 1, p. 1874, 03 Pages, DOI: https://doi.org/10.1182/blood-2019-123220.
Buelow B., et al., "TNB585.001 : A Multicenter, Phase 1, Open-Label, Dose-Escalation and Expansion Study of TNB-585, a Bispecific T-Cell Engager Targeting PSMA in Subjects with Metastatic Castrate Resistant Prostate Cancer," Journal of Clinical Oncology, 2021, vol. 39, No. 15_Supplement, Abstract No. TPS5092, pp. 1-4, Published Online May 28, 2021, DOI:10.1200/JC0.2021.39.15_suppl.TPS5092.
Business Wire: "OMT Therapeutics Announces UniRatTM Alliance with Caltech," May 15, 2015, 1 Page, Retrieved from URL: http://www.businesswire.com/news/home/20150514006523/en/OMT-Therapeutics-Announces-UniRat(TM)-Alliance-Caltech.
Canfield S.M., et al., "The Binding Affinity of Human IgG for its High Affinity Fc Receptor Is Determined by Multiple Amino Acids in the CH2 Domain and Is Modulated by the Hinge Region," Journal of Experimental Medicine, Jun. 1991, vol. 173, pp. 1483-1491.
Caraccio C., et al., "Bispecific Antibodies for Multiple Myeloma: A Review of Targets, Drugs, Clinical Trials and Future Directions," Frontiers in Immunology, Published on Apr. 24, 2020, vol. 11, Article No. 501, pp. 1-25.
Carpenter R.O., et al., "B-cell Maturation Antigen Is a Promising Target for Adoptive T-cell Therapy of Multiple Myeloma," Clinical Cancer Research, the American Association for Cancer Research, US, Apr. 15, 2013, vol. 19, No. 8, pp. 2048-2060, Published Online on Jan. 23, 2013, DOI:10.1158/1078-0432.CCR-12-2422, ISSN 1078-0432, XP002727959.
CD3 Ortholog Alignment, Cited on Apr. 17, 2023 in the EP Opposition for EP2780375, 1 Page.
Chames P., et al., "Bispecific Antibodies for Cancer Therapy," Current Opinion in Drug Discovery & Development, 2009, vol. 12, No. 2, pp. 276-283.
Chames P., et al., "Bispecific Antibodies for Cancer Therapy: The light at the End of the Tunnel," mAbs, Nov./Dec. 2009, vol. 1, No. 6, pp. 539-547.
Chassaing B., et al., "Dextran Sulfate Sodium (DSS)-Inducted Colitis in Mice," Current Protocols in Immunology, Feb. 2014, Unit 15.25, Supplement 104, pp. 15.25.1-15.25.14.
Chatenoud L., et al., "CD3 Monoclonal Antibodies: A First Step Towards Operational Immune Tolerance in the Clinic," The Review of Diabetic Studies, 2012, vol. 9, No. 4, pp. 372-381.
Chen C., et al., "Enhancement and Destruction of Antibody Function by Somatic Mutation: Unequal Occurrence is Controlled by V Gene Combinatorial Associations," The EMBO Journal/European Molecular Biology Organization, IRL Press, Oxford, Jun. 15, 1995, vol. 14, No. 12, pp. 2784-2794.
Chen X., et al., "Fusion Protein Linkers: Property, Design and Functionality," Advanced Drug Delivery Reviews, Oct. 15, 2013, vol. 65, No. 10, pp. 1357-1369.
Cheung A., et al., "Targeting Folate Receptor Alpha for Cancer Treatment," Oncotarget, Aug. 9, 2016, vol. 7, No. 32, 22 pages.
Chini E.N., et al., "The Pharmacology of CD38/NADase: An Emerging Target in Cancer and Diseases of Aging," Trends in Pharmacological Sciences, Apr. 2018, vol. 39, No. 4, pp. 424-436.
Chiu A., et al., "Hodgkin Lymphoma Cells Express TACI and BCMA Receptors and Generate Survival and Proliferation Signals in Response to BAFF and April," Blood, Jan. 15, 2007, vol. 109, No. 2, pp. 729-739.
Chiu, et al., "A PSMA-Targeting CD3 Bispecific Antibody Induces Antitumor Responses that are Enhanced by 4-1BB Costimulation," Cancer Immunology Research, 2020, vol. 8, pp. 596-608.
Chiu M.L., et al., "Engineering Antibody Therapeutics," Current Opinion in Structural Biology, Science Direct, 2016, vol. 38, pp. 163-173.
Choi B.D., et al., "Bispecific Antibodies Engage T-cells for Antitumor Immunotherapy," Expert Opinion on Biological Therapy, Published Online: Mar. 30, 2011, vol. 11, No. 7, pp. 843-853, 12 Pages.
Chothia C., et al., "Canonical Structures for the Hypervariable Regions of Immunoglobulins," Journal of Molecular Biology, 1987, vol. 196, No. 4, pp. 901-917.
Chothia C., et al., "Conformations of Immunoglobulin Hypervariable Regions," Publication data: Cleo: Applications and Technology, 2019, San Jose, California, United States, May 5-10, 2019, Nature, Dec. 21, 1989, Optica, Source info: vol. 342, No. 6252, pp. 877-883.
Chou T-C., et al., "Quantitative Analysis of Dose-Effect Relationships: The Combined Effects of Multiple Drugs or Enzyme Inhibitors," Hopkins University School of Medicine, 1984, vol. 22, pp. 27-55.
Christian J.R., et al., "Measuring Bacterial Ectoenzyme Activities in Marine Waters Using Mercuric Chloride as a Preservative and a Control," Marine Ecology Progress Series, Published on Jul. 20, 1995, vol. 123, pp. 217-224.
Claim Set filed on Feb. 3, 2023, in EP Application No. 21183531.9, cited on Apr. 17, 2023 in the EP Opposition for EP2780375, 2 Pages.

(56) References Cited

OTHER PUBLICATIONS

Clarke S., et al., "A Novel CD3xPSMA Bispecific Antibody for Efficient T Cell Mediated Killing of Prostate Tumor Cells with Minimal Cytokine Release," Journal of Clinical Oncology, Genitourinary Cancers Symposium, Mar. 1, 2019, vol. 37, Supplement 7, Abstract No. 324, 03 Pages, DOI: 10.1200/JCO.2019.37.7_suppl. 324.
Clarke S., et al., "A Novel CD3xPSMA Bispecific Antibody for Efficient T Cell Mediated Killing of Prostate Tumor Cells with Minimal Cytokine Release," Journal of Clinical Oncology, Mar. 2019, vol. 37, Supplement 7, Abstract No. 324, 01 Page, DOI: 10.1200/JCO.2019.37.7_suppl.324.
Clarke S.C., et al., "Multispecific Antibody Development Platform Based on Human Heavy Chain Antibodies," Frontiers in Immunology, Frontiers Research Foundation, CH, Jan. 1, 2018, vol. 9, Article No. 3037, pp. 1-13, Published on Jan. 7, 2019, DOI:10.3389/FIMMU. 2018.03037, ISSN 1664-3224, XP009512208.
Clayton L.K., et al., "CD3 Eta and CD3 Zeta are Alternatively Spliced Products of a Common Genetic Locus and are Transcriptionally and/or Post-Transcriptionally Regulated During T-cell Development," Proceedings of the National Academy of Sciences, USA, Jun. 1991, vol. 88, pp. 5202-5206.
clinicaltrials.gov: "A Study of AMG 340 in Subjects with Metastatic Castrate-Resistant Prostate Carcinoma," Clinicaltrials Identifier: NCT04740034, 2021, pp. 1-8.
clinicaltrials.gov: "Study of CC-93269, a BCMA x CD3 T Cell Engaging Antibody, in Participants With Relapsed and Refectory Multiple Myeloma," ID: NCT03486067, 2022, 3 Pages.
Clynes R., et al., "Fc Receptors are Required in Passive and Active Immunity to Melanoma," Proceedings of the National Academy of Sciences, USA, Jan. 1998, vol. 95, No. 2, pp. 652-656.
Colman P.M., "Effects of Amino Acid Sequence Changes on Antibody-antigen Interactions," Publication data: Research in Immunology, Editions Scientifiques et Medicales Elsevier, FR, Jan. 1, 1994, vol. 145, No. 1, pp. 33-36.
Concepcion J., et al., "Label-Free Detection of Biomolecular Interactions Using BioLayer Interferometry for Kinetic Characterization," Combinatorial Chemistry & High Throughput Screening, 2009, vol. 12, No. 8, pp. 791-800.
Certificate of Compliance for Vicky-1 Antibody from Abcam, Cited on Feb. 24, 2023 in the EP Opposition for EP2780375, 1 Page.
Crescioli S., et al., "IgG4 Characteristics and Functions in Cancer Immunity," Current Allergy and Asthma Reports, Published Online on Jan. 7, 2016, vol. 16: 7, pp. 1-11.
"Crystal Structure and Protein Interaction Analysis for AMG 701 scFv-BCMA," cited on Feb. 24, 2023 in the EP Opposition for EP2780375, 3 Pages.
Cui X., et al., "Targeted Integration in Rat and Mouse Embryos with Zinc-Finger Nucleases," Nature Biotechnology, Jan. 2011, vol. 29, No. 1, pp. 64-67, 5 Pages.
Dai H., et al., "Chimeric Antigen Receptors Modified T-Cells for Cancer Therapy," JNCI: Journal of the National Cancer Institute, First Published Online on Jan. 27, 2016, vol. 108, No. 7: dJv439, pp. 1-14.
Dang K., et al., "Attenuating CD3 Affinity in a PSMAxCD3 Bispecific Antibody Enables Killing of Prostate Tumor Cells with Reduced Cytokine Release," Journal for Immuno Therapy of Cancer, 2021, vol. 9: e002488, pp. 1-14.
Dasilva J., "Abstract 34: A MET x MET Bispecific Antibody that Induces Receptor Degradation Potently Inhibits the Growth of MET-addicted Tumor Xenografts," American Association for Cancer Research, Cancer Research Annual Meeting, Apr. 1-5, 2017, vol. 77, No. 13_Supplement, Abstract No. 34, 2 Pages, Published on Jul. 2017.
Davies, et al., "Affinity Improvement of Single Antibody VH Domains: Residues in All Three Hypervariable Regions Affect Antigen Binding," Immunotechnology, 1996, vol. 2, No. 3, pp. 169-179.
Declaration of Dr. Christine E. Tinberg in EP 2780375 Opposition, EP Application No. 12805432.7, 2 Pages.
Declaration of Dr. Frank Mortari in EP 2780375 Opposition, EP Application No. 12805432.7, 7 Pages.
Declaration of Dr. Oliver Donze in EP 2780375 Opposition, EP Application No. 12805432.7, 28 Pages.
Declaration of Dr. Rui Zhu in EP Opposition No. 2780375 for EP Application No. 12805432.7 dated Jun. 9, 2020, 34 Pages.
Declaration of Kara Olson in EP Opposition No. 2780375 for EP Application No. 12805432.7 dated May 14, 2021, 5 Pages.
Declaration of Kevin C. Lindquist in EP Opposition No. 2780375 for EP Application No. 12805432.7 dated Jun. 9, 2020, 03 Pages.
Declaration of Nathan D. Trinklein, Ph.D, in EP Opposition No. 2780375 for EP Application No. 12805432.7, dated Jun. 8, 2020, 22 Pages.
Desmyter A., et al., "Antigen Specificity and High Affinity Binding Provided by One Single Loop of a Camel Single-Domain Antibody," The Journal of Biological Chemistry, the American Society for Biochemistry and Molecular Biology, Jul. 13, 2001, vol. 276, No. 28, pp. 26285-26290, DOI:10.1074/JBC.M102107200, ISSN 0021-9258, XP002190005, Published Online on May 7, 2001.
Dilillo D.J., et al., "A BCMAxCD3 Bispecific T Cell-Engaging Antibody Demonstrates Robust Antitumor Efficacy Similar to that of Anti-BCMA CAR T Cells," Blood Advances, Mar. 9, 2021, vol. 5, No. 5, pp. 1291-1304, Published Online on Mar. 2, 2021.
Dillon S.R., et al., "An April to Remember: Novel TNF Ligands as Therapeutic Targets," Nature Reviews Drug Discovery, Mar. 2006, vol. 5, No. 3, pp. 235-246, Published online on Feb. 10, 2006.
Dimopoulos M.A., et al., "Daratumumab, Lenalidomide, and Dexamethasone for Multiple Myeloma," The New England Journal of Medicine, Oct. 6, 2016, vol. 375, No. 14, pp. 1319-1331.
Dipippo, et al., "Efficacy Studies of an Antibody-Drug Conjugate PSMA-ADC in Patient-Derived Prostate Cancer Xenografts," Prostate, 2015, vol. 75, pp. 303-313, DOI: 10.1002/pros.22916.
Dondelinger M., et al., "Understanding the Significance and Implications of Antibody Numbering and Antigen-Binding Surface/Residue Definition," Frontiers in Immunology, Oct. 16, 2018, vol. 9, pp. 1-15, DOI:10.3389/fimmu.2018.02278, XP055572450.
Dong D., et al., "Structural Basis of Assembly of the Human T Cell Receptor—CD3 Complex," Nature, Sep. 26, 2019, vol. 573, pp. 546-552, 21 Pages.
Dooley H., et al., "Selection and Characterization of Naturally Occurring Single-Domain (IgNAR) Antibody Fragments from Immunized Sharks by Phage Display," Molecular Immunology, 2003, vol. 40, No. 1, pp. 25-33.
Duncan A.R., et al., "Localization of the Binding Site for the Human High-Affinity Fc Receptor on IgG," Nature, Apr. 7, 1988, vol. 332, p. 563, 2 Pages.
Durben M., et al., "Characterization of a Bispecific FLT3 X CD3 Antibody in an Improved, Recombinant Format for the Treatment of Leukemia," Molecular Therapy, Apr. 2015, vol. 23, No. 4, pp. 648-655, Published online on Feb. 3, 2015.
Enzo Life Sciences: "BCMA (Vicky-1): ALX-804-151 Product Datasheet," Last Revised on Dec. 20, 2019, 3 Pages.
"Epitope Mapping of A2J, E2M, H2C, F12Q, H1E, F70, 12C, F6A, G4H Antibodies," Cited on Apr. 17, 2023 in the EP Opposition for EP2780375, Feb. 28, 2017, 4 Pages.
"Sequence Alignment Macaque CD3 Epsilon and SEQ ID Nos. 2, 4, 6, and 8 of D14," Macaque CD3 Epsilon Sequence, 1 Page, Retrieved from URL: https://www.uniprot.Org/uniprotkb/Q95LI5/entry#sequences.
"Sequence Alignment of BCMA Extracellular Domain; Human, Rhesus Macaque," in the EP Opposition for EP2780375, cited on Jun. 12, 2020, 1 page.
"Sequence Alignment of CD3 Epsilon N-term, aa1-27; Human, Crab-eating Macaque, Rhesus Macaque," cited on Jun. 12, 2020 in the EP Opposition for EP2780375, 1 Page.
Excerpt of the WHO "Proposed INN List 123," Referring to Pacanalotamab Entitled, "International Nonproprietary Names for Pharmaceutical Substances (INN)," WHO Drug Information, 2020, vol. 34, No. 2, 5 Pages.
Faraji F., et al., "Development and Characterization of a Camelid Single-domain Antibody Directed to Human CD22 Biomarker," Biotechnology and Applied Biochemistry, Sep. 2018, vol. 65, No. 5, pp. 718-725, 2 Pages. (Abstract only).

(56) References Cited

OTHER PUBLICATIONS

Fitzgerald K.A., et al., "The Cytokine Facts Book," Second Edition, Academic Press, Sep. 18, 2001, pp. 151-152, 5 Pages.
Foote J., et al., "Antibody Framework Residues Affecting the Conformation of the Hypervariable Loops," Journal of Molecular Biology, 1992, vol. 224, No. 2, pp. 487-499.
Frenken L.G.J., et al., "Isolation of Antigen Specific Llama V.HH Antibody Fragments and Their High Level Secretion by *Saccharomyces cerevisiae*," Journal of Biotechnology, 2000, vol. 78, pp. 11-21.
Fry T.J., et al., "CD22-Targeted CART Cells Induce Remission in B-ALL that is Naive or Resistant to CD19-targeted CAR Immunotherapy," Nature Medicine, Jan. 2018, vol. 24, No. 1, pp. 20-28, 15 Pages.
Fujimori K., et al., "A Modeling Analysis of Monoclonal Antibody Percolation Through Tumors: A Binding-Site Barrier," Journal of Nuclear Medicine, 1990, vol. 31, No. 7, pp. 1191-1198.
Gazzano-Santoro H., et al., "A Non-Radioactive Complement-Dependent Cytotoxicity Assay for Anti-CD20 Monoclonal Antibody," Journal of Immunological Methods, 1996, vol. 202, No. 2, pp. 163-171.
GenBank: "*Homo sapiens* CD3e Molecule (CD3E), mRNA," Nucleotide-NCBI, GenBank Accession No. NM 000733, Jun. 8, 2019, pp. 1-4, Last visited on Apr. 23, 2020, Retrieved from URL: https://www.ncbi.nlm.nih.gov/nuccore/NM_000733.3.
GenBank: "*Homo sapiens* gene for BCMA, complete CDS," GenBank Accession No. AB052772.1, pp. 1-3 [Retrieved on Apr. 23, 2020] Retrieved from URL: https://www.ncbi.nlm.nih.gov/nuccore/AB052772.
Gershoni J.M ., et al., "Epitope Mapping—The First Step in Developing Epitope-Based Vaccines," Biodrugs, Adis International Limited, New Zealand, Jan. 1, 2007, vol. 21, No. 3, pp. 145-156, DOI: 10.2165/00063030-200721030-00002, ISSN 1173-8804, XP009103541.
Geurts A.M., et al., "Knockout Rats via Embryo Microinjection of Zinc-finger Nucleases," Science, Jul. 24, 2009, vol. 325, No. 5939, pp. 433, 2 Pages.
Ghahroudi M.A., et al., "Selection and Identification of Single Domain Antibody Fragments From Camel Heavy-chain Antibodies," FEBS Letters, 1997, vol. 414, No. 3, pp. 521-526.
Giavridis T., et al., "CAR T Cell-Induced Cytokine Release Syndrome is Mediated by Macrophages and Abated by IL-1 Blockade," Nature Medicine, Jun. 2018, vol. 24, pp. 731-738, 14 Pages.
Glennie M.J., et al., "Preparation and Performance of Bispecific F(Ab' Gamma)2 Antibody Containing Thioether-linked Fab' Gamma Fragments," Journal of Immunology, 1987, vol. 139, No. 7, pp. 2367-2375.
Goel M., et al., "Plasticity Within the Antigen-combining Site May Manifest as Molecular Mimicry in the Humoral Immune Response," The Journal of Immunology, Dec. 15, 2004, vol. 173, No. 12, pp. 7358-7367.
Goldstein R.L., et al., "AMG 701 Induces Cytotoxicity of Multiple Myeloma Cells and Depletes Plasma Cells in Cynomolgus Monkeys," Blood Advances, Sep. 8, 2020, vol. 4, No. 17:B1, pp. 4180-4194, 15 Pages.
Gonzales, et al., "Minimizing The Immunogenicity of Antibodies for Clinical Application," Tumor Biology, 2005, vol. 26, No. 1, pp. 31-43.
Gras M-P., et al., "BCMA: An Integral Membrane Protein in the Golgi Apparatus of Human Mature B Lymphocytes," International Immunology, 1995, vol. 7, pp. 1093-1106.
Gruss H.J., et al., "Structural and Biological Features of the TNF Receptor and TNF Ligand Superfamilies: Interactive Signals in the Pathobiology of Hodgkin's Disease," Annals of Oncology, 1996, vol. 7, Suppl. 4, pp. 19-26.
Gupta K.K., et al., "Constitutive Inflammatory Cytokine Storm: A Major Threat to Human Health," Journal of Interferon & Cytokine Research, 2019, vol. 40, No. 1 , pp. 19-23.
Gust J., et al., "Endothelial Activation and Blood-Brain Barrier Disruption in Neurotoxicity After Adoptive Immunotherapy With CD19 CAR-T Cells," Cancer Discovery, 2017, vol. 7, No. 12, pp. 1405-1419, 17 Pages.
Guy C.S., et al., "Organization of Proximal Signal Initiation at the TCR:CD3 Complex," Immunological Reviews, Nov. 2009, vol. 232, No. 1, pp. 1-22.
Haffner C.D., et al., "Discovery, Synthesis, and Biological Evaluation of Thiazoloquin(az)olin(on)es as Potent CD38 Inhibitors," Journal of Medical Chemistry, 2015, vol. 58, No. 8, pp. 3548-3571.
Hagner P.R., et al., "Targeting B-cell Maturation Antigen (BCMA) With CC-93269, a $2_{+}1$ T Cell Engager, Elicits Significant Apoptosis in Diffuse Large B-cell Lymphoma Preclinical Models," Blood, Nov. 13, 2019, vol. 134, p. 1580, 3 Pages.
Hamers-Casterman C., et al., "Naturally Occurring Antibodies Devoid of Light Chains," Nature, 1993, vol. 363, pp. 446-448.
Hamilon S.R., et al., "Humanization of Yeast to Produce Complex Terminally Sialylated Glycoproteins," Science, Sep. 8, 2006, vol. 313, No. 5792, pp. 1441-1443.
Hanes J., et al., "New Advances in Microsphere-Based Single-Dose Vaccines," Advanced Drug Delivery Reviews, 1997, vol. 28, No. 1, pp. 97-119.
Harris, et al., "Sequence-Based Discovery Demonstrates that Fixed Light Chain Human Transgenic Rats Produce a Diverse Repertoire of Antigen-specific Antibodies," Frontiers in Immunology, 2018, vol. 9, No. 889, DOI:10.3389/fimmu.2018.00889.
Harris, et al., "Lymphoma Classification—from Controversy to Consensus: The R.E.A.L. and WHO Classification of Lymphoid Neoplasms," Annals of Oncology, 2000, vol. 11, Supplement 1, pp. S3-S10.
Hassani M., et al., "Construction of a Chimeric Antigen Receptor Bearing a Nanobody Against Prostate a Specific Membrane Antigen in Prostate Cancer," Journal of Cellular Biochemistry, Jan. 22, 2019, vol. 120, No. 6, pp. 10787-10795, DOI:10.1002/jcb.28370, ISSN 0730-2312, XP055696932.
Hassanzadeh-Ghassabeh G., et al., "Nanobodies and their Potential Applications," Nanomedicine, 2013, vol. 8, No. 6, pp. 1013-1023, 14 Pages.
Hermans I.F., et al., " The Vital Assay: A Versatile Fluorometric Technique for Assessing CTL- and NKT-mediated Cytotoxicity Against Multiple Targets in Vitro and in Vivo," The Journal of Immunology Methods, 2004, vol. 285, No. 1, pp. 25-40.
Hernandez-Hoyos G., et al., "MOR209/ES414, a Novel Bispecific Antibody Targeting PSMA for the Treatment of Metastatic Castration-Resistant Prostate Cancer," Molecular Cancer Therapeutics, 2016, vol. 15, No. 9, pp. 2155-2165.
Hipp S., et al., "A Novel BCMA/CD3 Bispecific T-cell Engager for the Treatment of Multiple Myeloma Induces Selective Lysis in Vitro and in Vivo," Leukemia, US, Dec. 27, 2016, vol. 31, No. 8, pp. 1743-1751, DOI:10.1038/leu.2016.388, ISSN 0887-6924, XP055547607.
Hlavacek W.S., et al., "Steric Effects on Multivalent Ligand-receptor Binding: Exclusion of Ligand Sites by Bound Cell Surface Receptors," Biophysical Journal, Jun. 1999, vol. 76, No. 6, pp. 3031-3043.
Hofman M.S., et al., "[177Lu]-PSMA-617 Radionuclide Treatment in Patients with Metastatic Castration-Resistant Prostate Cancer (LuPSMA Trial): A Single-Centre Single-Arm, Phase 2 Study," The Lancet Oncology, 2018, vol. 19, No. 6, pp. 825-833.
Honegger A., et al., "Yet Another Numbering Scheme for Immunoglobulin Variable Domains: An Automatic Modeling and Analysis Tool," Journal of Molecular Biology, Jun. 8, 2001, vol. 309, No. 3, pp. 657-670, DOI: 10.1006/jmbi.2001.4662, XP004626893.
Honemann D., et al., "A Novel Recombinant Bispecific Single-Chain Antibody, bscWue-1 x CD3, Induces T-Cell-Mediated Cytotoxicity Towards Human Multiple Myeloma Cells," Leukemia, vol. 18, No. 3, Jan. 22, 2004, pp. 636-644.
Hotzel I., et al., "A Strategy for Risk Mitigation of Antibodies with Fast Clearance," mABs, 2012, vol. 4, No. 6, pp. 753-760, 26 Pages.
Huang C.J., et al., "Recombinant Immunotherapeutics: Current State and Perspectives Regarding the Feasibility and Market," Applied Microbiology and Biotechnology, 2010, vol. 87, pp. 401-410.

(56) References Cited

OTHER PUBLICATIONS

Hymowitz S.G., et al., "Structures of April-Receptor Complexes: Like BCMA, TACI Employs Only a Single Cysteine-Rich Domain for High Affinity Ligand Binding," The Journal of Biological Chemistry, Feb. 25, 2005, vol. 280, No. 8, pp. 7218-7227, 18 Pages. (Supplementary Material).
Imai-Nishiya H., et al., "Double Knockdown of α 1, 6-fucosyltransferase (FUT8) and GDP-mannose 4,6-dehydratase (GMD) in Antibody-producing Cells: A New Strategy for Generating Fully Non-fucosylated Therapeutic Antibodies with Enhanced ADCC," BMC Biotechnology, Nov. 30, 2007, vol. 7, No. 84, pp. 1-13.
In-house data from the Proprietors showing the KO of E1/E4-BCMA/CD3 bispecific antibodies and E3-BCMA/CD3 bispecific antibodies, entitled, "Affinities of BCMA/CD3 Bispecific Binding Molecules According to the Patent" 1 Page.
International Myeloma Society: "Bringing Together Clinical and Experimental Scientists Involved in the Study of Myeloma," Conference Abstracts of the International Myeloma Society, 19th Annual Meeting and Exposition, Los Angeles, California, Aug. 25-27, 2022, 222 Pages.
Ippoliti G., et al., "Immunomodulation with Rabbit Anti-Thymocyte Globulin in Solid Organ Transplantation," World Journal of Transplantation, Dec. 24, 2015, vol. 5, No. 4, pp. 261-266.
Iri-Sofla F.J., et al., "Nanobody-Based Chimeric Receptor Gene Integration in Jurkat Cells Mediated by Phic31 Integrase," Experimental Cell Research, 2011, vol. 317, No. 18, pp. 2630-2641.
Jabbour E., et al., "Monoclonal Antibodies in Acute Lymphoblastic Leukemia," Blood, Jun. 25, 2015, vol. 125, No. 26, pp. 4010-4016.
Jackson H.J., et al., "Driving CAR T-Cells Forward," Nature Reviews, Clinical Oncology, Jun. 2016, vol. 13, No. 6, pp. 370-383.
Jamnani F.R., et al., "T Cells Expressing VHH-Directed Oligoclonal Chimeric Her2 Antigen Receptors: Towards Tumor-directed Oligoclonal T Cell Therapy," Biochimica et Biophysica Acta (BBA)—General Subjects, 2014, vol. 1840, No. 1, pp. 378-386.
Janeway C.A. Jr., et al., "Antigen Receptor Structure and Signaling Pathways," Figure 6.8, Immunobiology: The Immune System in Health and Disease, 5th Edition, New York: Garland Science, 2001, p. 01.
Janssens R., et al., "Generation of Heavy-Chain-Only Antibodies in Mice," Proceedings of the National Academy of Sciences of the USA, Oct. 10, 2006, vol. 103, No. 41, pp. 15130-15135.
Jaton J-C., et al., "Recovery of Antibody Activity Upon Reoxidation of Completely Reduced Polyalanyl Heavy Chain and its Fd Fragment Derived from Anti-2,4-dinitrophenyl Antibody," Biochemistry, Dec. 1968, vol. 7, No. 12, pp. 4185-4195.
Jemal A., et al., "Cancer Statistics, 2008," ACS Journals, CA a Cancer Journal of Clinicians, Mar./Apr. 2008, vol. 58, No. 2, pp. 71-96, 27 Pages.
Jiang C., et al., "B Cell Maturation Antigen Deficiency Exacerbates Lymphoproliferation and Autoimmunity in Murine Lupus," The Journal of Immunology, 2011, vol. 186, No. 11, pp. 6136-6147.
Jones A.J.S., "Analysis of Polypeptides and Proteins," Advanced Drug Delivery Reviews, 1993, vol. 10, No. 1, pp. 29-90.
Jones P.T., et al., "Replacing the Complementarity-determining Regions in a Human Antibody with Those from a Mouse," 1986, Nature vol. 321:522-525.
Kabat E.A., et al., "Sequences of Proteins of Immunological Interest," Bethesda, MD : U.S. Dept. of Health and Human Services, Public Health Service, National Institutes of Health, 1991, vol. 1, p. 310, 45 Pages, Retrieved from URL: https://books.google.co.uk/booksid=3jMvZYW2ZtwC&lpg=PA1137-IA1&pg=PP1#v=onepage&q&f=false.
Kalled S.L., "The Role of BAFF in Immune Function and Implications for Autoimmunity," Immunological Reviews, 2005, vol. 204, No. 1, pp. 43-54.
Kanda Y., et al., "Establishment of a GDP-Mannose 4,6-Dehydratase (GMD) Knockout Host Cell Line: A New Strategy for Generating Completely Non-Fucosylated Recombinant Therapeutics," Journal of Biotechnology, 2007, vol. 139, pp. 300-310.
Kaneko Y., et al., "Anti-Inflammatory Activity of Immunoglobulin G Resulting from Fc Sialylation," Science, Aug. 4, 2006, vol. 313, No. 5787, pp. 670-673.
Kapoor P., et al., "Anti-CD20 Monoclonal Antibody Therapy in Multiple Myeloma," British Journal of Haematology, 2008, vol. 141, No. 2, pp. 135-148.
Kershaw M.H., et al., "A Phase I Study on Adoptive Immunotherapy Using Gene-Modified T Cells for Ovarian Cancer," Clinical Cancer Research, 2006, vol. 12, No. 20, pp. 6106-6115.
Kim D.Y., et al., "Mutational Approaches to Improve the Biophysical Properties of Human Single-Domain Antibodies," Biochimica et Biophysica Acta (BBA), Proteins & Proteomics, Elsevier, Netherlands, 2014, vol. 1844, No. 11, pp. 1983-2001, 19 Pages.
Kim J.M., et al., "Novel Antibodies Targeting MUC1-C Showed Anti-Metastasis and Growth-Inhibitory Effects on Human Breast Cancer Cells," May 5, 2020, XP055934458, [Retrieved on Jun. 22, 2022] Retrieved from the Internet URL: https://www.ncbi.nlm.nih.gov/pmc/articles/PMC7247325/pdf/ijms-21-03258.pdf.
Kishimoto H., et al., "Physical Dissociation of the TCR-CD3 Complex Accompanies Receptor Ligation," Journal of Experimental Medicine, Dec. 1995, vol. 182, pp. 1997-2006.
Kitagawa H., et al., "Differential Expression of Five Sialyltransferase Genes in Human Tissues," The Journal of Biological Chemistry, Jul. 8, 1994, vol. 269, No. 27, pp. 17872-17878, 08 Pages.
Kjer-Nielsen L., et al., "Crystal Structure of the Human T Cell Receptor CD3EY Heterodimer Complexed to the Therapeutic mAb OKT3," Proceedings of the National Academy of Sciences, May 18, 2004, vol. 101, No. 20, pp. 7675-7680.
Koarada S., et al., "Autoantibody-Producing RP105-B Cells, from Patients with Systematic Lupus Erythematosus, Showed more Preferential Expression of BCMA Compared with BAFF-R than Normal Subjects," Rheumatology, Jan. 22, 2010, vol. 49, No. 4, pp. 662-670.
Kochenderfer J.N., et al., "Construction and Pre-Clinical Evaluation of an Anti-CD19 Chimeric Antigen Receptor," Journal of Immunotherapy, Sep. 2009, vol. 32, No. 7, pp. 689-702, 26 Pages.
Kohler G., et al., "Pillars Article: Continuous Cultures of Fused Cells Secreting Antibody of Predefined Specificity," Nature, Aug. 7, 1975, vol. 256, No. 5517, pp. 495-497.
Koide, et al., "Exploring the Capacity of Minimalist Protein Interfaces: Interface Energetics and Affinity Maturation to Picomolar KD of a Single-domain Antibody with a Flat Paratope," Journal of Molecular Biology, vol. 373, No. 4, pp. 941-953.
Kontermann R.E., "Bispecific Antibodies: Developments and Current Perspectives," Springer-Verlag, Berlin, Heidelberg, Chapters 1, 2, 7, 11, 13, 14, and 15, 2011, 151 Pages.
Kontermann R.E., "Invited Review—Recombinant Bispecific Antibodies for Cancer Therapy," Acta Pharmacologica Sinica, Jan. 2005, vol. 26, No. 1, pp. 1-9.
Kufer P., et al., "Review—A Revival of Bispecific Antibodies," Trends in Biotechnology, May 2004, vol. 22, No. 5, pp. 238-244.
Kuhns M.S., et al., "Deconstructing the Form and Function of the TCR/CD3 Complex," Immunity, 2006, vol. 24, No. 2, pp. 133-139.
Kumar S., et al., "International Myeloma Working Group Consensus Criteria for Response and Minimal Residual Disease Assessment in Multiple Myeloma," The Lancet. Oncology, Aug. 2016, vol. 17, No. 8, pp. e328-e346.
Kumar S.K., et al., "Improved Survival in Multiple Myeloma and the Impact of Novel Therapies," Blood, Mar. 1, 2008, vol. 111, No. 5, pp. 2516-2520.
Kunik V., et al., "Structural Consensus among Antibodies Defines the Antigen Binding Site," PLOS Computational Biology, 2012, vol. 8, No. 2, e1002388, pp. 1-12.
Kurosaki A., et al., "Serum Folate Receptor Alpha as a Biomarker for Ovarian Cancer: Implications for Diagnosis, Prognosis and Predicting Its Local Tumor Expression," International Journal of Cancer, Malden, Mass : Wiley-Blackwell, US, Apr. 15, 2016, vol. 138, No. 8, pp. 1994-2002.
Kussie P.H., et al., "A Single Engineered Amino Acid Substitution Changes Antibody Fine Specificity," The Journal of Immunology, Jan. 1, 1994, vol. 152, No. 1, pp. 146-152.
Kuznetsova I.M, et al., "Structural Dynamics, Stability and Folding of Proteins," Tsitologiya, 2005, vol. 47, No. 11, pp. 943-952.

(56) References Cited

OTHER PUBLICATIONS

Laabi Y., et al., "A New Gene, BCM, on Chromosome 16 is Fused to the Interleukin 2 Gene by a t(4;16)(q26;p13) Translocation in a Malignant T Cell Lymphoma," The EMBO Journal, 1992, vol. 11, No. 11, pp. 3897-3904.
Laabi Y., et al., "The BCMA Gene, Preferentially Expressed During B lymphoid Maturation, is Bidirectionally Transcribed," Nucleic Acids Research, 1994, vol. 22, No. 7, pp. 1147-1154.
Labome: "Product Summary for Cd3e Monoclonal Antibody (SPV-T3b)," Dec. 22, 2022, vol. 15, No. 48, 4 Pages, Retrieved from URL: https://www.labome.com/product/Invitrogen/07-0303.html.
Labrijn A.F., et al., "Bispecific Antibodies: A Mechanistic Review of the Pipeline," Nature Reviews, Drug Discovery, Aug. 2019, vol. 18, No. 8, pp. 585-608.
Labrijn A.F., et al., "Therapeutic IgG4 Antibodies Engage in Fab-arm Exchange With Endogenous Human IgG4 in Vivo," Nature Biotechnology, Aug. 2009, vol. 27, No. 8, pp. 767-771, 7 Pages.
Langer R., "New Methods of Drug Delivery," Science, Sep. 28, 1990, vol. 249, No. 4976, pp. 1527-1533.
Lee E.U., et al., "Alteration of Terminal Glycosylation Sequences on N-Linked Oligosaccharides of Chinese Hamster Ovary Cells by Expression of 0β-Galactoside α2,6-Sialytransferase," The Journal of Biological Chemistry, Aug. 15, 1989, vol. 264, No. 23, pp. 13848-13855.
Lee S-M., et al., "Cell to Cell Interaction Can Activate Membrane-bound April Which Are Expressed on Inflammatory Macrophages," Immune Network, Oct. 2010, vol. 10, No. 5, pp. 173-180.
Lefranc M-P., et al., "IMGT, the International ImMunoGeneTics Database," Nucleic Acids Research, Oxford University Press, 2001, vol. 29, No. 1, pp. 207-209.
Lefranc M-P., et al., "The Immunoglobulin FactsBook," Academic Press, 2001, 473 Pages.
Leiba M., et al., "Activation of B Cell Maturation Antigen (BCMA) on Human Multiple Myeloma Cells by a Proliferation-Inducing Ligand (April) Promotes Myeloma Cell Function in the Bone Marrow Microenvironment," Blood, Nov. 16, 2007, vol. 110, No. 11: 1503, 2 Pages.
Leow C.H., et al., "Single Domain Antibodies as New Biomarker Detectors," Diagnostics, Oct. 17, 2017, vol. 7, No. 4: 52, 34 Pages.
Leung F., et al., "Folate-Receptor 1 (FOLR1) Protein is Elevated in the Serum of Ovarian Cancer Patients," Clinical Biochemistry, Elsevier, Amsterdam, NL, Mar. 23, 2013, vol. 46, No. 15, pp. 1462-1468.
Levine S.J., "Mechanisms of Soluble Cytokine Generation," Journal of Immunology, 2004, vol. 173, No. 9, pp. 5343-5348, 7 Pages.
Lindhofer H., et al., "Preferential Species-Restricted Heavy/Light Chain Pairing in Rat/Mouse Quadromas. Implications for a Single-step Purification of Bispecific Antibodies," The Journal of Immunology, 1995, vol. 155, No. 1, pp. 219-225.
Link B.K., et al., "Anti-CD3-Based Bispecific Antibody Designed for Therapy of Human B-Cell Malignancy can Induce T-cell Activation by Antigen-dependent and Antigen-independent Mechanisms," International journal of Cancer Research, 1998, vol. 77, pp. 251-256.
Liu., et al., "Method for Preparing Bispecific Monoclonal Antibodies," Chinese Animal Husbandry and Veterinary Medicine, vol. 34, pp. 49-52.
Liu J.L., et al., "Selection and Characterization of Single Domain Antibodies against Human CD20," Molecular Immunology, GB, Oct. 1, 2016, vol. 78, pp. 146-154, DOI:10.1016/j.molimm.2016.09.013, ISSN 0161-5890, XP055363485.
Liu Y., et al., "Ligand-Receptor Binding Revealed by the TNF Family Member TALL-1," Nature, May 1, 2003, vol. 423, No. 6935, pp. 49-56, 10 Pages.
Liu Z., et al., "Asymmetrical FC Engineering Greatly Enhances Antibody-dependent Cellular Cytotoxicity (ADCC) Effector Function and Stability of the Modified Antibodies," Journal of Biological Chemistry, Feb. 7, 2014, vol. 289, No. 6, pp. 3571-3590.
Lloyd C., et al., "Modelling the Human Immune Response: Performance of a 1011 Human Antibody Repertoire Against a Broad Panel of Therapeutically Relevant Antigens," Protein Engineering, Design & Selection, 2009, vol. 22, No. 3, pp. 159-168.
Lokhorst H.M., et al., "Targeting CD38 with Daratumumab Monotherapy in Multiple Myeloma," The New England Journal of Medicine, 2015, vol. 373, No. 13, pp. 1207-1219, 5 Pages.
Lorentsen K., et al., "Uncoupling Tumor-cell Cytotoxicity From Cytokine Release With Novel T-cell Engaging Bispecific Antibodies," Meeting Info: American Association for Cancer Research Annual Meeting, Cancer Research, 2019, vol. 79, No. 13 (Suppl), Abstract 1554, 1 Page.
Lund J., et al., "Expression and Characterization of Truncated Forms of Humanized L243 IgG1, Architectural Features can Influence Synthesis of its Oligosaccharide Chains and Affect Superoxide Production Triggered Through Human Fcγ Receptor 1," European journal of biochemistry, 2000, vol. 267, pp. 7246-7256.
Mack M., et al., "A Small Bispecific Antibody Construct Expressed as a Functional Single-chain Molecule with High Tumor Cell Cytotoxicity," Proceedings of the National Academy of Sciences, Jul. 1995, vol. 92, pp. 7021-7025.
Mackay F., et al., "BAFF and April: A Tutorial on B Cell Survival," Annual Review of Immunology, 2003, vol. 21, No. 1, pp. 231-264, 36 Pages.
Mailankody S., et al., "T-Cell Engagers—Modern Immune-Based Therapies for Multiple Myeloma," The New England Journal of Medicine, Aug. 11, 2022, vol. 387, No. 6, pp. 558-561.
Malik H., et al., "A Novel Fully Human Bispecific CD19 x CD3 Antibody that Kills Lymphoma Cells with Minimal Cytokine Secretion," American Society of Hematology, Blood, US, Nov. 29, 2018, vol. 132, Supplement 1, p. 1671, 3 Pages, ISSN: 0006-4971, XP009512205.
Mariuzza R.A., et al., "The Structural Basis of Antigen-Antibody Recognition," Annual Review of Biophysics, 1987, vol. 16, pp. 139-159, 23 Pages.
Martinez-Cingolani C., et al., "Development of Chimeric Antigen Receptors for Multiple Myeloma," Biochemical Society transactions, 2016, vol. 44, No. 2, pp. 397-444, 9 Pages.
Menoret S., et al., "Characterization of Immunoglobulin Heavy Chain Knockout Rats," European Journal of Immunology, 2010, vol. 40, pp. 2932-2941.
Menoret S., et al., "Transgenic Animals and Genetic Engineering Techniques," Transgenic Research, 2015, vol. 24, pp. 1079-1085.
Merchant A.M., et al., "An Efficient Route to Human Bispecific IgG," Nature Biotechnology, Gale Group, Inc., Jul. 1998, vol. 16, No. 7, pp. 677-681, XP002141015.
Mikkilineni L., et al., "Chimeric Antigen Receptor T-cell therapies for Multiple Myeloma," Blood, Dec. 14, 2017, vol. 130, No. 24, pp. 2594-2602, 9 Pages.
Miller K., et al., "Design, Construction, and In Vitro Analyses of Multivalent Antibodies," The Journal of Immunology, 2003, vol. 170, No. 9, pp. 4854-4861.
Milteniy Biotec: "Product Summary for Milteniy Biotec CD3 Antibodies Recombinant," [online], [Retrieved on Dec. 22, 2022] Retrieved from URL: https://www.miltenyibiotec.com/DE-en/products/cd3-antibodies-rea613.html#fitc:l-ml.
Min L., et al., "HBs/CD3 Bispecific Antibody Mediates the Cytotoxic Effect of LAK on HBV DNA-transfected Cells," Medical Journal of the People's Liberation Army, vol. 22, No. 6, pp. 397-399.
Moreau P., et al., "Teclistamab in Relapsed or Refractory Multiple Myeloma," The New England Journal of Medicine, Aug. 11, 2022, vol. 387, No. 6, pp. 495-505. Published on Jun. 5, 2022.
Moreaux J., et al., "April and TACI Interact with Syndecan-1 on the Surface of Multiple Myeloma Cells to form an Essential Survival loop," European Journal of Haematology, 2009, vol. 83, pp. 119-129.
Moreaux J., et al., "BAFF and April Protect Myeloma Cells From Apoptosis Induced by Interleukin 6 Deprivation and Dexamethasone," Blood, Apr. 15, 2004, vol. 103, No. 8, pp. 3148-3157, 47 Pages.
Morrison S.L., et al., "Chimeric Human Antibody Molecules: Mouse Antigen-binding Domains with Human Constant Region Domains," 1984, Proceedings of the National Academy of Sciences of the United States of America, vol. 81, pp. 6851-6855.
Muller D., et al., "Bispecific Antibodies for Cancer Immunotherapy," Biodrugs, 2010, vol. 24, No. 2, pp. 89-98.

(56) References Cited

OTHER PUBLICATIONS

Muller D., et al., "Recombinant Bispecific Antibodies for Cellular Cancer Immunotherapy," Current Opinion in Molecular Therapeutics, 2006, vol. 9, No. 4, pp. 319-326.
Muyldermans S., "Single Domain Camel Antibodies: Current Status," Journal of Biotechnology, 2001, vol. 74, No. 4, pp. 277-302.
Naddafi F., et al., "Anti-CD19 Monoclonal Antibodies: A New Approach to Lymphoma Therapy," International Journal of Molecular and Cellular Medicine, Published on Jul. 21, 2015, vol. 4, No. 3, pp. 143-151.
Neisig A., et al., "Assembly of the T-Cell Antigen Receptor, Partcipation of the CD3 Omega Chain," Journal of Immunology, Jul. 15, 1993, vol. 151, pp. 870-879.
Neri P., et al., "Neutralizing B-Cell Activating Factor Antibody Improves Survival and Inhibits Osteoclastogenesis in a Severe Combined Immunodeficient Human Multiple Myeloma Model," Clinical Cancer Research, Oct. 1, 2007, vol. 13, No. 19, pp. 5903-5909, 8 Pages.
Ng L.G., et al., "B Cell-Activating Factor Belonging to the TNF Family (BAFF)-R is the Principal BAFF Receptor Facilitating BAFF Costimulation of Circulating T and B Cells," The Journal of Immunology, Jul. 15, 2004, vol. 173, No. 2, pp. 807-817.
Nguyen V.K., et al., "Functional Heavy-Chain Antibodies in Camelidae," Advances in Immunology, 2001, vol. 79, pp. 261-296.
Nguyen V.K., et al., "Heavy-chain Only Antibodies Derived From Dromedary Are Secreted and Displayed by Mouse B Cells," Immunology, 2003, vol. 109, No. 1, pp. 93-101.
Nishimoto M., et al., "Adoptive Therapy with Cord Blood T Reglatory Cells Enhances Anti-Myeloma Efficacy of T Cell Based Immunotherapies," Blood, 2020, vol. 136 (Suppl1), pp. 26-27, 4 Pages.
Norelli M., et al., "Monocyte-Derived IL-1 and IL-6 Are Differentially Required for Cytokine-release Syndrome and Neurotoxicity Due to CAR T Cells," Nature Medicine, Jun. 2018, vol. 24, pp. 739-748, 16 Pages.
Novak A.J., et al., "Expression of BCMA, TACI, and BAFF-R in Multiple Myeloma: A Mechanism for Growth and Survival," Blood, Jan. 15, 2004, vol. 103, No. 2, pp. 689-694.
Nuttall S.D., et al., "Selection and Affinity Maturation of IgNAR Variable Domains Targeting Plasmodium Falciparum AMA1," Proteins: Structure, Function and Bioinformatics, 2004, vol. 55, pp. 187-197.
Nuttall S.D., et al., "Isolation and Characterization of an IgNAR Variable Domain Specific for the Human Mitochondrial Translocase Receptor Tom70," European Journal of Biochemistry, 2003, vol. 270, pp. 3543-3554.
O'Connor B.P., et al., "BCMA Is Essential for the Survival of Long-lived Bone Marrow Plasma Cells," Journal of Experimental Medicine, Jan. 5, 2004, vol. 199, No. 1, pp. 91-97.
Ofran Y., et al., "Automated Identification of Complementarity Determining Regions (CDRs) Reveals Peculiar Characteristics of CDRs and B-cell Epitopes," Journal of Immunology, 2008, vol. 181, No. 9, pp. 6230-6235, 7 Pages.
OmniAb: "Naturally Optimized Human Antibodies," Feb. 23, 2016, 48 Pages, Retrieved from URL: http://fcontent.stockpr.com/omniab/db/252/746/file/OmniAb.pdf.
Opposition to European Patent No. EP 2780375 B1, Opponent 06: James Poole Limited, Experimental Report 1: Cytotoxic Activity, 6 Pages.
Opposition to European Patent No. EP2780375B1, Opponent 06: James Poole Limited, Experimental Report 2: Epitope Cluster Exchange and Alanine Scanning, 5 Pages.
Padlan E.A., et al., "Identification of Specificity-Determining Residues in Antibodies," FASEB Journal, Jan. 1995, vol. 9, No. 1, pp. 133-139.
Palumbo A., et al., "Daratumumab, Bortezomib, and Dexamethasone for Multiple Myeloma," The New England Journal of Medicine, Aug. 25, 2016, vol. 375, No. 8, pp. 754-766, 13 Pages.
Panowski S.H., et al., "Preclinical Efficacy and Safety Comparison of CD3 Bispecific and ADC Modalities Targeting BCMA for the Treatment of Multiple Myeloma," Molecular Cancer Therapeutics, Nov. 2019, vol. 18, No. 11:2008-2020, pp. OF1-OF13, 13 Pages, DOI: 10.1158/1535-7163.MCT-19-0007.
Patel D.R., et al., "Engineering an April-specific B Cell Maturation Antigen," The Journal of Biological Chemistry, Apr. 16, 2004, vol. 279, No. 16, pp. 16727-16735.
Pelekanou V., et al., "Detection of the TNFSF Members BAFF, April, Tweak and their Receptors in Normal Kidney and Renal Cell Carcinomas," Analytical Cellular Pathology, 2011, vol. 34, pp. 49-60, 13 Pages.
Pelekanou V., et al., "Expression of TNF-superfamily members BAFF and April in Breast Cancer: Immunohistochemical Study in 52 Invasive Ductal Breast Carcinomas," BMC Cancer, Mar. 20, 2008, vol. 8, Article No. 76, 9 Pages.
Pessano S., et al., "The T3/T cell Receptor Complex: Antigenic Distinction between the Two 20-kd T3 (T3-delta and T3-epsilon) Subunits," The EMBO Journal, 1985, vol. 4, No. 2, pp. 337-344.
Pick M., et al., "Daratumumab Resistance is Frequent in Advanced-stage Multiple Myeloma Patients Irrespective of CD38 Expression and is Related to Dismal Prognosis," European Journal of Haematology, 2018, vol. 100, No. 5, pp. 494-501.
Pluckthun A., et al., "New Protein Engineering Approaches to Multivalent and Bispecific Antibody Fragments," Immunotechnology, 1997, vol. 3, No. 2, pp. 83-105.
Presta L., et al., "Generation of Humanized, High Affinity Anti-tissue Factor Antibody for Use as a Novel Antithrombotic Therapeutic," Thrombosis Haemostasis, 2001, vol. 85, No. 3, pp. 379-389.
Presta L.G., et al., "Humanization of an Antibody Directed Against IgE," The Journal of Immunology, Sep. 1, 1993, vol. 151, No. 5, pp. 2623-2632.
Pulte D., et al., "CD39 Expression on T Lymphocytes Correlates with Severity of Disease in Patients with Chronic Lymphocytic Leukemia," Clinical Lymphoma, Myeloma & Leukemia, Aug. 2011, vol. 11, No. 4, pp. 367-372, 14 Pages.
Pulte D., et al., "Improvement in Survival of Older Adults with Multiple Myeloma: Results of an Updated Period Analysis of SEER Data," The Oncologist, 2011, vol. 16, No. 11, pp. 1600-1603.
Qin D-Y., et al., "Paralleled Comparison of Vectors for the Generation of CAR-T Cells," Anti-Cancer Drugs, 2016, vol. 27, No. 8, pp. 711-722.
Raab M.S., et al., "Multiple Myeloma," Lancet, Jul. 25, 2009, vol. 374, pp. 324-339.
Rabia L.A., et al., "Understanding and Overcoming Trade-offs Between Antibody Affinity, specificity, Stability and Solubility," Biochemical Engineering Journal, Sep. 15, 2018, vol. 137, pp. 365-374.
Rahbarizadeh F., et al., "CAR T-cell bioengineering: Single Variable Domain of Heavy Chain Antibody Targeted CARs," Advanced Drug Delivery Reviews, Elsevier, Amsterdam , NL, Feb. 15, 2019, Apr. 17, 2019, vol. 141, pp. 41-46, DOI:10.1016/J.ADDR.2019.04.006, ISSN 0169-409X, XP085750643.
Raje N., et al., "Anti-BCMA CAR T-Cell Therapy bb2121 in Relapsed or Refractory Multiple Myeloma," The New England Journal of Medicine, May 2, 2019, vol. 380, No. 18, pp. 1726-1737.
Rangaswamy U., et al., "A Next Generation Bispecific Antibody Platform for Effective Tumor Cell Killing With Minimal Cytokine Release," Journal for ImmunoTherapy of Cancer, Meeting Info: 34th Annual Meeting and Pre-Conference Programs of the Society for Immunotherapy of Cancer, SITC 2019: Part 2, National Harbor, MD, United States, Nov. 10, 2019-Nov. 10, 2019, vol. 7, Supplement 1, Abstract No. P701, 01 Page.
Rangaswamy U., et al., "A Novel T-cell Bispecific Antibody Platform for Efficient T-cell Mediated Killing of Tumor Cells with Minimal Cytokine Release," Journal of Clinical Oncology, 2018, vol. 36, No. 5, Suppl. 209, 3 Pages.
Ravetch J.V., et al., "Fc Receptors," Annual Review of Immunology, 1991, vol. 9, pp. 457-492.
Reichert J.M., et al., "Development Trends for Monoclonal Antibody Cancer Therapeutics," Nature Reviews, Drug Discovery, May 2007, vol. 6, No. 5, pp. 349-356.
Rennert P., et al., "A Soluble Form of B Cell Maturation Antigen, a Receptor for the Tumor Necrosis Factor Family Member April,

(56) References Cited

OTHER PUBLICATIONS

Inhibits Tumor Cell Growth," Journal of Experimental Medicine, Dec. 4, 2000, vol. 192, No. 11, pp. 1677-1683.
Results of Structural Comparison Performed by Dr. Christine E. Tinberq in the EP Opposition for EP2780375, Cited on Feb. 24, 2023, 04 Pages.
Revets H., et al., "Nanobodies as Novel Agents for Cancer Therapy," Expert Opinion on Biological Therapy, 2005, vol. 5, No. 1, pp. 111-124.
Ridgway J.B.B., et al., "Knobs-into-holes Engineering of Antibody CH3 Domains for Heavy Chain Heterodimerization," Protein Engineering, 1996, vol. 9, No. 7, pp. 617-621.
Rodriguez C., et al., "Initial Results of a Phase 1 Study of TNB-383B, a BCMA x CD3 Bispecific T-Cell Redirecting Antibody in Relapsed/Refractory Multiple Myeloma," Paper Publish, 2020, 2 Pages, [Retrieved on Jun. 7, 2021] Retrieved from URL: https://ash.confex.com/ash/2020/webprogram/COP.html.
Rodriguez C., et al., "Initial Results of a Phase I Study of TNB-383B, a BCMA x CD3 Bispecific T-Cell Redirecting Antibody, in Relapsed/Refractory Multiple Myeloma," Blood, 2020, vol. 136, Supplement 1, pp. 43-44, 3 Pages.
Roit, et al., "Antigen Presentation," Immunology, Moscow, Mir, 2000, pp. 110-111, 14 Pages.
Rossi E.A., et al., "Redirected T-cell Killing of Solid Cancers Targeted With an Anti-CD3/Trop-2-Bispecific Antibody is Enhanced in Combination With Interferon-α," Molecular Cancer Therapeutics, Oct. 2014, vol. 13, No. 10, pp. 2341-2351.
Rouet R., et al., "Fully Human VH Single Domains that Rival the Stability and Cleft Recognition of Camelid Antibodies," Journal of Biological Chemistry, May 8, 2015, vol. 290, No. 19, pp. 11905-11917.
Roux K.H., et al., "Comparisons of the Ability of Human IgG3 Hinge Mutants, IgM, IgE, and IgA2, to Form Small Immune Complexes: A Role for Flexibility and Geometry," The Journal of Immunology, Oct. 15, 1998, vol. 161, No. 8, pp. 4083-4090.
Rudikoff S., et al., "Single Amino Acid Substitution Altering Antigen-Binding Specificity," Proceedings of the National Academy of Sciences (Part 1: Biological Sciences, Mar. 15, 1982), Mar. 1, 1982, vol. 79, No. 6, pp. 1979-1983, 6 Pages, DOI: 10.1073/PNAS.79.6.1979, ISSN 0027-8424, XP002683593.
Rudnick S.I., et al., "Affinity and Avidity in Antibody-Based Tumor Targeting," Cancer Biotherapy and Radiopharmaceuticals, 2009, vol. 24, No. 2, pp. 155-162.
Ryan M.C., et al., "Antibody Targeting of B-cell Maturation Antigen on Malignant Plasma Cells," Molecular Cancer Therapeutics, AACR-NCI-EORTC International Conference: Molecular Targets and Cancer Therapeutics Oct. 19-23, 2013; Boston, MA, Nov. 1, 2007, vol. 6, No. 11, pp. 3009-3018, 11 Pages, ISSN 1535-7163, XP002581270.
Sadelain M., "CD19 CAR T Cells," Cell, Dec. 14, 2017, vol. 171, No. 7, p. 1471.
Sadelain M., et al., "The Basic Principles of Chimeric Antigen Receptor Design," Cancer Discovery, Apr. 2013, vol. 3, No. 4, pp. 388-398.
Salazar-Camarena D.C., et al., "Association of BAFF, April Serum Levels, BAFF-R, TACI and BCMA Expression on Peripheral B-cell Subsets With Clinical Manifestations in Systemic Lupus Erythematosus," Lupus, May 2016, vol. 25, No. 6, 11 Pages.
Saller R., "Statutory Declaration," Executive Director Program Management at Amgen Research (Munich) GmbH, Vice President R&D Operations & Planning, Jan. 2021, 1 Page.
Salmeron A., et al., "A Conformational Epitope Expressed Upon Association of CD3-epsilon With Either CD3-delta or CD3-gamma is the Main Target for Recognition by Anti-CD3 Monoclonal Antibodies," Journal of Immunology, Nov. 1, 1991, vol. 147, No. 9, pp. 3047-3052.
Sanchez E., et al., "Serum B-cell Maturation Antigen is Elevated in Multiple Myeloma and Correlates with Disease Status and Survival," British Journal of Haematology, 2012, vol. 158, No. 6, pp. 727-738.
Sandusky G.E., et al., "Use of Monoclonal Antibodies to Human Lymphocytes to Identify Lymphocyte Subsets in Lymph Nodes of the Rhesus Monkey and the Dog," The Journal of Medical Primatology, 1986, vol. 15, No. 6, pp. 441-451.
Sanz I., et al., "B Cells as Therapeutic Targets in SLE," Nature Reviews Rheumatology, Jun. 2010, vol. 6, No. 6, pp. 326-337.
Schooten W.V., et al., "A Novel CD3/BCMA Bispecific Antibody Selectively Kills Plasma Cells in Bone Marrow of Healthy Individuals with Improved Safety," Lupus Science & Medicine, 2019, vol. 6, Supplement 1, pp. A1-A227, Abstract 293.
Seckinger A., et al., "Target Expression, Generation, Preclinical Activity, and Pharmacokinetics of the BCMA-T Cell Bispecific Antibody EM801 for Multiple Myeloma Treatment," Cancer Cell, Cell Press, United States, Mar. 23, 2017, vol. 31, No. 3, pp. 396-410.
Sequence Alignment of BCMA (TNFRSF17) Amino Acids 24-41 ("Epitope Cluster 3") from Different Species, cited on Apr. 17, 2023 in the EP Opposition for EP2780375, 3 Pages.
Sequence Alignment of CD3 Epsilon; Crab-eating Macaque, Rhesus Macaque, cited on Jun. 12, 2020 in the EP Opposition for EP2780375, 1 page.
Sequence Alignment of the 27 N-Terminal Amino Acids of the CD3 Epsilon Chain of Humans, Crab-Eating Macaque and Rhesus Macaque, 1 Page.
Sequence Comparison, cited on May 18, 2021, in the EP Opposition for EP2780375, 4 Pages.
Sequence Comparison of WO2008/011956 and EP 2780375B1, 4 Pages.
Serganova I., et al., "LDH-A Regulates the Tumor Microenvironment via HIF-Signaling and Modulates the Immune Response," PLoS One, 2018, vol. 13, No. 9:e0203965, 22 Pages.
Shallis R.M., et al., "The Multi-Faced Potential of CD38 Antibody Targeting in Multiple Myeloma," Cancer Immunol Immunother, 2017, vol. 66, pp. 697-703.
Shannessy D.J.O., et al., "Serum Folate Receptor Alpha, Mesothelin and Megakaryocyte Potentiating Factor in Ovarian Cancer: Association to Disease Stage and Grade and Comparison to CA125 and HE4," Journal of Ovarian Research, BioMed Central Ltd, London, UK, Apr. 17, 2013, vol. 6, No. 1, p. 29.
Shields R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry, Mar. 2, 2001, vol. 276, No. 9, pp. 6591-6604.
Shoji-Hosaka E., et al., "Enhanced Fc-Dependent Cellular Cytotoxicity of Fc Fusion Proteins Derived from TNF Receptor II and LFA-3 by Fucose Removal from Asn-Linked Oligosaccharides," Journal of Biochemistry, 2006, vol. 140, pp. 777-783, DOI:10.1093/jb/mvj207.
Singer M., et al., "Genes and Genomes a Changing Perspective," Moscow, MIR, 1991, 1:63-64, 17 Pages.
Sinobiological: "Flow Cytometry Antibody," CD3e Cat. No. CT026-R301, Antibody Catalogue, 2017, pp. 1-2, 152 Pages, [Retrieved on Mar. 25, 2019] Retrieved from URL: http://www.sinobiologica.com/flow-cytometry-antibody-elite.html.
Sinobiological: "Rabbit Monoclonal Recombinant Anti-CD3D & CD3E Heterodimer Antibody," China, Jul. 7, 2016, 2 Pages, Cat. No. CT026-R301, XP055574141, [Retrieved on Jul. 5, 2022] Retrieved from URL: https://www.sinobiological.com/antibodies/human-cynomolgus-cd3d-cd3e-ct026-r301.
Sitia R., et al., "Developmental Regulation of IgM Secretion: The Role of the Carboxy-Terminal Cysteine," Cell, Mar. 9, 1990, vol. 60, pp. 781-790.
Smith S.B., et al., "Expression of Folate Receptor Alpha in the Mammalian Retinol Pigmented Epithelium and Retina," Investigative Ophthalmology & Visual Science, 1999, vol. 40, No. 5, pp. 840-848.
Soares A., et al., "Transient Global T Cell Activation After Vaccination of Rhesus Macaques with a DNA-Poxvirus Vaccine Regimen for HIV," Vaccine, 2015, vol. 33, Issue 30, pp. 3435-3439, 7 Pages.
Song D.G., et al., "In Vivo Persistence, Tumor Localization, and Antitumor Activity of CAR-Engineered T Cells is Enhanced by Costimulatory Signaling Through CD137 (4-1BB)," Cancer research, 2011, vol. 71, No. 13, pp. 4617-4627.

(56) References Cited

OTHER PUBLICATIONS

Sun L.L., et al., "Anti-CD20/CD3 T Cell-Dependent Bispecific Antibody for the Treatment of B Cell Malignancies," Science Translational Medicine, May 13, 2015, vol. 7, No. 287, 287ra70-287ra70, 12 Pages.
Supporting Evidence in EP Opposition No. 2780375 for EP Application No. 12805432.7, Regarding Availability of Kontermann, Bispecific Antibodies, Springer-Verlag Berlin Heidelberg, 2011, 3 Pages.
Tai Y-T., et al., "April and BCMA Promote Human Multiple Myeloma Growth and Immunosuppression in the Bone Marrow Microenvironment," Blood, Jun. 23, 2016, vol. 127, No. 25, pp. 3225-3236.
Tai Y-T., et al., "Novel Anti-B-Cell Maturation Antigen Antibody-drug Conjugate (GSK2857916) Selectively Induces Killing of Multiple Myeloma," Blood, 2014, vol. 123, No. 20, pp. 3128-3138.
Tam S.H., et al., "Functional, Biophysical and Structural Characterization of Human IgG1 and IgG4 Fc Variants with Ablated Immune Functionality," Antibodies, Sep. 1, 2017, vol. 6, No. 12, pp. 1-34.
Tao M-H., et al., "Structural Features of Human Immunoglobulin G That Determine Isotype-specific Differences in Complement Activation," Journal of Experimental Medicine, Aug. 1993, vol. 178, No. 2, pp. 661-667.
Tarte K., et al., "BAFF is a Survival Factor for Multiple Myeloma Cells," Myeloma Biology II: 811a, 2002, 1 Page (Abstract #3203).
"Teneobio Announces US FDA Approval of the Investigational New Drug Application for TNB-383B and the Initiation of Phase I Clinical Studies in Multiple Myeloma Patients," Global Newswire, Apr. 29, 2019, 8:00 ET, Retrieved from the Internet URL: https://www.globenewswire.com/news-release/2019/04/29/1811199/0/en/Teneobio-Announces-US-FDA-Approval-of-the-Investigational-New-Drug-Application-for-TNB-383B-and-the-Initiation-of-Phase-I-Clinical-Studies-in-Multiple-Myeloma-Patients.html.
Thakur A., et al., "Cancer Therapy with Bispecific Antibodies: Clinical Experience," Current Opinion in Molecular Therapeutics, 2010, vol. 12, No. 3, pp. 340-349.
Thompson J.S., et al., "BAFF Binds to the Tumor Necrosis Factor Receptor-like Molecule B Cell Maturation Antigen and Is Important for Maintaining the Peripheral B Cell Population," Journal of Experimental Medicine, Jul. 3, 2000, vol. 192, No. 1, pp. 129-135.
Thurber G.M., et al., "Antibody Tumor Penetration: Transport Opposed by Systemic and Antigen-Mediated Clearance," Advanced Drug Delivery Reviews, 2008, vol. 60, pp. 1421-1434.
Tiller K.E., et al., "Facile Affinity Maturation of Antibody Variable Domains Using Natural Diversity Mutagenesis," Frontiers in Immunology, 2017, vol. 8, No. 986, DOI:10.3389/fimmu.2017.00986.
Topp M.S., et al., "Anti-B-Cell Maturation Antigen BiTE Molecule AMG 420 Induces Responses in Multiple Myeloma," Journal of Clinical Oncology, Published on Jan. 2, 2020, vol. 38, Issue 8, pp. 775-783, 15 Pages.
Trinklein N., et al., "Abstract LB-090: Sequence-based Discovery of Fully Human Anti-CD3 and Anti-PDL1 Single Domain Antibodies Using Novel Transgenic Rats," Cancer Research, Jul. 2016, vol. 76, Suppl. 14, 1 Page, Retrieved from URL: http://cancerres.aacrjournals.org/content/76/14_Supplement/LB-090.
Trinklein N.D., et al., "Efficient Tumor Killing and Minimal Cytokine Release with Novel T-Cell Agonist Bispecific Antibodies," MABS, 2019, vol. 11, No. 4, pp. 639-652.
Turesson I., et al., "Patterns of Improved Survival in Patients With Multiple Myeloma in the Twenty-First Century: A Population-Based Study," Journal of Clinical Oncology, Feb. 10, 2010, vol. 28, No. 5, pp. 830-834.
Turley D.M., "Prospects for Antigen-Specific Tolerance Based Therapies for the Treatment of Multiple Sclerosis," Results and Problems in Cell Differentiation, vol. 51, pp. 217-235, doi:10.1007/400_2008_13, XP009174523.
Ueda O., et al., "Entire CD3ε, δ, and γ Humanized Mouse to Evaluate Human CD3-Mediated Therapeutics," Scientific Reports, Apr. 3, 2017, vol. 7, No. 45839, 16 Pages, DOI: 10.1038/srep45839.
Vafa O., et al., "Perspective: Designing T-Cell Engagers with Better Therapeutic Windows," Frontiers in Oncology, 2020, vol. 10, No. 446, DOI:10.3389/fonc.2020.00446.
Van Der Linden R.H.J., et al., "Comparison of Physical Chemical Properties of Llama VHH Antibody Fragments and Mouse Monoclonal Antibodies," Biochimica et Biophysica Acta, 1999, vol. 1431, No. 1, pp. 37-46.
Velasquez MP, et al., "Redirecting T cells to hematological malignancies with bispecific antibodies," Blood. Jan. 4, 2018;131(1):30-38.
Verkleij C.P.M., et al., "T-Cell Redirecting Bispecific Antibodies Targeting BCMA for the Treatment of Multiple Myeloma," Oncotarget, Nov. 10, 2020, vol. 11, No. 45, pp. 4076-4081, DOI: 10.18632/oncotarget.27792.
Vidal-Laliena M., et al., "Characterization of Antibodies Submitted to the B Cell Section of the 8th Human Leukocyte Differentiation Antigens Workshop by Flow Cytometry and Immunohistochemistry," Cellular Immunology, 2005, vol. 236, pp. 6-16.
Vinvke C., et al., "General Strategy to Humanize a Camelid Single-domain Antibody and Identification of a Universal Humanized Nanobody Scaffold," Journal of Biological Chemistry, Jan. 30, 2009, vol. 284, No. 5, pp. 3273-3284.
Vu M.D., et al., "A New Class of T-cell Bispecific Antibodies for the Treatment of Multiple Myeloma, Binding to B Cell Maturation Antigen and Cd3 and Showing Potent, Specific Antitumor Activity in Myeloma Cells and Long Duration of Action in Cynomolgus Monkeys," Blood, Dec. 3, 2015, vol. 126, No. 23, p. 2998, 03 p. DOI: 10.1182/blood.V126.23.2998.2998, XP086650811.
Wagner H.J., et al., "A Two-Step Approach for the Design and Generation of Nanobodies," International Journal of Molecular Sciences, 2018, vol. 19, No. 11:3444, 16 Pages, DOI:10.3390/ijms19113444.
Walker J.A., et al., "CD22: An Inhibitory Enigma," Immunology, 2007, vol. 123, pp. 314-325.
Wallweber H.J.A., et al., "The Crystal Structure of a Proliferation-inducing Ligand, April," Journal of Molecular Biology, 2004, vol. 343, No. 2, pp. 283-290, 8 Pages.
Wang C., et al., "A Systematic Approach for Analysis and Characterization of Mispairing in Bispecific Antibodies with Asymmetric Architecture," MABS, 2018, vol. 10, No. 8, pp. 1226-1235.
Wang D.D., et al., "Fixed Dosing Versus Body Size-Based Dosing of Monoclonal Antibodies in Adult Clinical Trials," Journal of Clinical Pharmacology, Jul. 20, 2009, vol. 49, No. 9, pp. 1012-1024, 13 Pages.
Wang Z., et al., "Biomarkers of Cytokine Release Syndrome and Neurotoxicity Related to CAR-T Cell Therapy," Biomarkers Research, Jan. 22, 2018, vol. 6, No. 4, 10 pages.
Wark, et al., "Latest technologies for the enhancement of antibody affinity," Advanced Drug Delivery Reviews, 2006, vol. 58, pp. 657-670.
Waxman A.J., et al., "Racial Disparities in Incidence and Outcome in Multiple Myeloma: A Population-based Study," Blood, Dec. 16, 2010, vol. 116, No. 25, pp. 5501-5506.
Wayback Machine: "Q02223. TNR17_Human," BCMA, UniprotKB/Swiss-Prot Entry, Aug. 3, 2011, 8 pages, [Retrieved on Apr. 29, 2020] Retrieved from URL: https://web.archive.org/web/20110803071256/ https://www.uniprot.orq/uniprot/Q02223.
Weidle U.H., et al., "The Intriguing Options of Multispecific Antibody Formats for Treatment of Cancer," Cancer Genomics & Proteomics, 2013, vol. 10, No. 1, pp. 1-18.
Weitman S.D., et al., "Distribution of the Folate Receptor Gp38 in Normal and Malignant Cell Lines and Tissues," Cancer Research, American Association for Cancer Research, US, Jun. 15, 1992, vol. 52, pp. 3396-3401.
Werther W.A., et al., "Humanization of Anti-lymphocyte Function-Associated Antigen (LFA)-1 Monoclonal Antibody and Reengineering of the Humanized Antibody for Binding to Rhesus LFA-1," Journal of Immunology, 1996, vol. 157, pp. 4986-4995.
Wibowo AS et al., "Structures of human folate receptors reveal biological trafficking states and diversity in folate and antifolate recognition." Proceedings of the National Academy of Sciences of the United States of America. 2013;110(38):15180-8.

(56) References Cited

OTHER PUBLICATIONS

Winkler K., et al., "Changing the Antigen Binding Specificity by Single Point Mutations of an Anti-p24 (HIV-1) Antibody," The Journal of Immunology, Williams & Wilkins Co, US, Oct. 15, 2000, vol. 165, No. 8, pp. 4505-4514, ISSN 0022-1767, XP002579393.
Winter, et al., "Humanized Antibodies," Immunology Today, 1993, vol. 14, No. 5, pp. 139-143.
Winter G., et al., "Humanized Antibodies," Immunology Today, 1993, vol. 14, No. 6, pp. 243-236.
Woof J.M., et al., "Human Antibody-FC Receptor Interactions Illuminated by Crystal Structures," Nature Reviews, Immunology, Feb. 2004, vol. 4, No. 2, pp. 89-99.
Wu C., et al., "Simultaneous Targeting of Multiple Disease Mediators by a Dual-Variable-Domain Immunoglobulin," Nature Biotechnology, Nov. 2007, vol. 25, No. 11, pp. 1290-1297.
Wu G., et al., "A Mucin1 C-Terminal Subunit-Directed Monoclonal Antibody Targets Overexpressed Mucin1 in Breast Cancer," Theranostics, AU, Jan. 1, 2018, vol. 8 No. 1, pp. 78-91, DOI:10.7150/thno.21278, ISSN 1838-7640, XP055934430, Retrieved from URL: https://www.ncbi.nlm.nih.gov/pmc/articles/PMC5743461/pdf/thnov08p0078.pdf.
Wu S., et al., "CD38-Expressing Macrophages Drive Age-Related NAD+ Decline," Nature Metabolism, Nov. 2020, vol. 2, pp. 1186-1187.
Wu W., et al., "A Novel VHH Antibody Targeting the B Cell-Activating Factor for B-Cell Lymphoma," International Journal of Molecular Sciences, 2014, vol. 15, No. 6, pp. 9481-9489.
Xianchao, "The Expression, Purification and Activity Study of April Blocking Qi IJ BCMA-Fc," Chinese Excellent Doctoral Dissertation Full-text Database (Electronic Journal Network), 2015, Issue 2, E059-37, pp. 1-26, 122 Pages.
Yau, et al., "Affinity Maturation of a V(H)H by Mutational Hotspot Randomization," Journal of Immunological Methods, 2005, vol. 297, (Issues 1-2), pp. 213-224.
Yoon S.T., et al., "Both High and Low Avidity Antibodies to the T Cell Receptor Can Have Antagonist Activity," Immunity, Oct. 1994, vol. 1, No. 7, pp. 563-569.
Yu M., et al., "Development of CD3/CD22 Bispecific Antibody," Journal of Cellular and Molecular Immunology, 2001, vol. 17(3), 2 pages.
Zare H., et al., "Production of Nanobodies Against Prostate-Specific Membrane Antigen (PSMA) Recognizing LnCaP Cells," International Journal of Biological Markers, 2014, vol. 29, No. 2, pp. e169-e179, DOI:10.5301 /jbm.5000063.
Zarei N., et al., "High Efficient Expression of a Functional Humanized Single-chain Variable Fragment (ScFv) Antibody Against CD22 in Pichia Pastoris," Applied Microbiology and Biotechnology, Dec. 2014, vol. 98, No. 24, pp. 10023-100399, 2 Pages, Abstract only.
Zavrtanik U., et al., "Structural Basis of Epitope Recognition by Heavy-Chain Camelid Antibodies," Journal of Molecular Biology, 2018, vol. 430, No. 21, pp. 4369-4386.
Zhao S., et al., "A Germline Knowledge Based Computational Approach for Determining Antibody Complementarity Determining Regions," Molecular Immunology, 2010, vol. 47, No. 4, pp. 694-700.
Zou X., et al., "Heavy Chain—Only Antibodies Are Spontaneously Produced in Light Chain—Deficient Mice," The Journal of Experimental Medicine, Dec. 17, 2007, vol. 204, No. 13, pp. 3271-3283.

FIG. 1

| Column 1 | Column 2 | Column 3 |
|---|---|---|
| Clone ID | Raji MUC1+ cell | CHO_OFFtgt |
| 375747 | 64.36 | 1.7 |
| 375505 | 59.9 | 1.7 |

FIG. 3

| Column 1 | Column 2 |
| --- | --- |
| Clone ID | Raji MUC1+ cell |
| 375747 | 1.0 |
| 375505 | 1.1 |

A.

B.

FIG. 4, Cont.
C.
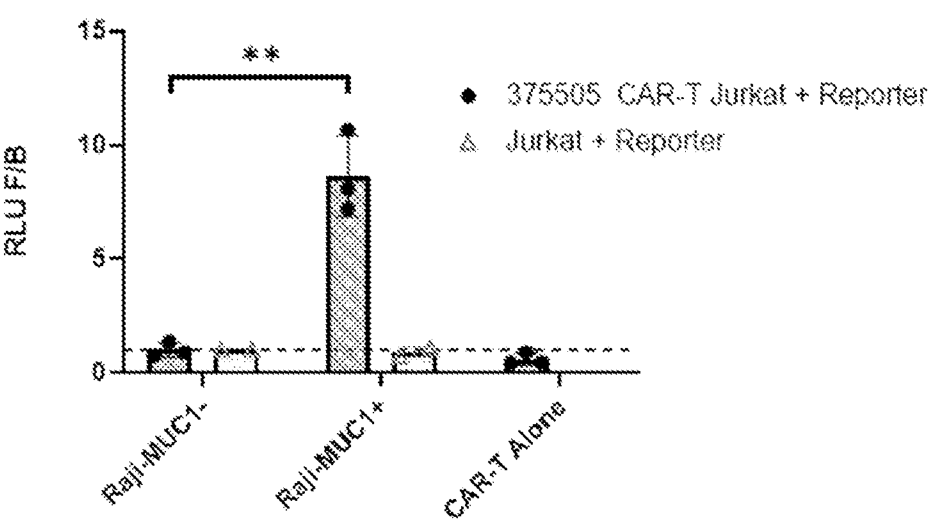

A.

B.

A.

B.

A.

B.

A.

B.

```
SEQUENCE LISTING

<160> NUMBER OF SEQ ID NOS: 43

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Ala Phe Ser Gly Asn Ser
1               5


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Thr Ser Ser Gly Arg Ser Ile
1               5


<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Thr Gly Gly Thr Gly Thr Ser Leu Phe Asp Tyr
1               5                   10


<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
      peptide

<400> SEQUENCE: 4

Gly Phe Thr Phe Ser Ser His Ser
1               5


<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Ser Ser Ser Ser Asn Ile Lys
1               5


<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Thr Gly Gly Thr Gly Ile Thr Val Leu Asp Tyr
1               5                   10


<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ala Phe Ser Gly Asn
            20                  25                  30

Ser Met Asn Trp Val Arg Gln Ala Pro Gly Lys Gly Leu Glu Trp Val
        35                  40                  45

Ala Phe Ile Thr Ser Ser Gly Arg Ser Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Asp Glu Asp Thr Ala Leu Tyr Tyr Cys
                85                  90                  95

Ala Thr Gly Gly Thr Gly Thr Ser Leu Phe Asp Tyr Arg Gly Gln Gly
            100                 105                 110

Thr Leu Val Thr Val Ser Ser
        115


<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 8

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Ser Met Asn Trp Val Arg Gln Ala Pro Gly Lys Gly Leu Glu Trp Val
35 40 45

Ser Phe Ile Ser Ser Ser Ser Asn Ile Lys Lys Tyr Ala Asp Ser Val
50 55 60

Lys Gly Arg Phe Thr Ile Ser Arg Asp Asn Ala Lys Asn Ser Leu Phe
65 70 75 80

Leu Gln Met Asn Ser Leu Arg Asp Glu Asp Thr Ala Val Tyr Tyr Cys
85 90 95

Ala Thr Gly Gly Thr Gly Ile Thr Val Leu Asp Tyr Arg Gly Gln Gly
100 105 110

Thr Leu Val Thr Val Ser Ser
115

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Gly Phe Thr Phe Asp Asp Tyr Ala
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ile Ser Trp Asn Ser Gly Ser Ile
1 5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ala Lys Asp Ser Arg Gly Tyr Gly Asp Tyr Arg Leu Gly Gly Ala Tyr
1 5 10 15

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

```
Gly Phe Thr Phe His Asn Tyr Ala
1               5


<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Ser Trp Asn Ser Gly Ser Ile
1               5


<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Lys Asp Ser Arg Gly Tyr Gly Asp Tyr Ser Leu Gly Gly Ala Tyr
1               5                   10                  15


<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Val Ser Ser Asn
1               5


<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Ser
1


<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Tyr Asn Asn Trp Pro Trp Thr
1               5


<210> SEQ ID NO 18
<211> LENGTH: 123
<212> TYPE: PRT
<213> ORGANISM: Artificial Sequence
<220> FEATURE:
```

```
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser
        115                 120


<210> SEQ ID NO 19
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser
        115                 120


<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
```

```
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105


<210> SEQ ID NO 21
<211> LENGTH: 330
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 22
<211> LENGTH: 327
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 23
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 24
<211> LENGTH: 327
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Ala Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 25

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 26
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 27
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 28
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
```

-continued

```
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 29
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
```

```
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 30
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 31
<211> LENGTH: 229
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 32
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80
```

```
Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 33
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Arg Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220
```

```
Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450
```

<210> SEQ ID NO 34
<211> LENGTH: 348
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ala Phe Ser Gly Asn
            20                  25                  30

Ser Met Asn Trp Val Arg Gln Ala Pro Gly Lys Gly Leu Glu Trp Val
        35                  40                  45

Ala Phe Ile Thr Ser Ser Gly Arg Ser Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Asp Glu Asp Thr Ala Leu Tyr Tyr Cys
                85                  90                  95

Ala Thr Gly Gly Thr Gly Thr Ser Leu Phe Asp Tyr Arg Gly Gln Gly
            100                 105                 110

Thr Leu Val Thr Val Ser Ser Glu Ser Lys Tyr Gly Pro Pro Cys Pro
```

```
        115                 120                 125

Pro Cys Pro Ala Pro Glu Ala Ala Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Ser Cys Ala Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Val Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345


<210> SEQ ID NO 35
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ala Phe Ser Gly Asn
            20                  25                  30

Ser Met Asn Trp Val Arg Gln Ala Pro Gly Lys Gly Leu Glu Trp Val
        35                  40                  45

Ala Phe Ile Thr Ser Ser Gly Arg Ser Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Asp Glu Asp Thr Ala Leu Tyr Tyr Cys
                85                  90                  95

Ala Thr Gly Gly Thr Gly Thr Ser Leu Phe Asp Tyr Arg Gly Gln Gly
            100                 105                 110

Thr Leu Val Thr Val Ser Ser Gly Gly Gly Gly Ser Gly Gly Gly Gly
        115                 120                 125
```

```
Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ala Phe Ser Gly
145                 150                 155                 160

Asn Ser Met Asn Trp Val Arg Gln Ala Pro Gly Lys Gly Leu Glu Trp
                165                 170                 175

Val Ala Phe Ile Thr Ser Ser Gly Arg Ser Ile Lys Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Thr Leu Arg Asp Glu Asp Thr Ala Leu Tyr Tyr
    210                 215                 220

Cys Ala Thr Gly Gly Thr Gly Thr Ser Leu Phe Asp Tyr Arg Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser Gln Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Gln Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Val Ser Arg Leu Thr Val Asp Lys Ser Arg Trp Gln
        435                 440                 445

Glu Gly Asn Val Phe Ser Cys Ser Val Met His Glu Ala Leu His Asn
    450                 455                 460

His Tyr Thr Gln Lys Ser Leu Ser Leu Ser Leu Gly Lys
465                 470                 475


<210> SEQ ID NO 36
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Phe Ile Ser Ser Ser Ser Asn Ile Lys Lys Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Thr Gly Gly Thr Gly Ile Thr Val Leu Asp Tyr Arg Gly Gln Gly
            100                 105                 110

Thr Leu Val Thr Val Ser Ser Glu Ser Lys Tyr Gly Pro Pro Cys Pro
        115                 120                 125

Pro Cys Pro Ala Pro Glu Ala Ala Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Ser Cys Ala Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Val Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345
```

<210> SEQ ID NO 37
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
```

```
            20                  25                  30

Ser Met Asn Trp Val Arg Gln Ala Pro Gly Lys Gly Leu Glu Trp Val
        35                  40                  45

Ser Phe Ile Ser Ser Ser Ser Asn Ile Lys Lys Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Thr Gly Gly Thr Gly Ile Thr Val Leu Asp Tyr Arg Gly Gln Gly
            100                 105                 110

Thr Leu Val Thr Val Ser Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

His Ser Met Asn Trp Val Arg Gln Ala Pro Gly Lys Gly Leu Glu Trp
                165                 170                 175

Val Ser Phe Ile Ser Ser Ser Ser Asn Ile Lys Lys Tyr Ala Asp Ser
            180                 185                 190

Val Lys Gly Arg Phe Thr Ile Ser Arg Asp Asn Ala Lys Asn Ser Leu
        195                 200                 205

Phe Leu Gln Met Asn Ser Leu Arg Asp Glu Asp Thr Ala Val Tyr Tyr
    210                 215                 220

Cys Ala Thr Gly Gly Thr Gly Ile Thr Val Leu Asp Tyr Arg Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser Gln Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Gln Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Val Ser Arg Leu Thr Val Asp Lys Ser Arg Trp Gln
        435                 440                 445
```

```
Glu Gly Asn Val Phe Ser Cys Ser Val Met His Glu Ala Leu His Asn
    450                 455                 460

His Tyr Thr Gln Lys Ser Leu Ser Leu Ser Leu Gly Lys
465                 470                 475


<210> SEQ ID NO 38
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ala Phe Ser Gly Asn
            20                  25                  30

Ser Met Asn Trp Val Arg Gln Ala Pro Gly Lys Gly Leu Glu Trp Val
        35                  40                  45

Ala Phe Ile Thr Ser Ser Gly Arg Ser Ile Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Asp Glu Asp Thr Ala Leu Tyr Tyr Cys
                85                  90                  95

Ala Thr Gly Gly Thr Gly Thr Ser Leu Phe Asp Tyr Arg Gly Gln Gly
            100                 105                 110

Thr Leu Val Thr Val Ser Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Ala Ala Ser Gly Phe Thr Phe Ser Ser
145                 150                 155                 160

His Ser Met Asn Trp Val Arg Gln Ala Pro Gly Lys Gly Leu Glu Trp
                165                 170                 175

Val Ser Phe Ile Ser Ser Ser Ser Asn Ile Lys Lys Tyr Ala Asp Ser
            180                 185                 190

Val Lys Gly Arg Phe Thr Ile Ser Arg Asp Asn Ala Lys Asn Ser Leu
        195                 200                 205

Phe Leu Gln Met Asn Ser Leu Arg Asp Glu Asp Thr Ala Val Tyr Tyr
    210                 215                 220

Cys Ala Thr Gly Gly Thr Gly Ile Thr Val Leu Asp Tyr Arg Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser Gln Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
```

```
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Gln Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Val Ser Arg Leu Thr Val Asp Lys Ser Arg Trp Gln
        435                 440                 445

Glu Gly Asn Val Phe Ser Cys Ser Val Met His Glu Ala Leu His Asn
    450                 455                 460

His Tyr Thr Gln Lys Ser Leu Ser Leu Ser Leu Gly Lys
465                 470                 475


<210> SEQ ID NO 39
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Phe Ile Ser Ser Ser Ser Asn Ile Lys Lys Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Thr Gly Gly Thr Gly Ile Thr Val Leu Asp Tyr Arg Gly Gln Gly
            100                 105                 110

Thr Leu Val Thr Val Ser Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ala Phe Ser Gly
145                 150                 155                 160

Asn Ser Met Asn Trp Val Arg Gln Ala Pro Gly Lys Gly Leu Glu Trp
                165                 170                 175

Val Ala Phe Ile Thr Ser Ser Gly Arg Ser Ile Lys Tyr Ala Asp Ser
            180                 185                 190

Val Lys Gly Arg Phe Thr Ile Ser Arg Asp Asn Ala Lys Asn Ser Leu
        195                 200                 205
```

```
Tyr Leu Gln Met Asn Thr Leu Arg Asp Glu Asp Thr Ala Leu Tyr Tyr
    210                 215                 220

Cys Ala Thr Gly Gly Thr Gly Thr Ser Leu Phe Asp Tyr Arg Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Glu Ala Ala Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser Gln Glu Asp Pro Glu Val Gln
    290                 295                 300

Phe Asn Trp Tyr Val Asp Gly Val Glu Val His Asn Ala Lys Thr Lys
305                 310                 315                 320

Pro Arg Glu Glu Gln Phe Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Gly Leu Pro Ser Ser Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Gln Glu Glu Met Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Val Ser Arg Leu Thr Val Asp Lys Ser Arg Trp Gln
        435                 440                 445

Glu Gly Asn Val Phe Ser Cys Ser Val Met His Glu Ala Leu His Asn
    450                 455                 460

His Tyr Thr Gln Lys Ser Leu Ser Leu Ser Leu Gly Lys
465                 470                 475


<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Gly Gly Ser
1               5


<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Gly Gly Ser Gly Gly Gly Gly Ser
1               5                   10
```

<210> SEQ ID NO 42
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe His Asn Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Arg Gly Tyr Gly Asp Tyr Ser Leu Gly Gly Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365
```

```
Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 43
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Gly Ser" repeating units

<400> SEQUENCE: 43

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

ANTI-MUC1-C ANTIBODIES AND CAR-T STRUCTURES

CROSS-REFERENCE TO RELATED APPLICATIONS

This application claims priority benefit of the filing date of U.S. Provisional Patent Appliation Ser. No. 63/154,618, filed on Feb. 26, 2021, the disclosure of which is incorporated by reference herein in its entirety.

FIELD OF THE INVENTION

The present invention concerns antibodies (e.g., UniAbs™) and CAR-T structures that bind to MUC1-C. The invention further concerns methods of making such antibodies and CAR-T structures, compositions, including pharmaceutical compositions, comprising such antibodies and CAR-T structures, and their use to treat disorders that are characterized by the expression of MUC1-C.

BACKGROUND OF THE INVENTION

MUC1

Mucin 1 (MUC1) is a heavily glycosylated, single pass type I transmembrane protein. The N-terminal subunit (MUC1-N) and C-terminal subunit (MUC1-C) form a stable heterodimeric complex. MUC1 is highly polymorphic, with greater than 90 isoforms, differing in the number of tandem repeats in the VNTR (variable number tandem repeat) region of the N-terminal subunit. Mucins line the apical surface of epithelial cells in the lungs, stomach, mammary glands, intestines, and several other organs. In healthy tissues, mucins protect the body from infection. Aberrantly glycosylated MUC1 is overexpressed in human epithelial cancers and apical polarity is lost in tumor cells (Sousa et al. 2016, PMC: 4998183, Nath and Mukherjee, 2014, PMID: 5500204). MUC1 can be cleaved by proteases and cleaved MUC1-N is shed from the cell and can trigger inflammation. The non-shed oncogenic MUC1-C subunit is short, containing a 58 amino acid membrane proximal extracellular domain that shows promise as a target for antibody drug conjugates, monoclonal antibodies and CAR-T therapies (Panchamoorthy et al., 2018, PMC: 6124453; Kufe, 2009, PMC: 2951677).

Heavy Chain Antibodies

In a conventional IgG antibody, the association of the heavy chain and light chain is due in part to a hydrophobic interaction between the light chain constant region and the CH1 constant domain of the heavy chain. There are additional residues in the heavy chain framework 2 (FR2) and framework 4 (FR4) regions that also contribute to this hydrophobic interaction between the heavy and light chains.

It is known, however, that sera of camelids (sub-order Tylopoda which includes camels, dromedaries and llamas) contain a major type of antibodies composed solely of paired H-chains (heavy-chain only antibodies or UniAbs™). The UniAbs™ of *Camelidae* (*Camelus dromedarius, Camelus bactrianus, Lama glama, Lama guanaco, Lama alpaca* and *Lama vicugna*) have a unique structure consisting of a single variable domain (VHH), a hinge region and two constant domains (CH2 and CH3), which are highly homologous to the CH2 and CH3 domains of classical antibodies. These UniAbs™ lack the first domain of the constant region (CH1) which is present in the genome, but is spliced out during mRNA processing. The absence of the CH1 domain explains the absence of the light chain in the UniAbs™, since this domain is the anchoring place for the constant domain of the light chain. Such UniAbs™ naturally evolved to confer antigen-binding specificity and high affinity by three CDRs from conventional antibodies or fragments thereof (Muyldermans, 2001; *J Biotechnol* 74:277-302; Revets et al., 2005; *Expert Opin Biol Ther* 5:111-124). Cartilaginous fish, such as sharks, have also evolved a distinctive type of immunoglobulin, designated as IgNAR, which lacks the light polypeptide chains and is composed entirely by heavy chains. IgNAR molecules can be manipulated by molecular engineering to produce the variable domain of a single heavy chain polypeptide (vNARs) (Nuttall et al. *Eur. J. Biochem.* 270, 3543-3554 (2003); Nuttall et al. *Function and Bioinformatics* 55, 187-197 (2004); Dooley et al., *Molecular Immunology* 40, 25-33 (2003)).

The ability of heavy chain-only antibodies devoid of light chain to bind antigen was established in the 1960s (Jaton et al. (1968) *Biochemistry,* 7, 4185-4195). Heavy chain immunoglobulin physically separated from light chain retained 80% of antigen-binding activity relative to the tetrameric antibody. Sitia et al. (1990) *Cell,* 60, 781-790 demonstrated that removal of the CH1 domain from a rearranged mouse μ gene results in the production of a heavy chain-only antibody, devoid of light chain, in mammalian cell culture. The antibodies produced retained VH binding specificity and effector functions.

Heavy chain antibodies with a high specificity and affinity can be generated against a variety of antigens through immunization (van der Linden, R. H., et al. *Biochim. Biophys. Acta.* 1431, 37-46 (1999)) and the VHH portion can be readily cloned and expressed in yeast (Frenken, L. G. J., et al. *J. Biotechnol.* 78, 11-21 (2000)). Their levels of expression, solubility and stability are significantly higher than those of classical F(ab) or Fv fragments (Ghahroudi, M. A. et al. *FEBS Lett.* 414, 521-526 (1997)).

Mice in which the λ (lambda) light (L) chain locus and/or the λ and κ (kappa) L chain loci have been functionally silenced and antibodies produced by such mice are described in U.S. Pat. Nos. 7,541,513 and 8,367,888. Recombinant production of heavy chain-only antibodies in mice and rats has been reported, for example, in WO2006008548; U.S. Application Publication No. 20100122358; Nguyen et al., 2003, *Immunology;* 109(1), 93-101; Briiggemann et al., *Crit. Rev. Immunol.;* 2006, 26(5):377-90; and Zou et al., 2007, *J Exp Med;* 204(13): 3271-3283. The production of knockout rats via embryo microinjections of zinc-finger nucleases is described in Geurts et al., 2009, *Science,* 325(5939):433. Soluble heavy chain-only antibodies and transgenic rodents comprising a heterologous heavy chain locus producing such antibodies are described in U.S. Pat. Nos. 8,883,150 and 9,365,655. CAR-T structures comprising single-domain antibodies as binding (targeting) domains are described, for example, in Iri-Sofia et al., 2011, *Experimental Cell Research* 317:2630-2641 and Jamnani et al., 2014, *Biochim Biophys Acta,* 1840:378-386.

SUMMARY OF THE INVENTION

Aspects of the invention include antibodies that bind to MUC1-C, comprising a heavy chain variable region comprising: (a) a CDR1 sequence comprising two or fewer substitutions in any one of the amino acid sequences of SEQ ID NOs: 1 or 4; and/or (b) a CDR2 sequence comprising two or fewer substitutions in any one of the amino acid sequences of SEQ ID NOs: 2 or 5; and/or (c) a CDR3 sequence comprising two or fewer substitutions in any one of the amino acid sequences of SEQ ID NOs: 3 or 6. In some embodiments, the CDR1, CDR2, and CDR3 sequences are present in a human framework. In some embodiments, an antibody further comprises a heavy chain constant region sequence in the absence of a CH1 sequence.

In some embodiments, an antibody comprises: (a) a CDR1 sequence selected from the group consisting of SEQ ID NOs: 1 and 4; and/or (b) a CDR2 sequence selected from the group consisting of SEQ ID NOs: 2 and 5; and/or (c) a CDR3 sequence selected from the group consisting of SEQ ID NOs: 3 and 6.

In some embodiments, an antibody comprises: (a) a CDR1 sequence selected from the group consisting of SEQ ID NOs: 1 and 4; and (b) a CDR2 sequence selected from the group consisting of SEQ ID NOs: 2 and 5; and (c) a CDR3 sequence selected from the group consisting of SEQ ID NOs: 3 and 6.

In some embodiments, an antibody comprises: (a) a CDR1 sequence of SEQ ID NO: 1, a CDR2 sequence of SEQ ID NO: 2, and a CDR3 sequence of SEQ ID NO: 3; or (b) a CDR1 sequence of SEQ ID NO: 4, a CDR2 sequence of SEQ ID NO: 5, and a CDR3 sequence of SEQ ID NO: 6.

In some embodiments, an antibody comprises a heavy chain variable region having at least 95% sequence identity to any of the sequences of SEQ ID NOs: 7-8. In some embodiments, an antibody comprises a heavy chain variable region sequence selected from the group consisting of SEQ ID NOs: 7-8. In some embodiments, an antibody comprises a heavy chain variable region sequence of SEQ ID NO: 7. In some embodiments, an antibody comprises a heavy chain variable region sequence of SEQ ID NO: 8.

Aspects of the invention include antibodies that bind to MUC1-C, comprising a heavy chain variable region comprising CDR1, CDR2 and CDR3 sequences in a human VH framework, wherein the CDR sequences are sequences having two or fewer substitutions in a CDR sequence selected from the group consisting of SEQ ID NOs: 1-6.

In some embodiments, an antibody comprises a heavy chain variable region comprising CDR1, CDR2 and CDR3 sequences in a human VH framework, wherein the CDR sequences are selected from the group consisting of SEQ ID NOs: 1-6.

Aspects of the invention include antibodies that bind to MUC1-C, comprising a heavy chain variable region comprising: (a) a CDR1 sequence of SEQ ID NO: 1, a CDR2 sequence of SEQ ID NO: 2, and a CDR3 sequence of SEQ ID NO: 3, in a human VH framework; or (b) a CDR1 sequence of SEQ ID NO: 4, a CDR2 sequence of SEQ ID NO: 5, and a CDR3 sequence of SEQ ID NO: 6, in a human VH framework.

In some embodiments, an antibody is in a CAR-T format. In some embodiments, an antibody is multi-specific. In some embodiments, an antibody is bispecific. In some embodiments, an antibody binds to two different MUC1-C proteins. In some embodiments, an antibody binds to two different epitopes on the same MUC1-C protein. In some embodiments, an antibody binds to an effector cell. In some embodiments, an antibody binds to a T-cell antigen. In some embodiments, an antibody binds to CD3.

In some embodiments, an antibody comprises: (a) a heavy chain variable region comprising: (i) a CDR1 sequence of SEQ ID NO: 9, a CDR2 sequence of SEQ ID NO: 10, and a CDR3 sequence of SEQ ID NO: 11, in a human VH framework; or (ii) a CDR1 sequence of SEQ ID NO: 12, a CDR2 sequence of SEQ ID NO: 13, and a CDR3 sequence of SEQ ID NO: 14, in a human VH framework; and (b) a light chain variable region comprising a CDR1 sequence of SEQ ID NO: 15, a CDR2 sequence of SEQ ID NO: 16, and a CDR3 sequence of SEQ ID NO: 17, in a human VL framework.

In some embodiments, an antibody comprises: (a) a heavy chain variable region comprising: (i) a heavy chain variable region sequence having at least 95% sequence identity to SEQ ID NO: 18; or (ii) a heavy chain variable region sequence having at least 95% sequence identity to SEQ ID NO: 19; and (b) a light chain variable region sequence having at least 95% sequence identity to SEQ ID NO: 20.

In some embodiments, an antibody comprises: (a) a heavy chain variable region comprising: (i) a heavy chain variable region sequence comprising SEQ ID NO: 18; or (ii) a heavy chain variable region sequence comprising SEQ ID NO: 19; and (b) a light chain variable region sequence comprising SEQ ID NO: 20.

Aspects of the invention include bispecific three-chain antibody-like molecules (TCAs) that binds to MUC1-C and CD3, comprising: (a) a first polypeptide consisting of SEQ ID NO: 32; (b) a second polypeptide selected from the group consisting of: SEQ ID NO: 33 and SEQ ID NO: 42; and (c) a third polypeptide selected from the group consisting of: SEQ ID NO: 34, SEQ ID NO: 35, SEQ ID NO: 36, SEQ ID NO: 37, SEQ ID NO: 38, and SEQ ID NO: 39.

Aspects of the invention include CAR-T cells comprising a CAR comprising an extracellular antigen-binding domain that binds to MUC1-C, comprising a heavy chain variable region comprising: (a) a CDR1 sequence of SEQ ID NO: 1, a CDR2 sequence of SEQ ID NO: 2, and a CDR3 sequence of SEQ ID NO: 3; or (b) a CDR1 sequence of SEQ ID NO: 4, a CDR2 sequence of SEQ ID NO: 5, and a CDR3 sequence of SEQ ID NO: 6. In some embodiments, the extracellular antigen-binding domain that binds to MUC1-C comprises a heavy chain variable region having at least 95% sequence identity to any of the sequences of SEQ ID NOs: 7-8. In some embodiments, the extracellular antigen-binding domain that binds to MUC1-C comprises a heavy chain variable region sequence selected from the group consisting of SEQ ID NOs: 7-8. In some embodiments, the extracellular antigen-binding domain that binds to MUC1-C comprises a heavy chain variable region sequence of SEQ ID NO: 7. In some embodiments, the extracellular antigen-binding domain that binds to MUC1-C comprises a heavy chain variable region sequence of SEQ ID NO: 8.

Aspects of the invention include pharmaceutical compositions comprising an antibody as described herein, or a CAR-T cell as described herein.

Aspects of the invention include methods for the treatment of a disorder characterized by expression of MUC1-C, comprising administering to a subject with said disorder an antibody as described herein, a CAR-T cell as described herein, or a pharmaceutical composition as described herein. In some embodiments, the disorder is a cancer. In some embodiments, the cancer is a carcinoma. In some embodiments, the carcinoma is an adenocarcinoma or a squamous cell carcinoma. In some embodiments, the carcinoma is selected from the group consisting of: breast, non-small cell lung (NSCL), small cell lung (SSC), mesothelioma, renal cell, colorectal, ovarian, head and neck squamous cell, nasopharyngeal, gastric, prostatic, pancreatic, esophageal, and cervical carcinoma. In some embodiments, the cancer is a hematological cancer. In some embodiments, the hematological cancer is a myeloma. In some embodiments, the myeloma is multiple myeloma (MM). In some embodiments, the hematological cancer is a leukemia. In some embodiments, the leukemia is chronic myeloid leukemia (CML). In some embodiments, the hematological cancer is a lymphoma.

Aspects of the invention include polynucleotides encoding an antibody as described herein, or a CAR of a CAR-T cell as described herein.

Aspects of the invention include vectors comprising the polynucleotide as described herein.

Aspects of the invention include cells comprising the vectors as described herein.

Aspects of the invention include methods of producing an antibody as described herein, the methods comprising growing a cell as described herein under conditions permissive for expression of the antibody, and isolating the antibody from the cell and/or a cell culture medium in which the cell is grown.

Aspects of the invention include methods of making an antibody as described herein, the methods comprising immunizing a UniRat animal with MUC1-C and identifying MUC1-C-binding heavy chain sequences.

Aspects of the invention include methods of treatment, comprising administering to an individual in need an effective dose of an antibody as described herein, a CAR-T cell as described herein, or a pharmaceutical composition as described herein.

Aspects of the invention include use of an antibody as described herein or a CAR-T cell as described herein in the preparation of a medicament for the treatment of a disease or disorder in an individual in need.

Aspects of the invention include kits for treating a disease or disorder in an individual in need, comprising an antibody as described herein, a CAR-T cell as described herein, or a pharmaceutical composition as described herein, and instructions for use. In some embodiments, a kit comprises at least one additional reagent. In some embodiments, the at least one additional reagent comprises a chemotherapeutic drug.

These and further aspects will be further explained in the rest of the disclosure, including the Examples.

BRIEF DESCRIPTION OF THE DRAWINGS

FIG. 1 is a table summarizing MUC1-C binding data for the indicated antibody constructs to MUC1-C+ Raji cells and negative control cells.

FIG. 3 is a table summarizing cell binding EC50 values of the indicated antibody constructs on MUC1-C+ Raji cells.

FIG. 4, Panel B, is a graph showing T-cell activity of Jurkat cells transfected with an anti-MUC1-C CAR construct in accordance with one embodiment of the invention.

FIG. 4, Panel C, is a graph showing T-cell activity of Jurkat cells transfected with an anti-MUC1-C CAR construct in accordance with one embodiment of the invention.

FIG. 5, Panel B, is a bar chart showing the area under curve of the graph shown in FIG. 5, Panel A, for the indicated antibody constructs.

FIG. 6, Panel B, is a bar chart showing the area under curve of the graph shown in FIG. 6, Panel A, for the indicated antibody constructs.

FIG. 7, Panel B, is a line graph showing T-cell persistence in blood measured over time for the indicated antibody constructs.

FIG. 8, Panel B, is a bar chart showing the area under curve of the graph shown in FIG. 6, Panel A, for the indicated antibody constructs.

DETAILED DESCRIPTION OF THE PREFERRED EMBODIMENTS

Figure 2:
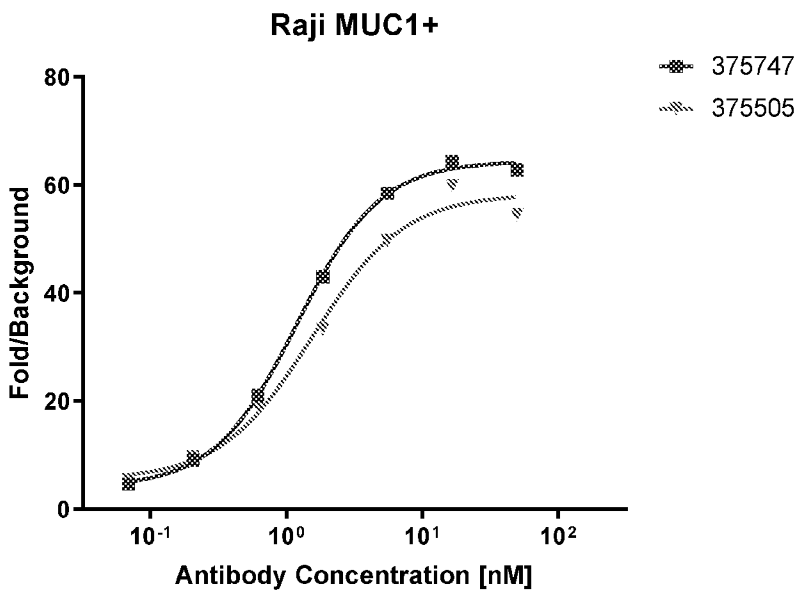
FIG. 2 is a graph showing cell binding as a function of antibody concentration for the indicated antibody constructs, in MUC1-C+ Raji cells.

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless indicated otherwise, antibody residues herein are numbered according to the Kabat numbering system (e.g., Kabat et al., Sequences of Immunological Interest. 5th Ed. Public Health Service, National Institutes of Health, Bethesda, Md. (1991)).

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All references cited throughout the disclosure, including patent applications and publications, are incorporated by reference herein in their entirety.

I. Definitions

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

Antibody residues herein are numbered according to the Kabat numbering system and the EU numbering system. The Kabat numbering system is generally used when referring to a residue in the variable domain (approximately residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies mean residue numbering by the Kabat numbering system. Unless stated otherwise herein, references to residue numbers in the constant domain of antibodies mean residue numbering by the EU numbering system.

Antibodies, also referred to as immunoglobulins, conventionally comprise at least one heavy chain and one light chain, where the amino terminal domain of the heavy and light chains is variable in sequence, hence is commonly referred to as a variable region domain, or a variable heavy (VH) or variable light (VL) domain. The two domains conventionally associate to form a specific binding region, although as will be discussed here, specific binding can also be obtained with heavy chain-only variable sequences, and a variety of non-natural configurations of antibodies are known and used in the art.

A "functional" or "biologically active" antibody or antigen-binding molecule (including heavy chain-only antibodies and multi-specific (e.g., bispecific) three-chain antibody-like molecules (TCAs, described herein) is one capable of exerting one or more of its natural activities in structural, regulatory, biochemical or biophysical events. For example, a functional antibody or other binding molecule, e.g., a TCA, may have the ability to specifically bind an antigen and the binding may in turn elicit or alter a cellular or molecular event such as signal transduction or enzymatic activity. A functional antibody or other binding molecule, e.g., a TCA, may also block ligand activation of a receptor or act as an agonist or antagonist. The capability of an antibody or other binding molecule, e.g., a TCA, to exert one or more of its natural activities depends on several factors, including proper folding and assembly of the polypeptide chains.

The term "antibody" herein is used in the broadest sense and specifically covers monoclonal antibodies, polyclonal antibodies, monomers, dimers, multimers, multispecific antibodies (e.g., bispecific antibodies), heavy chain-only antibodies, three chain antibodies, TCAs, single chain FAT (scFv), nanobodies, etc., and also includes antibody fragments, so long as they exhibit the desired biological activity (Miller et al (2003) Jour. of Immunology 170:4854-4861). Antibodies may be murine, human, humanized, chimeric, or derived from other species.

The term antibody may reference a full-length heavy chain, a full length light chain, an intact immunoglobulin molecule, or an immunologically active portion of any of these polypeptides, i.e., a polypeptide that comprises an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgAl and IgA2) or subclass of immunoglobulin molecule, including engineered subclasses with altered Fc portions that provide for reduced or enhanced effector cell activity. Light chains of the subject antibodies can be kappa light chains (Vkappa) or lambda light chains (Vlambda). The immunoglobulins can be derived from any species. In one aspect, the immunoglobulin is of largely human origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies in accordance with the present invention can be made by the hybridoma method first described by Kohler et al. (1975) *Nature* 256:495, and can also be made via recombinant protein production methods (see, e.g., U.S. Pat. No. 4,816,567), for example.

The term "variable", as used in connection with antibodies, refers to the fact that certain portions of the antibody variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, MD. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity-determining region" or "CDR" (e.g., residues 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hyper-variable loop" residues 26-32 (H1), 53-55 (H2) and 96-101 (H3) in the heavy chain variable domain; Chothia and Lesk *J. Mol. Biol.* 196:901-917 (1987)). In some embodiments, "CDR" means a complementarity-determining region of an antibody as defined in Lefranc, M P et al., IMGT, the International ImMunoGeneTics database, Nucleic Acids Res., 27:209-212 (1999). "Framework Region" or "FR" residues are those variable domain residues other than the hypervariable region/CDR residues as herein defined.

Exemplary CDR designations are shown herein; however, one of skill in the art will understand that a number of definitions of the CDRs are commonly in use, including the Kabat definition (see "Zhao et al. A germline knowledge based computational approach for determining antibody complementarity determining regions." *Mol Immunol.* 2010; 47:694-700), which is based on sequence variability and is the most commonly used. The Chothia definition is based on the location of the structural loop regions (Chothia et al. "Conformations of immunoglobulin hypervariable regions." *Nature.* 1989; 342:877-883). Alternative CDR definitions of interest include, without limitation, those disclosed by Honegger, "Yet another numbering scheme for immunoglobulin variable domains: an automatic modeling and analysis tool." *J Mol Biol.* 2001;309:657-670; Ofran et al. "Automated identification of complementarity determining regions (CDRs) reveals peculiar characteristics of CDRs and B-cell epitopes." *J Immunol.* 2008;181:6230-6235; Almagro "Identification of differences in the specificity-determining residues of antibodies that recognize antigens of different size: implications for the rational design of antibody repertoires." *J Mol Recognit.* 2004;17:132-143; and Padlanet al. "Identification of specificity-determining residues in antibodies." Faseb J. 1995;9:133-139., each of which is herein specifically incorporated by reference.

The terms "heavy chain-only antibody," and "heavy chain antibody" are used interchangeably herein and refer, in the broadest sense, to antibodies, or one or more portions of an antibody, e.g., one or more arms of an antibody, lacking the light chain of a conventional antibody. The terms specifically include, without limitation, homodimeric antibodies comprising the VH antigen-binding domain and the CH2 and CH3 constant domains, in the absence of the CH1 domain; functional (antigen-binding) variants of such antibodies, soluble VH variants, Ig-NAR comprising a homodimer of one variable domain (V-NAR) and five C-like constant domains (C-NAR) and functional fragments thereof; and soluble single domain antibodies (sUniDabs™). In one embodiment, a heavy chain-only antibody is composed of a variable region antigen-binding domain composed of framework 1, CDR1, framework 2, CDR2, framework 3, CDR3, and framework 4. In another embodiment, a heavy chain-only antibody is composed of an antigen-binding domain, at least part of a hinge region and CH2 and CH3 domains. In another embodiment, a heavy chain-only antibody is composed of an antigen-binding domain, at least part of a hinge region and a CH2 domain. In a further embodiment, a heavy chain-only antibody is composed of an antigen-binding domain, at least part of a hinge region and a CH3 domain. Heavy chain-only antibodies in which the CH2 and/or CH3 domain is truncated are also included herein. In a further embodiment, a heavy chain is composed of an antigen binding domain, and at least one CH (CH1, CH2, CH3, or CH4) domain but no hinge region. A heavy chain-only antibody can be in the form of a dimer, in which two heavy chains are disulfide bonded or otherwise, covalently or non-covalently, attached with each other. The heavy chain-only antibody may belong to the IgG subclass, but antibodies belonging to other subclasses, such as IgM, IgA, IgD and IgE subclass, are also included herein. In a particular embodiment, a heavy chain antibody is of the IgG1, IgG2, IgG3, or IgG4 subtype, in particular the IgG1 or IgG4 subtype. In one embodiment, a heavy-chain antibody is of the IgG4 subtype, wherein one or more of the CH domains is modified to alter an effector function of the antibody. In one embodiment, the heavy-chain antibody is of the IgG1 or IgG4 subtype, wherein one or more of the CH domains is modified to alter an effector function of the antibody. Modifications of CH domains that alter effector function are further described herein. Non-limiting examples of heavy-chain antibodies are described, for example, in WO2018/039180, the disclosure of which is incorporated herein by reference in its entirety.

In some embodiments, the heavy chain-only antibodies herein are used as a binding (targeting) domain of a chimeric antigen receptor (CAR). The definition specifically includes human heavy chain-only antibodies produced by human immunoglobulin transgenic rats (UniRat™), called UniAbs™. The variable regions (VH) of UniAbs™ are called UniDabs™, and are versatile building blocks that can be linked to Fc regions or serum albumin for the development of novel therapeutics with multi-specificity, increased potency and extended half-life. Since the homodimeric UniAbs™ lack a light chain and thus a VL domain, the antigen is recognized by one single domain, i.e., the variable domain of the heavy chain of a heavy-chain antibody (VH or VHH).

An "intact antibody chain" as used herein is one comprising a full length variable region and a full length constant region (Fc). An intact "conventional" antibody comprises an intact light chain and an intact heavy chain, as well as a light chain constant domain (CL) and heavy chain constant domains, CH1 hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the Fc (constant domain) of their heavy chains, antibodies and various antigen-binding proteins can be provided as different classes. There are five major classes of heavy chain Fc regions: IgA, IgD, IgE, IgG, and IgM, and several of these may be further divided into "subclasses" (isotypes), e.g., IgG1, IgG2, IgG3, IgG4, IgA, and IgA2. The Fc constant domains that correspond to the different classes of antibodies may be referenced as $\alpha$, $\delta$, $\varepsilon$, $\gamma$, and $\mu$, respectively. The subunit structures and three-dimensional configurations of different classes of immunoglobulins are well known. Ig forms include hinge-modifications or hingeless forms (Roux et al (1998) J.

Immunol. 161:4083-4090; Lund et al (2000) Eur. J. Biochem. 267:7246-7256; US 2005/0048572; US 2004/0229310). The light chains of antibodies from any vertebrate species can be assigned to one of two types, called κ (kappa) and λ (lambda), based on the amino acid sequences of their constant domains. Antibodies in accordance with embodiments of the invention can comprise kappa light chain sequences or lambda light chain sequences.

A "functional Fc region" possesses an "effector function" of a native-sequence Fc region. Non-limiting examples of effector functions include C1q binding; CDC; Fc-receptor binding; ADCC; ADCP; down-regulation of cell-surface receptors (e.g., B-cell receptor), etc. Such effector functions generally require the Fc region to interact with a receptor, e.g., the FcγRI; FcγRIIA; FcγRIHB1; FcγRIIB2; FcγRIIIA; FcγRIIIB receptors, and the low affinity FcRn receptor; and can be assessed using various assays known in the art. A "dead" or "silenced" Fc is one that has been mutated to retain activity with respect to, for example, prolonging serum half-life, but which does not activate a high affinity Fc receptor, or which has a reduced affinity to an Fc receptor.

A "native-sequence Fc region" comprises an amino acid sequence identical to the amino acid sequence of an Fc region found in nature. Native-sequence human Fc regions include, for example, a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce FcγRI binding at EU index positions 234, 235, and 237 (see Duncan et al., (1988) Nature 332:563). Two amino acid substitutions in the complement C1 q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 or IgG2 residues at positions 233-236 and IgG4 residues at positions 327, 330 and 331 greatly reduces ADCC and CDC (see, for example, Armour KL. et al., 1999 Eur J Immunol. 29(8): 2613-24; and Shields R L. et al., 2001. J Biol Chem. 276(9):6591-604). The human IgG4 Fc amino acid sequence (UniProtKB No. P01861) is provided herein as SEQ ID NO: 22. Silenced IgG1 is described, for example, in Boesch, A. W., et al., "Highly parallel characterization of IgG Fc binding interactions." MAbs, 2014. 6(4): p. 915-27, the disclosure of which is incorporated herein by reference in its entirety.

Other Fc variants are possible, including, without limitation, one in which a region capable of forming a disulfide bond is deleted, or in which certain amino acid residues are eliminated at the N-terminal end of a native Fc, or a methionine residue is added thereto. Thus, in some embodiments, one or more Fc portions of an antibody can comprise one or more mutations in the hinge region to eliminate disulfide bonding. In yet another embodiment, the hinge region of an Fc can be removed entirely. In still another embodiment, an antibody can comprise an Fc variant.

Further, an Fc variant can be constructed to remove or substantially reduce effector functions by substituting (mutating), deleting or adding amino acid residues to effect complement binding or Fc receptor binding. For example, and not limitation, a deletion may occur in a complement-binding site, such as a Clq-binding site. Techniques for preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

In some embodiments, an antibody comprises a variant human IgG4 CH3 domain sequence comprising a T366W mutation, which can optionally be referred to herein as an IgG4 CH3 knob sequence. In some embodiments, an antibody comprises a variant human IgG4 CH3 domain sequence comprising a T366S mutation, an L368A mutation, and a Y407V mutation, which can optionally be referred to herein as an IgG4 CH3 hole sequence. The IgG4 CH3 mutations described herein can be utilized in any suitable manner so as to place a "knob" on a first heavy chain constant region of a first monomer in an antibody dimer, and a "hole" on a second heavy chain constant region of a second monomer in an antibody dimer, thereby facilitating proper pairing (heterodimerization) of the desired pair of heavy chain polypeptide subunits in the antibody.

In some embodiments, an antibody comprises a heavy chain polypeptide subunit comprising a variant human IgG4 Fc region comprising an S228P mutation, an F234A mutation, an L235A mutation, and a T366W mutation (knob). In some embodiments, and antibody comprises a heavy chain polypeptide subunit comprising a variant human IgG4 Fc region comprising an S228P mutation, an F234A mutation, an L235A mutation, a T366S mutation, an L368A mutation, and a Y407V mutation (hole).

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, an antibody having an Fc region according to this invention can comprise an antibody with or without K447.

Aspects of the invention include antibodies comprising a heavy chain-only variable region in a monovalent or bivalent configuration. As used herein, the term "monovalent configuration" as used in reference to a heavy chain-only variable region domain means that only one heavy chain-only variable region domain is present, having a single binding site. In contrast, the term "bivalent configuration" as used in reference to a heavy chain-only variable region domain means that two heavy chain-only variable region domains are present (each having a single binding site), and are connected by a linker sequence. Non-limiting examples of linker sequences are discussed further herein, and include, without limitation, GS linker sequences of various lengths. When a heavy chain-only variable region is in a bivalent configuration, each of the two heavy chain-only variable region domains can bind to the same antigen, or to different antigens (e.g., to different epitopes on the same protein; to two different proteins, etc.). However, unless specifically noted otherwise, a heavy chain-only variable region denoted as being in a "bivalent configuration" is understood to contain two identical heavy chain-only variable region domains, connected by a linker sequence, wherein each of the two identical heavy chain-only variable region domains binds to the same target antigen.

Aspects of the invention include antibodies having multispecific configurations, which include, without limitation, bispecific, trispecific, etc. A large variety of methods and protein configurations are known and used in bispecific monoclonal antibodies (BsMAB), tri-specific antibodies, etc.

Various methods for the production of multivalent artificial antibodies have been developed by recombinantly fusing variable domains of two or more antibodies. In some embodiments, a first and a second antigen-binding domain on a polypeptide are connected by a polypeptide linker. One non-limiting example of such a polypeptide linker is a GS linker, having an amino acid sequence of four glycine residues, followed by one serine residue, and wherein the sequence is repeated n times, where n is an integer ranging from 1 to about 10, such as 2, 3, 4, 5, 6, 7, 8, or 9. Non-limiting examples of such linkers include GGGGS (SEQ ID NO: 40) (n=1) and GGGGSGGGGS (SEQ ID NO: 41) (n=2). Other suitable linkers can also be used, and are described, for example, in Chen et al., Adv Drug Deliv Rev. 2013 Oct. 15; 65(10): 1357-69, the disclosure of which is incorporated herein by reference in its entirety.

The term "three-chain antibody-like molecule" or "TCA" is used herein to refer to antibody-like molecules comprising, consisting essentially of, or consisting of three polypeptide subunits, two of which comprise, consist essentially of, or consist of one heavy and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy-chain only antibody comprising an Fc portion comprising CH2 and/or CH3 and/or CH4 domains, in the absence of a CH1 domain, and one or more antigen binding domains (e.g., two antigen binding domains) that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_HDJ_H$, $V_LDJ_H$, $V_HJ_L$, or $V_LJ_L$ gene segments.

A TCA binding compound makes use of a "heavy chain only antibody" or "heavy chain antibody" or "heavy chain polypeptide" which, as used herein, mean a single chain antibody comprising heavy chain constant regions CH2 and/or CH3 and/or CH4 but no CH1 domain. In one embodiment, the heavy chain antibody is composed of an antigen-binding domain, at least part of a hinge region and CH2 and CH3 domains. In another embodiment, the heavy chain antibody is composed of an antigen-binding domain, at least part of a hinge region and a CH2 domain. In a further embodiment, the heavy chain antibody is composed of an antigen-binding domain, at least part of a hinge region and a CH3 domain. Heavy chain antibodies in which the CH2 and/or CH3 domain is truncated are also included herein. In a further embodiment, the heavy chain is composed of an antigen binding domain, and at least one CH (CH1, CH2, CH3, or CH4) domain but no hinge region. The heavy chain only antibody can be in the form of a dimer, in which two heavy chains are disulfide bonded or otherwise covalently or non-covalently attached to each other, and can optionally include an asymmetric interface (e.g., a knobs-in-holes (KiH) interface) between one or more of the CH domains to facilitate proper pairing between polypeptide chains. The heavy-chain antibody may belong to the IgG subclass, but antibodies belonging to other subclasses, such as IgM, IgA, IgD and IgE subclass, are also included herein. In a particular embodiment, the heavy chain antibody is of the IgG1, IgG2, IgG3, or IgG4 subtype, in particular the IgG1 subtype or the IgG4 subtype. Non-limiting examples of a TCA binding compound are described in, for example, WO2017/223111 and WO2018/052503, the disclosures of which are incorporated herein by reference in their entirety.

Heavy-chain antibodies constitute about one fourth of the IgG antibodies produced by the camelids, e.g., camels and llamas (Hamers-Casterman C., et al. Nature. 363, 446-448 (1993)). These antibodies are formed by two heavy chains but are devoid of light chains. As a consequence, the variable antigen binding part is referred to as the VHH domain and it represents the smallest naturally occurring, intact, antigen-binding site, being only around 120 amino acids in length (Desmyter, A., et al. J. Biol. Chem. 276, 26285-26290 (2001)). Heavy chain antibodies with a high specificity and affinity can be generated against a variety of antigens through immunization (van der Linden, R. H., et al. Biochim. Biophys. Acta. 1431, 37-46 (1999)) and the VHH portion can be readily cloned and expressed in yeast (Frenken, L. G. J., et al. J. Biotechnol. 78, 11-21 (2000)). Their levels of expression, solubility and stability are significantly higher than those of classical F(ab) or Fv fragments (Ghahroudi, M. A. et al. FEBS Lett. 414, 521-526 (1997)). Sharks have also been shown to have a single VH-like domain in their antibodies, termed VNAR. (Nuttall et al. Eur. J. Biochem. 270, 3543-3554 (2003); Nuttall et al. Function and Bioinformatics 55, 187-197 (2004); Dooley et al., Molecular Immunology 40, 25-33 (2003)).

The term "MUC1" as used herein refers to a membrane-bound protein that is a member of the mucin family. Mucins are O-glycosylated proteins that play an essential role in forming protective mucous barriers on epithelial surfaces, and also play a role in intracellular signaling. MUC1 is expressed on the apical surface of epithelial cells that line the mucosal surfaces of many different tissues.

The term "MUC1-N" refers to the N-terminal, or alpha subunit, of MUC1, and the term "MUC1-C" refers to the C-terminal, or beta subunit, or MUC1. In the case of human MUC1 (UniProt P15941), MUC1-N includes amino acid residues 24-1,097 of MUC1, and MUC1-C includes amino acid residues 1,098-1,255 of MUC1 (UniProt P15941).

The terms "MUC1", "MUC1-N" and "MUC1-C" include a MUC1, MUC1-N or MUC1-C protein of any human and non-human animal species, and specifically include human MUC1, MUC1-N and MUC1-C, as well as MUC1, MUC1-N and MUC1-C of non-human mammals.

The term "human MUC1" as used herein includes any variants, isoforms and species homologs of human MUC1 (UniProt P15941), regardless of its source or mode of preparation. Thus, "human MUC1" includes human MUC1 naturally expressed by cells and MUC1 expressed on cells transfected with the human MUC1 gene.

The terms "anti-MUC1-C heavy chain-only antibody," "MUC1-C heavy chain-only antibody," "anti-MUC1-C heavy chain antibody" and "MUC1-C heavy chain antibody" are used herein interchangeably to refer to a heavy chain-only antibody as hereinabove defined, immunospecifically binding to MUC1-C, including human MUC1-C, as hereinabove defined. The definition includes, without limitation, human heavy chain antibodies produced by transgenic animals, such as transgenic rats or transgenic mice expressing human immunoglobulin, including UniRats™ producing human anti-MUC1-C UniAb™ antibodies, as hereinabove defined.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Antibodies of the invention include multi-specific antibodies. Multi-specific antibodies have more than one binding specificity. The term "multi-specific" specifically includes "bispecific" and "trispecific," as well as higher-order independent specific binding affinities, such as higher-order polyepitopic specificity, as well as tetravalent antibodies and antibody fragments. The terms "multi-specific antibody," "multi-specific heavy chain-only antibody," "multi-specific heavy chain antibody," and "multi-specific UniAb™" are used herein in the broadest sense and cover all antibodies with more than one binding specificity. The multi-specific heavy chain anti-MUC1-C antibodies of the present invention specifically include antibodies immunospecifically binding to two or more non-overlapping epitopes on a MUC1-C protein, such as a human MUC1-C (i.e., bivalent and biparatopic). The multi-specific heavy chain anti-MUC1-C antibodies of the present invention also specifically include antibodies immunospecifically binding to an epitope on a MUC1-C protein, such as human MUC1-C, and to an epitope on a different protein, such as, for example, a CD3 protein, such as human CD3 (i.e., bivalent and biparatopic). The multi-specific heavy chain anti-MUC1-C antibodies of the present invention also specifically include antibodies immunospecifically binding to two or more non-overlapping or partially overlapping epitopes on a MUC1-C protein, such as a human MUC1-C protein, and to an epitope on a different protein, such as, for example, a CD3 protein, such as human CD3 protein (i.e., trivalent and biparatopic).

Antibodies of the invention include monospecific antibodies, having one binding specificity. Monospecific antibodies specifically include antibodies comprising a single binding specificity, as well as antibodies comprising more than one binding unit having the same binding specificity. The terms "monospecific antibody," "monospecific heavy chain-only antibody," "monospecific heavy chain antibody," and "monospecific UniAb™" are used herein in the broadest sense and cover all antibodies with one binding specificity. The monospecific heavy chain anti-MUC1-C antibodies of the present invention specifically include antibodies immunospecifically binding to one epitope on a MUC1-C protein, such as a human MUC1-C protein (monovalent and monospecific). The monospecific heavy chain anti-MUC1-C antibodies of the present invention also specifically include antibodies having more than one binding unit (e.g., multivalent antibodies) immunospecifically binding to an epitope on a MUC1-C protein, such as human MUC1-C. For example, a monospecific antibody in accordance with embodiments of the invention can include a heavy chain variable region comprising two antigen-binding domains, wherein each antigen-binding domain binds to the same epitope on a MUC1-C protein (i.e., bivalent and monospecific).

An "epitope" is the site on the surface of an antigen molecule to which a single antibody molecule binds. Generally, an antigen has several or many different epitopes and reacts with many different antibodies. The term specifically includes linear epitopes and conformational epitopes.

"Epitope mapping" is the process of identifying the binding sites, or epitopes, of antibodies on their target antigens. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure.

"Polyepitopic specificity" refers to the ability to specifically bind to two or more different epitopes on the same or different target(s). As noted above, the present invention specifically includes anti-MUC1-C heavy chain antibodies with polyepitopic specificities, i.e., anti-MUC1-C heavy chain antibodies binding to one or more non-overlapping epitopes on a MUC1-C protein, such as a human MUC1-C; and anti-MUC1-C heavy chain antibodies binding to one or more epitopes on a MUC1-C protein and to an epitope on a different protein, such as, for example, a CD3 protein. The term "non-overlapping epitope(s)" or "non-competitive epitope(s)" of an antigen is defined herein to mean epitope(s) that are recognized by one member of a pair of antigen-specific antibodies but not the other member. Pairs of antibodies, or antigen-binding regions targeting the same antigen on a multi-specific antibody, recognizing non-overlapping epitopes, do not compete for binding to that antigen and are able to bind that antigen simultaneously.

An antibody binds "essentially the same epitope" as a reference antibody, when the two antibodies recognize identical or sterically overlapping epitopes. The most widely used and rapid methods for determining whether two epitopes bind to identical or sterically overlapping epitopes are competition assays, which can be configured in all number of different formats, using either labeled antigen or labeled antibody. Usually, the antigen is immobilized on a 96-well plate, and the ability of unlabeled antibodies to block the binding of labeled antibodies is measured using radioactive or enzyme labels.

The term "valent" as used herein refers to a specified number of binding sites in an antibody molecule.

A "monovalent" antibody has one binding site. Thus, a monovalent antibody is also monospecific.

A "multi-valent" antibody has two or more binding sites. Thus, the terms "bivalent", "trivalent", and "tetravalent" refer to the presence of two binding sites, three binding sites, and four binding sites, respectively. Thus, a bispecific antibody according to the invention is at least bivalent and may be trivalent, tetravalent, or otherwise multi-valent. A bivalent antibody in accordance with embodiments of the invention may have two binding sites to the same epitope (i.e., bivalent, monoparatopic), or to two different epitopes (i.e., bivalent, biparatopic).

A large variety of methods and protein configurations are known and used for the preparation of bispecific monoclonal antibodies (BsMAB), tri-specific antibodies, and the like.

The term "three-chain antibody like molecule" or "TCA" is used herein to refer to antibody-like molecules comprising, consisting essentially of, or consisting of three polypeptide subunits, two of which comprise, consist essentially of, or consist of one heavy chain and one light chain of a monoclonal antibody, or functional antigen-binding fragments of such antibody chains, comprising an antigen-binding region and at least one CH domain. This heavy chain/light chain pair has binding specificity for a first antigen. The third polypeptide subunit comprises, consists essentially of, or consists of a heavy chain-only antibody comprising an Fc portion comprising CH2 and/or CH3 and/or CH4 domains, in the absence of a CH1 domain, and an antigen binding domain that binds an epitope of a second antigen or a different epitope of the first antigen, where such binding domain is derived from or has sequence identity with the variable region of an antibody heavy or light chain. Parts of such variable region may be encoded by $V_H$ and/or $V_L$ gene segments, D and $J_H$ gene segments, or $J_L$ gene segments. The variable region may be encoded by rearranged $V_HDJ_H$, $V_LDJ_H$, $V_HJ_L$, or $V_LJ_L$ gene segments. A TCA protein makes use of a heavy chain-only antibody as hereinabove defined.

The term "chimeric antigen receptor" or "CAR" is used herein in the broadest sense to refer to an engineered receptor, which grafts a desired binding specificity (e.g., the antigen-binding region of a monoclonal antibody or other ligand) to membrane-spanning and intracellular-signaling domains. Typically, the receptor is used to graft the specificity of a monoclonal antibody onto a T-cell to create a chimeric antigen receptors (CAR). (*J Natl Cancer Inst,* 2015; 108(7):dvj439; and Jackson et al., *Nature Reviews Clinical Oncology,* 2016; 13:370-383). CAR-T cells are T-cells that have been genetically engineered to produce an artificial T-cell receptor for use in immunotherapy. In one embodiment, "CAR-T cell" means a therapeutic T-cell expressing a transgene encoding one or more chimeric antigen receptors comprised minimally of an extracellular domain, a transmembrane domain, and at least one cytosolic domain.

The term "human antibody" is used herein to include antibodies having variable and constant regions derived from human germline immunoglobulin sequences. The human antibodies herein may include amino acid residues not encoded by human germline immunoglobulin sequences, e.g., mutations introduced by random or site-specific mutagenesis in vitro or by somatic mutation in vivo. The term "human antibody" specifically includes heavy chain-only antibodies having human heavy chain variable region sequences, produced by transgenic animals, such as transgenic rats or mice, in particular UniAbs™ produced by UniRats™, as defined above.

By a "chimeric antibody" or a "chimeric immunoglobulin" is meant an immunoglobulin molecule comprising amino acid sequences from at least two different Ig loci, e.g., a transgenic antibody comprising a portion encoded by a human Ig locus and a portion encoded by a rat Ig locus. Chimeric antibodies include transgenic antibodies with non-human Fc-regions or artificial Fc-regions, and human idiotypes. Such immunoglobulins can be isolated from animals of the invention that have been engineered to produce such chimeric antibodies.

As used herein, the term "effector cell" refers to an immune cell which is involved in the effector phase of an immune response, as opposed to the cognitive and activation phases of an immune response. Some effector cells express specific Fc receptors and carry out specific immune functions. In some embodiments, an effector cell such as a natural killer cell is capable of inducing antibody-dependent cellular cytotoxicity (ADCC). For example, monocytes and macrophages, which express FcR, are involved in specific killing of target cells and presenting antigens to other components of the immune system, or binding to cells that present antigens. In some embodiments, an effector cell may phagocytose a target antigen or target cell.

"Human effector cells" are leukocytes which express receptors such as T-cell receptors or FcRs and perform effector functions. Preferably, the cells express at least FcγRIII and perform ADCC effector function. Examples of human leukocytes which mediate ADCC include natural killer (NK) cells, monocytes, cytotoxic T-cells and neutrophils; with NK cells being preferred. The effector cells may be isolated from a native source thereof, e.g., from blood or PBMCs as described herein.

The term "immune cell" is used herein in the broadest sense, including, without limitation, cells of myeloid or lymphoid origin, for instance lymphocytes (such as B-cells and T-cells including cytolytic T-cells (CTLs)), killer cells, natural killer (NK) cells, macrophages, monocytes, eosinophils, polymorphonuclear cells, such as neutrophils, granulocytes, mast cells, and basophils.

Antibody "effector functions" refer to those biological activities attributable to the Fc region (a native sequence Fc region or amino acid sequence variant Fc region) of an antibody. Examples of antibody effector functions include C1 q binding; complement dependent cytotoxicity (CDC); Fc receptor binding; antibody-dependent cell-mediated cytotoxicity (ADCC); phagocytosis; down regulation of cell surface receptors (e.g., B-cell receptor; BCR), etc.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g., as described in Gazzano-Santoro et al., *J. Immunol. Methods* 202:163 (1996), may be performed.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art. Low-affinity antibodies generally bind antigen slowly and tend to dissociate readily, whereas high-affinity antibodies generally bind antigen faster and tend to remain bound.

As used herein, the "Kd" or "Kd value" refers to a dissociation constant determined by BioLayer Interferometry, using an Octet QK384 instrument (Fortebio Inc., Menlo Park, Calif.) in kinetics mode. For example, anti-mouse Fc sensors are loaded with mouse-Fc fused antigen and then dipped into antibody-containing wells to measure concentration dependent association rates (kon). Antibody dissociation rates (koff) are measured in the final step, where the sensors are dipped into wells containing buffer only. The Kd is the ratio of koff/kon. (For further details see, Concepcion, J, et al., *Comb Chem High Throughput Screen,* 12(8), 791-800, 2009).

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The term "characterized by expression of MUC1-C" broadly refers to any disease or disorder in which MUC1-C expression is associated with or involved with one or more pathological processes that are characteristic of the disease or disorder. Such disorders include, but are not limited to, solid tumors and hematological malignancies, such as those described further herein. In some embodiments, a disease or disorder characterized by expression of MUC1-C includes cancers of epithelial origin, i.e., carcinomas, including adenocarcinomas and squamous cell carcinomas. Non-limiting examples of carcinomas include: breast, non-small cell lung (NSCL), small cell lung (SSC), mesothelioma, renal cell, colorectal, ovarian, head and neck squamous cell, nasopharyngeal, gastric, prostatic, pancreatic, esophageal, and cervical carcinomas. In some embodiments, a disease or disorder characterized by expression of MUC1-C includes hematological malignancies, i.e., myelomas, leukemias, and lymphomas. Non-limiting examples of hematological malignancies include multiple myeloma and chronic myeloid leukemia (CML).

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g., mouse, rat, etc.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores. A "frozen" formulation is one at a temperature below 0° C.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein Drug Delivery, 247-301. Vincent Lee Ed., Marcel Dekker, Inc., New York, N.Y., Pubs. (1991) and Jones. A. Adv. Drug Delivery Rev. 10: 29-90) (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis;

SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g., Asn deamidation), oxidation (e.g., Met oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, etc.

II. Detailed Description

Anti-MUC1-C Antibodies

The present invention provides a family of closely related antibodies that bind to human MUC1-C. The antibodies of this family comprise a set of CDR sequences as defined herein and shown in Table 1, and are exemplified by the provided heavy chain CDR1, CDR2 and CDR3 sequences set forth in Table 2, and the heavy chain variable region (VH) sequences of SEQ ID NOs: 7 and 8 set forth in Table 3. The family of antibodies provides a number of benefits that contribute to utility as clinically therapeutic agent(s). The antibodies include members with a range of binding affinities, allowing the selection of a specific sequence with a desired binding affinity.

TABLE 1

Anti-MUC1-C heavy chain antibody unique CDR amino acid sequences.

| SEQ_aa_CDR1 | SEQ_aa_CDR2 | SEQ_aa_CDR3 |
|---|---|---|
| GFAFSGNS (SEQ ID NO: 1) | ITSSGRSI (SEQ ID NO: 2) | ATGGTGTSLFDY (SEQ ID NO: 3) |
| GFTFSSHS (SEQ ID NO: 4) | ISSSSNIK (SEQ ID NO: 5) | ATGGTGITVLDY (SEQ ID NO: 6) |

TABLE 2

Anti-MUC1-C heavy chain antibody CDR1, CDR2 and CDR3 amino acid sequences.

| Clone ID # | SEQ_aa_CDR1 | SEQ_aa_CDR2 | SEQ_aa_CDR3 |
|---|---|---|---|
| 375747 | GFAFSGNS (SEQ ID NO: 1) | ITSSGRSI (SEQ ID NO: 2) | ATGGTGTSLFDY (SEQ ID NO: 3) |
| 375505 | GFTFSSHS (SEQ ID NO: 4) | ISSSSNIK (SEQ ID NO: 5) | ATGGTGITVLDY (SEQ ID NO: 6) |

TABLE 3

Anti-MUC1-C heavy chain antibody variable domain amino acid sequences.

| Clone ID # | SEQ_aa_FR1_FR4 | SEQ ID NO. |
|---|---|---|
| 375747 | EVQLVESGGGLVQPGGSLRLSCTASGFAF SGNSMNWVRQAPGKGLEWVAFITSSGRSI KYADSVKGRFTISRDNAKNSLYLQMNTLR DEDTALYYCATGGTGTSLFDYRGQGTLVT VSS | 7 |

TABLE 3-continued

Anti-MUC1-C heavy chain antibody variable domain amino acid sequences.

| Clone ID # | SEQ_aa_FR1_FR4 | SEQ ID NO. |
|---|---|---|
| 375505 | EVQLVESGGGLVQPGGSLRLSCAASGFTF SSHSMNWVRQAPGKGLEWVSFISSSSNIK KYADSVKGRFTISRDNAKNSLFLQMNSLR DEDTAVYYCATGGTGITVLDYRGQGTLVT VSS | 8 |

Figure 4:
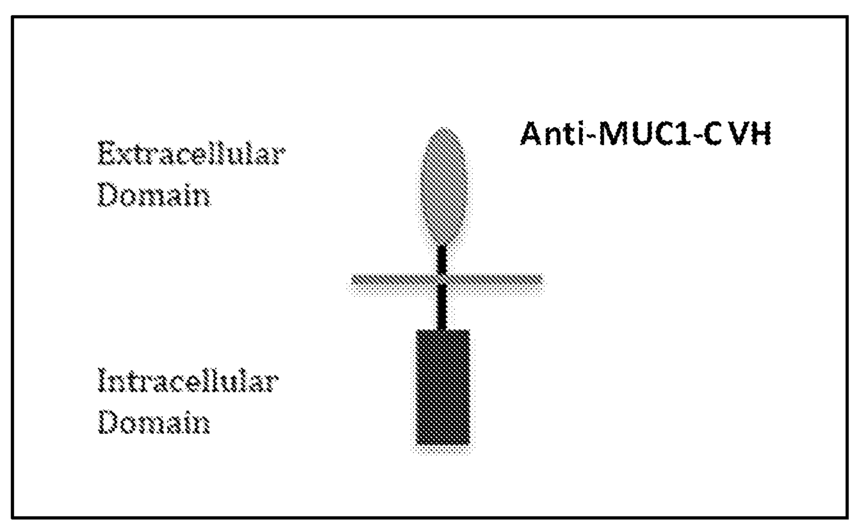
FIG. 4, Panel A, is a schematic diagram of a CAR-T structure comprising an anti-MUC1-C extracellular binding domain.
Figure 4:
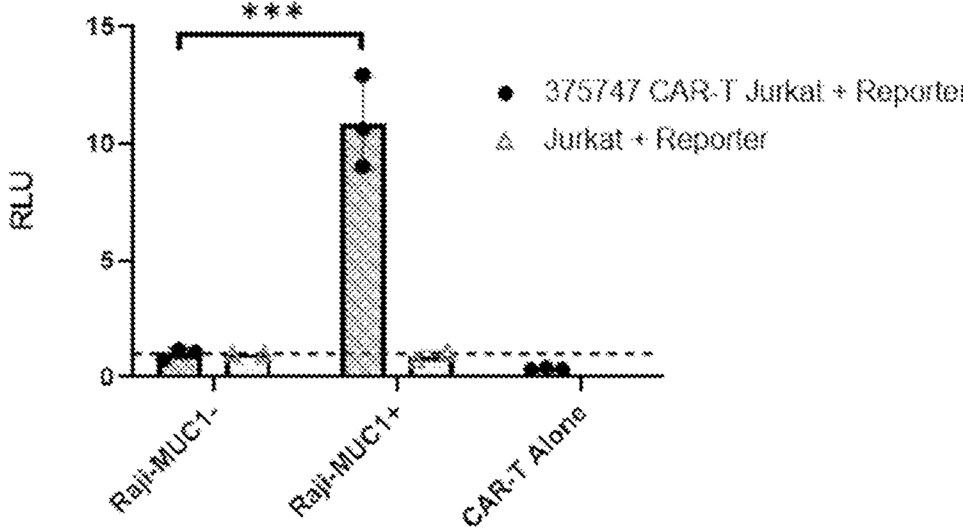

A suitable antibody may be selected from those provided herein for development and therapeutic or other use, including, without limitation, use as a bispecific antibody, or part of a CAR-T structure, as shown, for example, in FIG. 4.

Determination of affinity for a candidate protein can be performed using methods known in the art, such as Biacore measurements. Members of the antibody family may have an affinity for MUC1-C with a Kd of from about $10^{-6}$ to around about $10^{-11}$, including without limitation: from about $10^{-6}$ to around about $10^{-10}$; from about $10^{-6}$ to around about $10^{-9}$; from about $10^{-6}$ to around about $10^{-8}$; from about $10^{-8}$ to around about $10^{-11}$; from about $10^{-8}$ to around about $10^{-10}$; from about $10^{-8}$ to around about $10^{-9}$; from about $10^{-9}$ to around about $10^{-11}$; from about $10^{-9}$ to around about $10^{-10}$; or any value within these ranges. The affinity selection may be confirmed with a biological assessment for modulating, e.g., blocking, a MUC1-C biological activity, including in vitro assays, pre-clinical models, and clinical trials, as well as assessment of potential toxicity.

Members of the antibody family herein are not cross-reactive with the MUC1-C protein of Cynomolgus macaque, but can be engineered to provide cross-reactivity with the MUC1-C protein of Cynomolgus macaque, or with the MUC1-C of any other animal species, if desired.

The family of MUC1-C-specific antibodies herein comprises a VH domain, comprising CDR1, CDR2 and CDR3 sequences in a human VH framework. The CDR sequences may be situated, as an example, in the region of around amino acid residues 26-33; 51-58; and 97-116 for CDR1, CDR2 and CDR3, respectively, of the provided exemplary variable region sequences set forth in SEQ ID NOs: 7-8. It will be understood by one of ordinary skill in the art that the CDR sequences may be in different positions if a different framework sequence is selected, although generally the order of the sequences will remain the same.

In a particular embodiment, an anti-MUC1-C antibody comprises a CDR1 sequence of any one of SEQ ID NOs: 1 or 4. In a particular embodiment, the CDR1 sequence comprises SEQ ID NO: 1. In a particular embodiment, the CDR1 sequence comprises SEQ ID NO: 4.

In a particular embodiment, an anti-MUC1-C antibody comprises a CDR2 sequence of any one of SEQ ID NOs: 2 or 5. In a particular embodiment, the CDR2 sequence comprises SEQ ID NO: 2. In a particular embodiment, the CDR2 sequence comprises SEQ ID NO: 5.

In a particular embodiment, an anti-MUC1-C antibody comprises a CDR3 sequence of any one of SEQ ID NOs: 3 or 6. In a particular embodiment, the CDR3 sequence comprises SEQ ID NO: 3. In a particular embodiment, the CDR2 sequence comprises SEQ ID NO: 6.

In a further embodiment, an anti-MUC1-C heavy chain-only antibody comprises the CDR1 sequence of SEQ ID NO: 1; the CDR2 sequence of SEQ ID NO: 2; and the CDR3 sequence of SEQ ID NO: 3.

In a further embodiment, an anti-MUC1-C antibody comprises the CDR1 sequence of SEQ ID NO:4; the CDR2 sequence of SEQ ID NO: 5; and the CDR3 sequence of SEQ ID NO: 6.

In a further embodiment, an anti-MUC1-C antibody comprises any of the heavy chain variable region amino acid sequences of SEQ ID NOs: 7-8 (Table 3).

In a still further embodiment, an anti-MUC1-C antibody comprises the heavy chain variable region sequence of SEQ ID NO: 7.

In a still further embodiment, an anti-MUC1-C antibody comprises the heavy chain variable region sequence of SEQ ID NO: 8.

In some embodiments, a CDR sequence in an anti-MUC1-C antibody of the invention comprises one or two amino acid substitutions relative to a CDR1, CDR2 and/or CDR3 sequence or set of CDR1, CDR2 and CDR3 sequences in any one of SEQ ID NOs: 1-6 (Table 1; Table 2).

In some embodiments, an anti-MUC1-C antibody preferably comprises a heavy chain variable domain (VH) in which the CDR3 sequence has greater than or equal to 80%, such as at least 85%, at least 90%, at least 95%, or at least 99% sequence identity at the amino acid level to a CDR3 sequence of any one of the antibodies whose CDR3 sequences are provided in Table 1 or Table 2, and binds to MUC1 -C.

In some embodiments, an anti-MUC1-C antibody preferably comprises a heavy chain variable domain (VH) in which the full set of CDRs 1, 2, and 3 (combined) has greater than or equal to eighty-five percent (85%) sequence identity at the amino acid level to the CDRs 1, 2, and 3 (combined) of the antibodies whose CDR sequences are provided in Table 1 or Table 2, and binds to MUC1-C.

In some embodiments, an anti-MUC1-C antibody comprises a heavy chain variable region sequence with at least about 80% identity, at least 85% identity, at least 90% identity, at least 95% identity, at least 98% identity, or at least 99% identity to any of the heavy chain variable region sequences of SEQ ID NOs: 7-8 (shown in Table 3), and binds to MUC1-C.

In some embodiments, bispecific or multi-specific antibodies are provided, which may have any of the configurations discussed herein, including, without limitation, a bispecific three-chain antibody-like molecule (TCA). In some embodiments, a multi-specific antibody can comprise at least one heavy chain variable region having binding specificity for MUC1-C, and at least one heavy chain variable region having binding specificity for a protein other than MUC1-C. In some embodiments, a multi-specific antibody can comprise at least one heavy chain variable region that binds to MUC1-C, and at least one heavy chain variable region that binds to a protein other than MUC1-C. In some embodiments, a multi-specific antibody can comprise a heavy chain variable region comprising at least two antigen-binding domains, wherein each of the antigen-binding domains binds to MUC1-C. In some embodiments, a multi-specific antibody can comprise a heavy chain/light chain pair that binds to a first antigen (e.g., CD3), and a heavy chain from a heavy chain-only antibody. In certain embodiments, the heavy chain from the heavy chain-only antibody comprises an Fc portion comprising CH2 and/or CH3 and/or CH4 domains, in the absence of a CH1 domain. In one particular embodiment, a bispecific antibody comprises a heavy chain/light chain pair that binds to an antigen on an effector cell (e.g., a CD3 protein on a T-cell), and a heavy chain from a heavy chain-only antibody comprising an antigen-binding domain that binds to MUC1-C.

In some embodiments, a multi-specific antibody comprises a CD3-binding VH domain that is paired with a light chain variable domain. In certain embodiments, the light chain is a fixed light chain. In some embodiments, the CD3-binding VH domain comprises a CDR1 sequence of SEQ ID NO: 9, a CDR2 sequence of SEQ ID NO: 10, and a CDR3 sequence of SEQ ID NO: 11, in a human VH framework. In some embodiments, the CD3-binding VH domain comprises a CDR1 sequence of SEQ ID NO: 12, a CDR2 sequence of SEQ ID NO: 13, and a CDR3 sequence of SEQ ID NO: 14, in a human VH framework. In some embodiments, the fixed light chain comprises a CDR1 sequence of SEQ ID NO: 15, a CDR2 sequence of SEQ ID NO: 16, and a CDR3 sequence of SEQ ID NO: 17, in a human VL framework. Together, the CD3-binding VH domain and the light chain variable domain have binding affinity for CD3. In some embodiments, a CD3-binding VH domain comprises a heavy chain variable region sequence of SEQ ID NO: 18. In some embodiments, a CD3-binding VH domain comprises a heavy chain variable region sequence of SEQ ID NO: 19. In some embodiments, a CD3-binding VH domain comprises a sequence having at least about 80%, at least about 85%, at least about 90%, at least about 95%, or at least about 99% percent identity to the heavy chain variable region sequence of SEQ ID NO: 18 or 19. In some embodiments, a fixed light chain comprises a light chain variable region sequence of SEQ ID NO: 20. In some embodiments, a fixed light chain comprises a sequence having at least about 80%, at least about 85%, at least about 90%, at least about 95%, or at least about 99% percent identity to the heavy chain variable region sequence of SEQ ID NO: 20.

Multi-specific antibodies comprising the above-described CD3-binding VH domain and light chain variable domain have advantageous properties, for example, as described in published PCT application publication number WO2018/052503, the disclosure of which is incorporated by reference herein in its entirety. Any of the multi-specific antibodies and antigen-binding domains described herein, having binding affinity to MUC1-C, can be combined with the CD3-binding domains and fixed light chain domains described herein (see, e.g., Table 4 and Table 5), as well as additional sequences, such as those provided in Table 6 and Table 7, to generate multi-specific antibodies having binding affinity to one or more MUC1-C epitopes, as well as CD3.

TABLE 4

Anti-CD3 Heavy and Light Chain CDR1, CDR2, CDR3 amino acid sequences.

| | SEQ_aa_CDR1 | SEQ_aa_CDR2 | SEQ_aa_CDR3 |
|---|---|---|---|
| Heavy Chain (F2B) | GFTFDDYA (SEQ ID NO: 9) | ISWNSGSI (SEQ ID NO: 10) | AKDSRGYGDYRLGGAY (SEQ ID NO: 11) |
| Heavy Chain (F2F) | GFTFHNYA (SEQ ID NO: 12) | ISWNSGSI (SEQ ID NO: 13) | AKDSRGYGDYSLGGAY (SEQ ID NO: 14) |
| Light Chain | QSVSSN (SEQ ID NO: 15) | GAS (SEQ ID NO: 16) | QQYNNWPWT (SEQ ID NO: 17) |

TABLE 5

| Anti-CD3 heavy and light chain variable region amino acid sequences. | |
|---|---|
| VH (F2B) | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKDSRGYGDYRLGGAYWGQGTLVTVSS (SEQ ID NO: 18) |
| VH (F2F) | EVQLVESGGGLVQPGRSLRLSCAASGFTFHNYAMHWVRQAPGKGLEWVSGISWNSGSIGYADSVKGRFTISRDNAKNSLYLQMNSLRAEDTALYYCAKDSRGYGDYSLGGAYWGQGTLVTVSS (SEQ ID NO: 19) |
| VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPWTFGQGTKVEIK (SEQ ID NO: 20) |

TABLE 6

| Human IgG1 and IgG4 Fc region sequences. | |
|---|---|
| Human IgG1 (UniProt No. P01857) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 21) |
| Human IgG4 (UniProt No. P01861) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 22) |
| Human IgG1 with silencing mutations (Fc region) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 23) |
| Human IgG4 with silencing mutations (Fc region) | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 24) |

TABLE 7

| additional sequences. | |
|---|---|
| Anti-CD3 light chain constant region sequence (kappa light chain) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 25) |
| Anti-CD3 heavy chain sequence (VH + wt IgG1 Fc) | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKDSRGYGDYRLGGAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 26) |
| Anti-CD3 heavy chain sequence (with silenced IgG1 Fc) | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKDSRGYGDYRLGGAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 27) |
| Anti-CD3 heavy chain constant region sequence (with wt IgG4 Fc) | EVQLVESGGGLVQPGRSLRLSCAASGFTFDDYAMHWVRQAPGKGLEWVSGISWNSGSIGYADSVKGRFTISRDNAKNSLYLQMNSLRAEDTALYYCAKDSRGYGDYRLGGAYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK (SEQ ID NO: 28) |

TABLE 7-continued

| additional sequences. | |
|---|---|
| Anti-CD3 heavy chain constant region sequence (with silenced IgG4 Fc) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCPPCPAPE AAGGPSVFLFPPKPKDTLMISRTPEVTCVVVDVSQEDPEVQFNWYVD GVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNV FSCSVMHEALHNHYTQKSLSLSLGK (SEQ ID NO: 29) |
| Silenced IgG4 (hinge-CH2-CH3; hole (S228P, F234A, L235A; T366S, L368A, Y407V)) | ESKYGPPCP**P**CPAPE**AA**GGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSL**S**C**A**VKGFYPSDIAVEWESNGQPENNYKTTPPVLDSDGSFFL **V**SRLTVDKSRWQEGNVFSCSVMHEALHNHYTQKSLSLSLGK (SEQ ID NO: 30) |
| Silenced IgG4 (hinge-CH2-CH3; knob (S228P, F234A, L235A; T366W)) | ESKYGPPCP**P**CPAPE**AA**GGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEEMT KNQVSL**W**CLVKGFYPSDIAVEWESNGQPENNYKTTPPVLDSDGSFF LYSRLTVDKSRWQEGNVFSCSVMHEALHNHYTQKSLSLSLGK (SEQ ID NO: 31) |
| Anti-CD3 full length light chain (VL + kappa CL) | EIVMTQSPATLSVSPGERATLSCRASQSVSSNLAWYQQKPGQAPRLLI YGASTRATGIPARFSGSGSGTEFTLTISSLQSEDFAVYYCQQYNNWPW TFGQGTKVEIKRTVAAPSVFIFPPSDEQLKSGTASVVCLLNNFYPREAK VQWKVDNALQSGNSQESVTEQDSKDSTYSLSSTLTLSKADYEKHKV YACEVTHQGLSSPVTKSFNRGEC (SEQ ID NO: 32) |
| Anti-CD3 (F2B) full length heavy chain (VH + silenced IgG4 Fc + knob (S228P, F234A, L235A; T366W)) | EVQLVESGGGLVQPGRSLRLSCAASGFTFDDYAMHWVRQAPGKGLE WVSGISWNSGSIGYADSVKGRFTISRDNAKNSLYLQMNSLRAEDTAL YYCAKDSRGYGDYRLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCP**P**CPAPE **AA**GGPSVFLFPPKPKDTLMISRTPEVTCVVVDVSQEDPEVQFNWYVD GVEVHNAKTKPREEQFNSTYRVVSVLTVLHQDWLNGKEYKCKVSNK GLPSSIEKTISKAKGQPREPQVYTLPPSQEEMTKNQVSL**W**CLVKGFYP SDIAVEWESNGQPENNYKTTPPVLDSDGSFFLYSRLTVDKSRWQEGN VFSCSVMHEALHNHYTQKSLSLSLGK (SEQ ID NO: 33) |
| Anti-CD3 (F2F) full length heavy chain (VH + silenced IgG4 Fc + knob (S228P, F234A, L235A; T366W)) | EVQLVESGGGLVQPGRSLRLSCAASGFTFHNYAMHWVRQAPGKGLE WVSGISWNSGSIGYADSVKGRFTISRDNAKNSLYLQMNSLRAEDTAL YYCAKDSRGYGDYSLGGAYWGQGTLVTVSSASTKGPSVFPLAPCSRS TSESTAALGCLVKDYFPEPVTVSWNSGALTSGVHTFPAVLQSSGLYSL SSVVTVPSSSLGTKTYTCNVDHKPSNTKVDKRVESKYGPPCP**P**CPAPE **AA**GGPSVFLFPPKPKDTLMISRTPEVTCVVVDVSQEDPEVQFNWYVD GVEVHNAKTKPREEQFNSTYRVVSVLTVLHQDWLNGKEYKCKVSNK GLPSSIEKTISKAKGQPREPQVYTLPPSQEEMTKNQVSL**W**CLVKGFYP SDIAVEWESNGQPENNYKTTPPVLDSDGSFFLYSRLTVDKSRWQEGN VFSCSVMHEALHNHYTQKSLSLSLGK (SEQ ID NO: 42) |
| Anti-MUC1-C monovalent heavy chain (clone ID 375747) + silenced IgG4 Fc, hole (S228P, F234A, L235A, T366S, L368A, Y407V | EVQLVESGGGLVQPGGSLRLSCTASGFAFSGNSMNWVRQAPGKGLE WVAFITSSGRSIKYADSVKGRFTISRDNAKNSLYLQMNTLRDEDTALY YCATGGTGTSLFDYRGQGTLVTVSSESKYGPPCPPCPAPEAAGGPSVF LFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLSCAVKGFYPSDIAVEWES NGQPENNYKTTPPVLDSDGSFFLVSRLTVDKSRWQEGNVFSCSVMHE ALHNHYTQKSLSLSLGK (SEQ ID NO: 34) |
| Anti-MUC1-C bivalent heavy chain (clone ID 375747) + silenced IgG4 Fc, hole (S228P, F234A, L235A, T366S, L368A, Y407V | EVQLVESGGGLVQPGGSLRLSCTASGFAFSGNSMNWVRQAPGKGLE WVAFITSSGRSIKYADSVKGRFTISRDNAKNSLYLQMNTLRDEDTALY YCATGGTGTSLFDYRGQGTLVTVSSGGGGSGGGGSEVQLVESGGGL VQPGGSLRLSCTASGFAFSGNSMNWVRQAPGKGLEWVAFITSSGRSI KYADSVKGRFTISRDNAKNSLYLQMNTLRDEDTALYYCATGGTGTSL FDYRGQGTLVTVSSESKYGPPCPPCPAPEAAGGPSVFLFPPKPKDTLMI SRTPEVTCVVVDVSQEDPEVQFNWYVDGVEVHNAKTKPREEQFNST YRVVSVLTVLHQDWLNGKEYKCKVSNKGLPSSIEKTISKAKGQPREP QVYTLPPSQEEMTKNQVSLSCAVKGFYPSDIAVEWESNGQPENNYKT TPPVLDSDGSFFLVSRLTVDKSRWQEGNVFSCSVMHEALHNHYTQKS LSLSLGK (SEQ ID NO: 35) |
| Anti-MUC1-C monovalent heavy | EVQLVESGGGLVQPGGSLRLSCAASGFTFSSHSMNWVRQAPGKGLE WVSFISSSSNIKKYADSVKGRFTISRDNAKNSLFLQMNSLRDEDTAVY |

TABLE 7-continued

| additional sequences. | |
|---|---|
| chain (clone ID 375505) + silenced IgG4 Fc, hole (S228P, F234A, L235A, T366S, L368A, Y407V | YCATGGTGITVLDYRGQGTLVTVSSESKYGPPCPPCPAPEAAGGPSVF LFPPKPKDTLMISRTPEVTCVVVDVSQEDPEVQFNWYVDGVEVHNAK TKPREEQFNSTYRVVSVLTVLHQDWLNGKEYKCKVSNKGLPSSIEKTI SKAKGQPREPQVYTLPPSQEEMTKNQVSLSCAVKGFYPSDIAVEWES NGQPENNYKTTPPVLDSDGSFFLVSRLTVDKSRWQEGNVFSCSVMHE ALHNHYTQKSLSLSLGK (SEQ ID NO: 36) |
| Anti-MUC1-C bivalent havy chain (clone ID 375505) + silenced IgG4 Fc, hole (S228P, F234A, L235A, T366S, L368A, Y407V | EVQLVESGGGLVQPGGSLRLSCAASGFTFSSHSMNWVRQAPGKGLE WVSFISSSSNIKKYADSVKGRFTISRDNAKNSLFLQMNSLRDEDTAVY YCATGGTGITVLDYRGQGTLVTVSSGGGGSGGGGSEVQLVESGGGLV QPGGSLRLSCAASGFTFSSHSMNWVRQAPGKGLEWVSFISSSSNIKKY ADSVKGRFTISRDNAKNSLFLQMNSLRDEDTAVYYCATGGTGITVLD YRGQGTLVTVSSESKYGPPCPPCPAPEAAGGPSVFLFPPKPKDTLMISR TPEVTCVVVDVSQEDPEVQFNWYVDGVEVHNAKTKPREEQFNSTYR VVSVLTVLHQDWLNGKEYKCKVSNKGLPSSIEKTISKAKGQPREPQV YTLPPSQEEMTKNQVSLSCAVKGFYPSDIAVEWESNGQPENNYKTTPP VLDSDGSFFLVSRLTVDKSRWQEGNVFSCSVMHEALHNHYTQKSLSL SLGK (SEQ ID NO: 37) |
| Anti-MUC1-C bivalent havy chain (clone ID 375747 × clone ID 375505) + silenced IgG4 Fc, hole (S228P, F234A, L235A, T366S, L368A, Y407V | EVQLVESGGGLVQPGGSLRLSCTASGFAFSGNSMNWVRQAPGKGLE WVAFITSSGRSIKYADSVKGRFTISRDNAKNSLYLQMNTLRDEDTALY YCATGGTGTSLFDYRGQGTLVTVSSGGGGSGGGGSEVQLVESGGGL VQPGGSLRLSCAASGFTFSSHSMNWVRQAPGKGLEWVSFISSSSNIKK YADSVKGRFTISRDNAKNSLFLQMNSLRDEDTAVYYCATGGTGITVL DYRGQGTLVTVSSESKYGPPCPPCPAPEAAGGPSVFLFPPKPKDTLMIS RTPEVTCVVVDVSQEDPEVQFNWYVDGVEVHNAKTKPREEQFNSTY RVVSVLTVLHQDWLNGKEYKCKVSNKGLPSSIEKTISKAKGQPREPQ VYTLPPSQEEMTKNQVSLSCAVKGFYPSDIAVEWESNGQPENNYKTT PPVLDSDGSFFLVSRLTVDKSRWQEGNVFSCSVMHEALHNHYTQKSL SLSLGK (SEQ ID NO: 38) |
| Anti-MUC1-C bivalent heavy chain (clone ID 375505 × clone ID 375747) + silenced IgG4 Fc, hole (S228P, F234A, L235A, T366S, L368A, Y407V | EVQLVESGGGLVQPGGSLRLSCAASGFTFSSHSMNWVRQAPGKGLE WVSFISSSSNIKKYADSVKGRFTISRDNAKNSLFLQMNSLRDEDTAVY YCATGGTGITVLDYRGQGTLVTVSSGGGGSGGGGSEVQLVESGGGLV QPGGSLRLSCTASGFAFSGNSMNWVRQAPGKGLEWVAFITSSGRSIK YADSVKGRFTISRDNAKNSLYLQMNTLRDEDTALYYCATGGTGTSLF DYRGQGTLVTVSSESKYGPPCPPCPAPEAAGGPSVFLFPPKPKDTLMIS RTPEVTCVVVDVSQEDPEVQFNWYVDGVEVHNAKTKPREEQFNSTY RVVSVLTVLHQDWLNGKEYKCKVSNKGLPSSIEKTISKAKGQPREPQ VYTLPPSQEEMTKNQVSLSCAVKGFYPSDIAVEWESNGQPENNYKTT PPVLDSDGSFFLVSRLTVDKSRWQEGNVFSCSVMHEALHNHYTQKSL SLSLGK (SEQ ID NO: 39) |

In some embodiments, bispecific or multi-specific antibodies are provided, which may have any of the configurations discussed herein, including, without limitation, a bispecific three-chain antibody like molecule (TCA). In some embodiments, a bispecific antibody can comprise at least one heavy chain variable region that binds to MUC1-C, and at least one heavy chain variable region that binds to a protein other than MUC1-C. In some embodiments, a bispecific antibody can comprise a heavy chain/light chain pair that binds to a first antigen, and a heavy chain from a heavy chain-only antibody, comprising an Fc portion comprising CH2 and/or CH3 and/or CH4 domains, in the absence of a CH1 domain, and an antigen binding domain that binds an epitope of a second antigen or a different epitope of the first antigen. In one particular embodiment, a bispecific antibody comprises a heavy chain/light chain pair that binds to an antigen on an effector cell (e.g., a CD3 protein on a T-cell), and a heavy chain from a heavy chain-only antibody comprising an antigen-binding domain that binds to MUC1-C.

In some embodiments, where an antibody of the invention is a bispecific antibody, one arm of the antibody (one binding moiety, or one binding unit) is specific for human MUC1-C, while the other arm may be specific for target cells, tumor-associated antigens, targeting antigens, e.g., integrins, etc., pathogen antigens, checkpoint proteins, and the like. Target cells specifically include cancer cells, including, without limitation, cells associated with solid tumors and/or hematological malignancies characterized by the expression of MUC1-C. In some embodiments, one arm of the antibody (one binding moiety, or one binding unit) is specific for human MUC1-C, while the other arm is specific for CD3.

In some embodiments, an antibody comprises an anti-CD3 light chain polypeptide comprising the sequence of SEQ ID NO: 32, an anti-CD3 heavy chain polypeptide comprising the sequence of SEQ ID NO: 18 or 19, and an anti-MUC1-C heavy chain polypeptide comprising the sequence of SEQ ID NO: 7 or 8, in a monovalent or bivalent configuration, linked to the sequence of any one of SEQ ID NOs: 30 or 31. These sequences can be combined in various ways to produce a bispecific antibody of a desired IgG subclass, e.g., IgG1, IgG4, silenced IgG1, silenced IgG4. In one preferred embodiment, an antibody is a TCA comprising a first polypeptide comprising SEQ ID NO: 32, a second polypeptide comprising SEQ ID NO: 33, and a third polypeptide comprising SEQ ID NO: 34, 35, 36, 37, 38 or 39.

Various formats of multi-specific antibodies are within the ambit of the invention, including, without limitation, single chain polypeptides, two chain polypeptides, three chain polypeptides, four chain polypeptides, and multiples thereof. The multi-specific antibodies herein specifically include T-cell multi-specific (e.g., bispecific) antibodies binding to MUC1-C and CD3 (anti-MUC1-C x anti-CD3 antibodies). Such antibodies induce potent T-cell mediated killing of cells expressing MUC1-C.

Preparation of Anti-MUCI-C Antibodies

The antibodies of the present invention can be prepared by methods known in the art. In a preferred embodiment, the antibodies herein are produced by transgenic animals, including transgenic mice and rats, preferably rats, in which the endogenous immunoglobulin genes are knocked out or disabled. In a preferred embodiment, the heavy chain antibodies herein are produced in a UniRat™ UniRats™ have their endogenous immunoglobulin genes silenced and use a human immunoglobulin heavy-chain translocus to express a diverse, naturally optimized repertoire of fully human HCAbs. While endogenous immunoglobulin loci in rats can be knocked out or silenced using a variety of technologies, in UniRat™ the zinc-finger (endo)nuclease (ZNF) technology was used to inactivate the endogenous rat heavy chain J-locus, light chain Cκ locus and light chain Cλ locus. ZNF constructs for microinjection into oocytes can produce IgH and IgL knock out (KO) lines. For details see, e.g., Geurts et al., 2009, Science 325:433. Characterization of Ig heavy chain knockout rats has been reported by Menoret et al., 2010, Eur. J. Immunol. 40:2932-2941. Advantages of the ZNF technology are that non-homologous end joining to silence a gene or locus via deletions up to several kb can also provide a target site for homologous integration (Cui et al., 2011, Nat Biotechnol 29:64-67). Human heavy chain antibodies produced in a UniRat™ are called UniAbs™ and can bind epitopes that cannot be attacked with conventional antibodies. Their high specificity, affinity, and small size make them ideal for mono- and poly-specific applications.

In addition to UniAbs™, specifically included herein are heavy chain-only antibodies lacking the camelid VHH framework and mutations, and their functional VH regions. Such heavy chain-only antibodies can, for example, be produced in transgenic rats or mice which comprise fully human heavy chain-only gene loci as described, e.g., in WO2006/008548, but other transgenic mammals, such as rabbit, guinea pig, rat can also be used, rats and mice being preferred. Heavy chain-only antibodies, including their VHH or VH functional fragments, can also be produced by recombinant DNA technology, by expression of the encoding nucleic acid in a suitable eukaryotic or prokaryotic host, including, for example, mammalian cells (e.g., CHO cells), *E. coli* or yeast.

Domains of heavy chain-only antibodies combine advantages of antibodies and small molecule drugs: can be mono- or multi-valent; have low toxicity; and are cost-effective to manufacture. Due to their small size, these domains are easy to administer, including oral or topical administration, are characterized by high stability, including gastrointestinal stability; and their half-life can be tailored to the desired use or indication. In addition, VH and VHH domains of HCAbs can be manufactured in a cost-effective manner.

In a particular embodiment, the heavy chain antibodies of the present invention, including UniAbs™, have the native amino acid residue at the first position of the FR4 region (amino acid position 101 according to the Kabat numbering system), substituted by another amino acid residue, which is capable of disrupting a surface-exposed hydrophobic patch comprising or associated with the native amino acid residue at that position. Such hydrophobic patches are normally buried in the interface with the antibody light chain constant region but become surface exposed in HCAbs and are, at least partially, for the unwanted aggregation and light chain association of HCAbs. The substituted amino acid residue preferably is charged, and more preferably is positively charged, such as lysine (Lys, K), arginine (Arg, R) or histidine (His, H), preferably arginine (R). In a preferred embodiment the heavy chain-only antibodies derived from the transgenic animals contain a Trp to Arg mutation at position 101. The resultant HCAbs preferably have high antigen-binding affinity and solubility under physiological conditions in the absence of aggregation.

As part of the present invention, human IgG anti-MUC1-C heavy chain antibodies with unique sequences from UniRat™ animals (UniAb™) were identified that bind to human MUC1-C in ELISA protein and cell-binding assays. The identified heavy chain variable region (VH) sequences are positive for human MUC1-C protein binding and/or for binding to MUC1-C+cells, and are all negative for binding to cells that do not express MUC1-C.

Heavy chain antibodies binding to non-overlapping epitopes on a MUC1-C protein, e.g., UniAbs™ can be identified by competition binding assays, such as enzyme-linked immunoassays (ELISA assays) or flow cytometric competitive binding assays. For example, one can use competition between known antibodies binding to the target antigen and the antibody of interest. By using this approach, one can divide a set of antibodies into those that compete with the reference antibody and those that do not. The non-competing antibodies are identified as binding to a distinct epitope that does not overlap with the epitope bound by the reference antibody. Often, one antibody is immobilized, the antigen is bound, and a second, labeled (e.g., biotinylated) antibody is tested in an ELISA assay for ability to bind the captured antigen. This can be performed also by using surface plasmon resonance (SPR) platforms, including ProteOn XPR36 (BioRad, Inc), Biacore 2000 and Biacore T200 (GE Healthcare Life Sciences), and MX96 SPR imager (Ibis technologies B.V.), as well as on biolayer interferometry platforms, such as Octet Red384 and Octet HTX (ForteBio, Pall Inc). For further details see the examples herein.

Typically, an antibody "competes" with a reference antibody if it causes about 15-100% reduction in the binding of the reference antibody to the target antigen, as determined by standard techniques, such as by the competition binding assays described above. In various embodiments, the relative inhibition is at least about 15%, at least about 20%, at least about 25%, at least about 30%, at least about 35%, at least about 40%, at least about 45%, at least about 50% at least about 55%, at least about 60%, at least about 65%, at least about 70%, at least about 75%, at least about 80%, at least about 85%, at least about 90%, at least about 95% or higher.

Pharmaceutical Compositions, Uses and Methods of Treatment

It is another aspect of the present invention to provide pharmaceutical compositions comprising one or more antibodies of the present invention in admixture with a suitable pharmaceutically acceptable carrier. Pharmaceutically acceptable carriers as used herein are exemplified, but not limited to, adjuvants, solid carriers, water, buffers, or other carriers used in the art to hold therapeutic components, or combinations thereof.

In one embodiment, a pharmaceutical composition comprises a heavy chain antibody (e.g., UniAb™) that binds to MUC1-C. In another embodiment, a pharmaceutical composition comprises a multi-specific (including bispecific) heavy chain antibody (e.g., UniAb™) with binding specificity for two or more non-overlapping epitopes on a MUC1-C protein. In a preferred embodiment, a pharmaceutical composition comprises a multi-specific (including bispecific and TCA) heavy chain antibody (e.g., UniAb™) with binding specificity to MUC1-C and with binding specificity to a binding target on an effector cell (e.g., a binding target on a T-cell, such as, e.g., a CD3 protein on a T-cell). In a preferred embodiment, a pharmaceutical composition comprises a multi-specific (including bispecific and TCA) heavy chain antibody (e.g., UniAb™) that binds to MUC1-C and that binds to a binding target on an effector cell (e.g., a binding target on a T-cell, such as, e.g., a CD3 protein on a T-cell).

Pharmaceutical compositions of the antibodies used in accordance with the present invention are prepared for storage by mixing proteins having the desired degree of purity with optional pharmaceutically acceptable carriers, excipients or stabilizers (see, e.g. Remington's Pharmaceutical Sciences 16th edition, Osol, A. Ed. (1980)), such as in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). The formulation depends on the route of administration chosen. The antibodies herein can be administered by intravenous injection or infusion or subcutaneously. For injection administration, the antibodies herein can be formulated in aqueous solutions, preferably in physiologically-compatible buffers to reduce discomfort at the site of injection. The solution can contain carriers, excipients, or stabilizers as discussed above. Alternatively, antibodies can be in lyophilized form for constitution with a suitable vehicle, e.g., sterile pyrogen-free water, before use.

Antibody formulations are disclosed, for example, in U.S. Pat. No. 9,034,324. Similar formulations can be used for the heavy chain antibodies, including UniAbs™, of the present invention. Subcutaneous antibody formulations are described, for example, in US20160355591 and US20160166689.

Methods of Use

The anti-MUC1-C antibodies and pharmaceutical compositions described herein can be used for the treatment of diseases and conditions characterized by the expression of MUC1-C, including, without limitation, the conditions and diseases described further herein.

Mucin 1 (MUC1) is a heavily glycosylated, single pass type I transmembrane protein. The N-terminal subunit (MUC1-N) and C-terminal subunit (MUC1-C) form a stable heterodimeric complex. MUC1 is highly polymorphic, with greater than 90 isoforms, differing in the number of tandem repeats in the VNTR (variable number tandem repeat) region of the N-terminal subunit. Mucins line the apical surface of epithelial cells in the lungs, stomach, mammary glands, intestines, and several other organs. In healthy tissues, mucins protect the body from infection. Aberrantly glycosylated MUC1 is overexpressed in human epithelial cancers and apical polarity is lost in tumor cells (Sousa et al. 2016, PMC: 4998183, Nath and Mukherjee, 2014, PMID: 5500204). MUC1 can be cleaved by proteases and cleaved MUC1-N is shed from the cell and can trigger inflammation. The non-shed oncogenic MUC1-C subunit is short, containing a 58 amino acid membrane proximal extracellular domain that shows promise as a target for antibody drug conjugates, monoclonal antibodies and CAR-T therapies (Panchamoorthy et al., 2018, PMC: 6124453; Kufe, 2009, PMC: 2951677).

In one aspect, the anti-MUC1-C antibodies (e.g., UniAbs™) and pharmaceutical compositions herein can be used to treat disorders characterized by the expression of MUC1-C, including, without limitation, the diseases and disorders described further herein.

The anti-MUC1-C heavy chain-only antibodies (UniAbs) of the present invention can be used to develop therapeutic agents for the treatment of cancers, including solid tumors and hematological malignancies, such as those described further herein. Solid tumors include cancers of epithelial origin, i.e., carcinomas, including adenocarcinomas and squamous cell carcinomas. Non-limiting examples of carcinomas include: breast, non-small cell lung (NSCL), small cell lung (SSC), mesothelioma, renal cell, colorectal, ovarian, head and neck squamous cell, nasopharyngeal, gastric, prostatic, pancreatic, esophageal, and cervical carcinomas. Hematological malignancies include, without limitation, myelomas, leukemias, and lymphomas. Non-limiting examples of hematological malignancies include multiple myeloma and chronic myeloid leukemia (CML). Although some monoclonal antibodies have shown promise for treating these diseases, consistent clinical efficacy has not yet been conclusively demonstrated. There is therefore a great need for new therapies, including immunotherapies, for these cancers.

In one embodiment, the antibodies herein can be in the form of heavy chain-only anti-MUC1-C antibody-CAR structures, i.e., heavy chain-only anti-MUC1-C antibody-CAR-transduced T-cell structures. FIG. 4 is a schematic illustration of a CAR-T structure comprising an anti-MUC1-C extracellular binding domain comprising a heavy chain variable region (VH) sequence in accordance with embodiments of the invention.

Effective doses of the compositions of the present invention for the treatment of disease vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g., companion animals such as dogs, cats, horses, etc., laboratory mammals such as rabbits, mice, rats, etc., and the like. Treatment dosages can be titrated to optimize safety and efficacy.

Dosage levels can be readily determined by the ordinarily skilled clinician, and can be modified as required, e.g., as required to modify a subject's response to therapy. The amount of active ingredient that can be combined with the carrier materials to produce a single dosage form varies depending upon the host treated and the particular mode of administration. Dosage unit forms generally contain between from about 1 mg to about 500 mg of an active ingredient.

In some embodiments, the therapeutic dosage the agent may range from about 0.0001 to 100 mg/kg, and more usually 0.01 to 5 mg/kg, of the host body weight. For example, dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

Typically, compositions are prepared as injectables, either as liquid solutions or suspensions; solid forms suitable for solution in, or suspension in, liquid vehicles prior to injection can also be prepared. The pharmaceutical compositions herein are suitable for intravenous or subcutaneous administration, directly or after reconstitution of solid (e.g., lyophilized) compositions. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the antibodies and antibody structures described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in formulating a dosage range that is not toxic for use in humans. The dosage of the antibodies described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g., a chemotherapeutic drug, etc. Kits typically include a label indicating the intended use of the contents of the kit. The term "label" as used herein includes any writing, or recorded material supplied on or with a kit, or which otherwise accompanies a kit.

The invention now being fully described, it will be apparent to one of ordinary skill in the art that various changes and modifications can be made without departing from the spirit or scope of the invention.

EXAMPLES

Example 1

Binding to MUC1-C+ Raji Cells

Binding to MUC1-C-positive Raji cells was assessed by flow cytometry. Briefly, 50,000 target cells were stained with a dilution series of purified UniAbs™ for 30 minutes at 4° C. Following incubation, the cells were washed twice with flow cytometry buffer (1X PBS, 1% BSA, 0.1% NaN 3) and stained with goat $F(ab')_2$ anti-human IgG conjugated to R-phycoerythrin (PE) (Southern Biotech, cat. #2042-09) to detect cell-bound antibodies. After a 20-minute incubation at 4° C., the cells were washed twice with flow cytometry buffer and the mean fluorescence intensity (MFI) was measured by flow cytometry. The MFI of cells stained with secondary antibody alone was used for determination of background signal, and binding of each antibody was converted to fold over background.

The results are provided in FIG. 1, which summarizes the target binding activity of the indicated anti-MUC1-C antibodies. Column 1 indicates the clone ID of the HCAb. Column 2 indicates binding to Raji cells measured as fold over background MFI signal. Column 3 indicates binding to CHO cells that do not express MUC1-C protein (negative control) measured as fold over background MFI signal.

Example 2

Binding to MUC1-C+ Raji Cells

Cell-binding dose curves were performed on Raji MUC1-C+cells, as described in Example 1. The antibodies were tested at a starting concentration of 150 nM followed by 3-fold serial dilutions for an 8-point dose curve. PE mean fluorescence intensity was plotted as a fold over background (cells incubated with secondary detection antibody only). The results are provided in FIG. 2.

Example 3

Cell Binding EC50 Values on MUC1-C+ Raji Cells

For determining cell binding EC50 values, cell binding dose curves were performed on Raji cells that express MUC1-C, as described above. The antibodies were tested at a starting dose of 150 nM, followed by 3-fold serial dilutions for an 8-point dose curve. The transformed data was plotted as an xy-graph using a non-linear regression curve fit (available in GraphPad Prism 8.4.3) to obtain the EC50s (nM). The results are provided in FIG. 3 (column 2 provides the EC50 values, in units of nM).

Example 4

CAR-T-Mediated T-Cell Activation by Human Tumor Cells

CAR-T cell activity was measured by transfecting Jurkat T lymphocyte cells with an anti-MUC1-C CAR and a 6x NFAT TK nano luciferase reporter. Transfected Jurkats were co-cultured for 24 hours with MUC1-C+Raji cells stably transfected to express human MUC1-C, or MUC1-C-negative Raji cells. Luciferase activity was measured using the Promega Nano-Glo Luciferase Assay System (catalog # N1110) and data were normalized to co-culture containing the CAR transfected Jurkat and MUC1-C negative Raji cell lines. Statistical significance was determined using an unpaired, two-tailed t-test. The results are provided in FIG. 4, Panels B and C.

FIG. 4, Panel A, is a schematic illustration of a CAR-T structure comprising an anti-MUC1-C extracellular binding domain comprising an antibody sequence in accordance with aspects of the invention. Panel B depicts T-cell activity of Jurkats transfected an anti-MUC1-C 375747 CAR with Raji-MUC1-C+(*p=0.0009). Panel C depicts T-cell activity of Jurkats transfected with an anti-MUC1-C 375505 CAR with Raji-MUC1-C+ (p=0.0019). These results demonstrate that T-cell activation was specific to MUC1-C target binding, as co-culture with the MUC1-C-negative Raji cells, or incubation of the transfected Jurkats alone, did not result in appreciable luciferase reporter signal.

Example 5

Tumor Control by CAR-T-Mediated T-Cell Activation Assessment in vivo

A pre-clinical evaluation of tumor growth was assessed for antibody constructs corresponding to Clone ID Nos. 375505 and 375747 using a murine xenograft model of a triple-negative breast cancer (TNBC). A GFP- and luciferase-expressing MDA-MB-468 cell line (MDA-MB-468.1ucGFP; 5×10ˆ6 cells) was injected subcutaneously into NOD.Cg-Prkdc$^{scid}$Il2rg$^{tm1/Wjl}$/Szj (NSG) mice to assess in vivo anti-tumor efficacy of VH chimeric antigen receptors (VCARs). Untreated mice (PBS) served as controls. For the in vivo studies, all CAR-T cells were produced using PiggyBac (PB) delivery of the VCAR plasmids. The mice were injected in the axilla with MDA-MB-468 (n=17 to account for variability) and treated when tumors were established (100-200 mm3 by caliper measurement, 39 days post implantation). Mice (n=4/group and staged by tumor volume) were treated with a 'stress' dose (2.5×10ˆ6) of CAR-Ts by IV injection. Whole blood was collected every 7 days and tumor volume was assessed by caliper measurement every 3 days until study completion at day 32 post CAR-T infusion.

Figure 5:
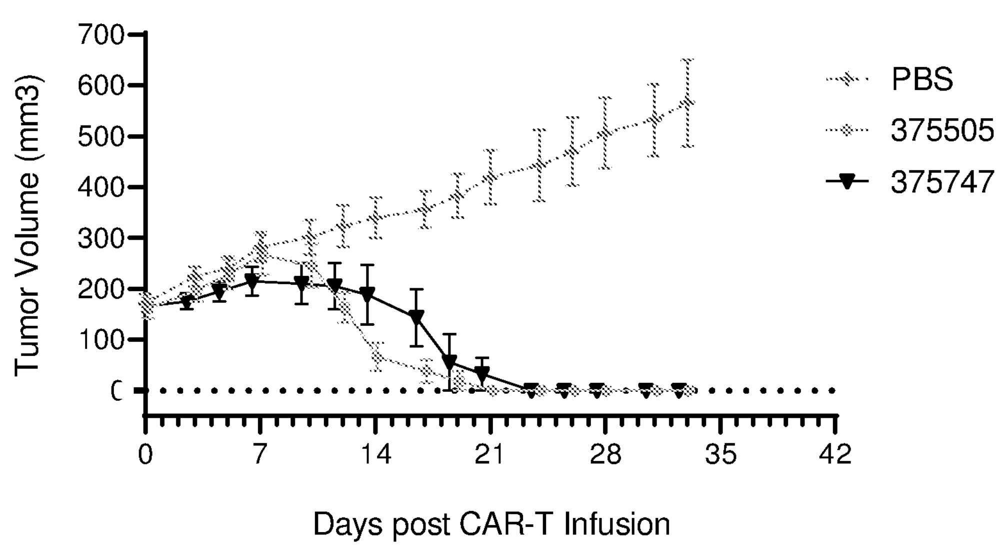
FIG. 5, Panel A, is a graph showing tumor progression as a function of days post CAR-T infusion for the indicated antibody constructs.
Figure 5:
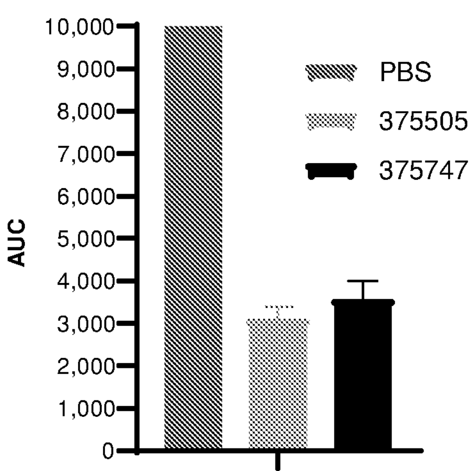

FIG. 5, Panel A, is a graph showing tumor progression as a function of days post CAR-T infusion for the indicated antibody constructs in the pre-clinical evaluation. Tumor volume assessment was completed by caliper measurement. CAR-T cells comprising the indicated antibody constructs (Clone ID: 375505 and 375747) showed strong tumor control compared to untreated mice. For example, shortly after treatment, a sharp decline in tumor volume is seen for Clone ID Nos 375505 and 375747. In contrast, tumor volume continued to climb in untreated mice after treatment administration of the control.

FIG. 5, Panel B, is a bar chart showing the area under curve (AUC) of the graph shown in FIG. 5, Panel A, for the indicated antibody constructs. Untreated mice showed substantially higher AUC in comparison to Clone ID Nos 375505 and 375747.

Example 6

T-Cell Expansion for CAR-T Assessment in vivo

Figure 6:
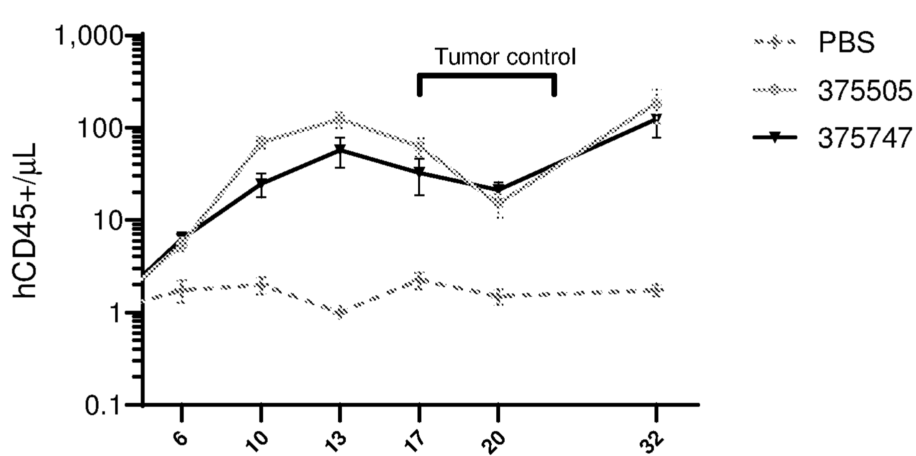
FIG. 6, Panel A, is a graph showing in vivo T-cell count in blood as a function of days post CAR-T infusion for the indicated antibody constructs.
Figure 6:
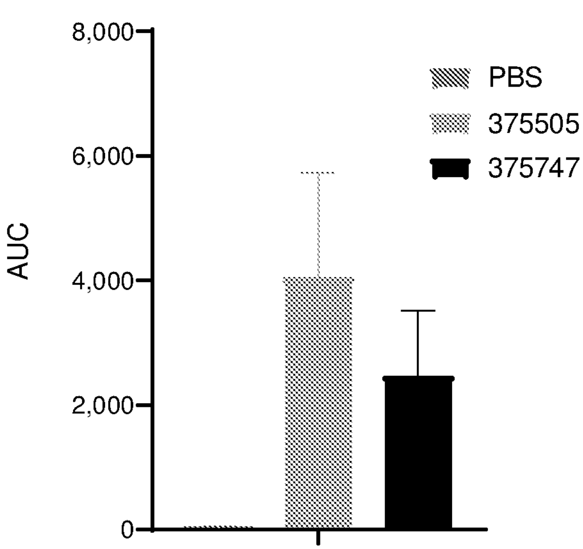

The same pre-clinical evaluation described in Example 5 was used to evaluate T-cell expansion. FIG. 6, Panel A, is a graph showing in vivo T-cell count in blood as a function of days post CAR-T infusion for the indicated antibody constructs. Robust T-cell expansion for mice treated with CAR-T cells comprising the indicated antibody constructs (Clone ID: 375505 and 375747) is shown. On day 0 the mice showed a low T-cell count. Following treatment with CAR-T cells comprising the indicated antibody constructs (Clone ID: 375505 and 375747), a sharp increase in T-cell count was seen compared with no change in untreated mice. For untreated mice, the T-cell count remained consistently low and unchanged over the course of the study.

FIG. 6, Panel B, is a bar chart showing the area under curve (T-cell count totals) of the graph shown in FIG. 6, Panel A, for the indicated antibody constructs. The total T-cell counts for both antibody constructs are significant compared to those for untreated mice.

Example 7

Tumor Control by CAR-T-Mediated T-Cell Activation Assessment in vivo

A pre-clinical evaluation of tumor growth was assessed for antibody constructs corresponding to Clone ID Nos. 375505 and 375747 using a murine xenograft model of ovarian cancer. A GFP- and luciferase- expressing adenocarcinoma OVCAR-3 cell line (OVCAR-3.lucGFP; 5×10ˆ6 cells) was injected subcutaneously into NOD.Cg-Prkdc$^{scid}$Il2rg$^{tm1Wjl}$/Szj (NSG) mice to assess in vivo anti-tumor efficacy of VH chimeric antigen receptors (VCARs). Untreated mice (PBS) served as controls. For the in vivo studies, all CAR-T cells were produced using PiggyBac (PB) delivery of the VCAR plasmids. The mice were injected with tumor cells (n=17 to account for variability) and treated when tumors were established (flux greater than 1×10ˆ8 photons/sec by bioluminescent imaging (BLI), 14 days post implantation). Mice (n=4/group and staged by tumor volume) were treated with a 'stress' dose (8×10ˆ6) of CAR-Ts by IV injection. Whole blood was collected every 7 days and tumor volume was assessed by BLI measurement every 7 days until study completion at day 56 post CAR-T infusion.

Figure 7:
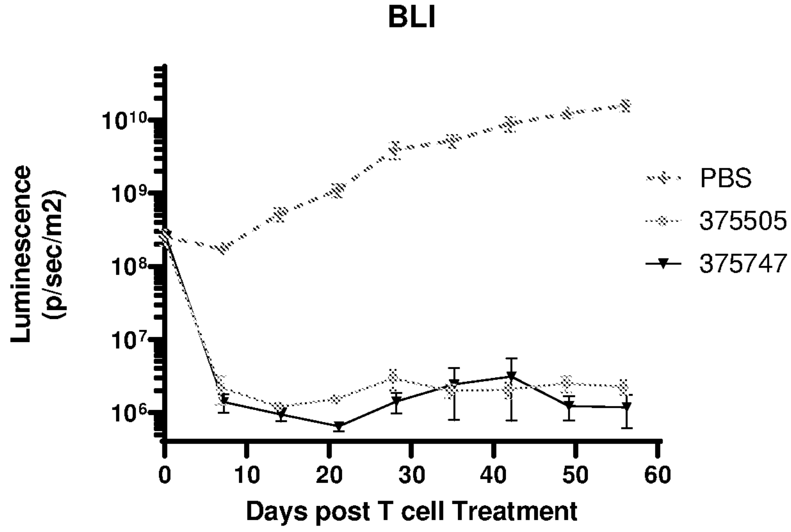
FIG. 7, Panel A, is a graph showing tumor progression as a function of days post CAR-T infusion for the indicated antibody constructs.
Figure 7:
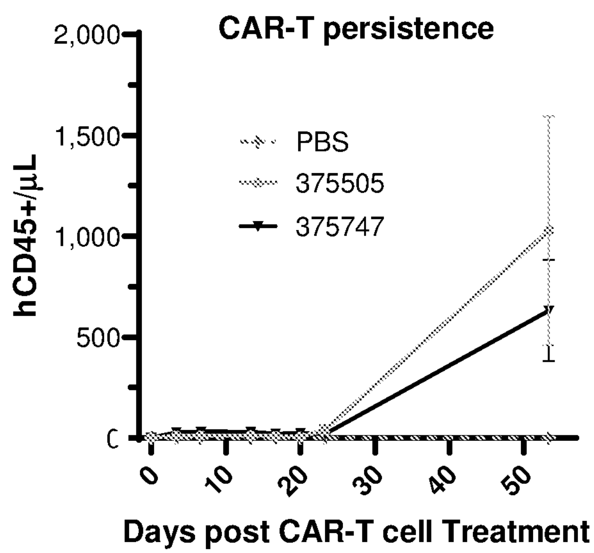

FIG. 7, Panel A, is a graph showing tumor progression as a function of days post CAR-T infusion for the indicated antibody constructs in the pre-clinical evaluation. Tumor volume assessment was completed by BLI measurement. CAR-T cells comprising the indicated antibody constructs (Clone ID: 375505 and 375747) showed strong tumor control compared to untreated mice. For example, shortly after treatment, a sharp decline in tumor volume is seen for Clone ID Nos 375505 and 375747. In contrast, tumor volume continued to climb in untreated mice after treatment administration of the control.

FIG. 7, Panel B, is a line graph showing T-cell persistence in blood measured over time for the indicated antibody constructs. Untreated mice showed substantially higher AUC in comparison to Clone ID Nos 375505 and 375747.

Example 8

T-Cell Expansion for CAR-T Assessment in vivo

Figure 8:
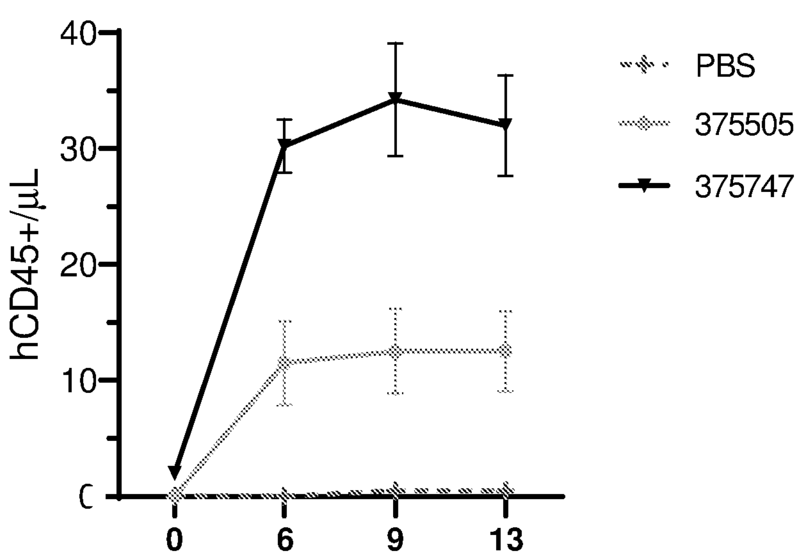
FIG. 8, Panel A, is a graph showing in vivo T-cell count in blood as a function of days post CAR-T infusion for the indicated antibody constructs.
Figure 8:
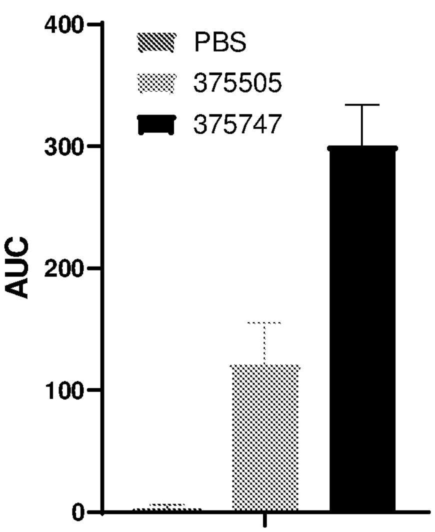

The same pre-clinical evaluation described in Example 7 was used to evaluate T-cell expansion. FIG. 8, Panel A, is a graph showing in vivo T-cell count in blood as a function of days post CAR-T infusion for the indicated antibody constructs. Robust T-cell expansion for mice treated with CAR-T cells comprising the indicated antibody constructs (Clone ID: 375505 and 375747) is shown. On day 0 the mice showed a low T-cell count. Following treatment with CAR-T cells comprising the indicated antibody constructs (Clone ID: 375505 and 375747), a sharp increase in T-cell count was seen compared with no change in untreated mice. For untreated mice, the T-cell count remained consistently low and unchanged over the course of the study.

FIG. 8, Panel B, is a bar chart showing the area under curve (T-cell count totals) of the graph shown in FIG. 8, Panel A, for the indicated antibody constructs. The total T-cell counts for both antibody constructs is significant compared to those for untreated mice.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An isolated antibody that binds to MUC1-C, comprising a heavy chain variable region comprising:

(a) a CDR1 sequence of SEQ ID NO: 1, a CDR2 sequence of SEQ ID NO: 2, and a CDR3 sequence of SEQ ID NO: 3; or (b) a CDR1 sequence of SEQ ID NO: 4, a CDR2 sequence of SEQ ID NO: 5, and a CDR3 sequence of SEQ ID NO: 6.

2. A CAR-T cell comprising a CAR comprising an extracellular antigen-binding domain that binds to MUC1-C, comprising a heavy chain variable region comprising:

(a) a CDR1 sequence of SEQ ID NO: 1, a CDR2 sequence of SEQ ID NO: 2, and a CDR3 sequence of SEQ ID NO: 3; or (b) a CDR1 sequence of SEQ ID NO: 4, a CDR2 sequence of SEQ ID NO: 5, and a CDR3 sequence of SEQ ID NO: 6.

3. The CAR-T cell of claim 2, wherein the CDR1, CDR2 and CDR3 sequences are present in a human VH framework.

4. The CAR-T cell of claim 2, wherein the heavy chain variable region comprises a CDR1 sequence of SEQ ID NO: 1, a CDR2 sequence of SEQ ID NO: 2, and a CDR3 sequence of SEQ ID NO: 3.

5. The CAR-T cell of claim 2, wherein the heavy chain variable region comprises a CDR1 sequence of SEQ ID NO: 4, a CDR2 sequence of SEQ ID NO: 5, and a CDR3 sequence of SEQ ID NO: 6.

6. The CAR-T cell of claim 2, wherein the extracellular antigen-binding domain that binds to MUC1-C comprises a heavy chain variable region having at least 95% sequence identity to SEQ ID NO: 7 or SEQ ID NO: 8.

7. The CAR-T cell of claim 6, wherein the extracellular antigen-binding domain that binds to MUC1-C comprises a heavy chain variable region sequence selected from the group consisting of: SEQ ID NOs: 7 and 8.

8. The CAR-T cell of claim 7, wherein the extracellular antigen-binding domain that binds to MUC1-C comprises the heavy chain variable region sequence of SEQ ID NO: 7.

9. The CAR-T cell of claim 7, wherein the extracellular antigen-binding domain that binds to MUC1-C comprises the heavy chain variable region sequence of SEQ ID NO: 8.

10. A pharmaceutical composition comprising the CAR-T cell of claim 2.

11. A kit comprising the CAR-T cell of claim 2 and instructions for use.

12. The kit of claim 11, further comprising at least one additional reagent.

13. The kit of claim 12, wherein the at least one additional reagent comprises a chemotherapeutic drug.

* * * * *